(12) United States Patent
Chaudhary

(10) Patent No.: US 12,305,186 B2
(45) Date of Patent: May 20, 2025

(54) METHODS FOR EXPANDING SARS-COV2-ANTIGEN-SPECIFIC T CELLS, COMPOSITIONS AND USES RELATED THERETO

(71) Applicant: Angeles Therapeutics, Inc., Toluca Lake, CA (US)

(72) Inventor: Preet M. Chaudhary, Toluca Lake, CA (US)

(73) Assignee: Angeles Therapeutics, Inc., Toluca Lake, CA (US)

(*) Notice: Subject to any disclaimer, the term of this patent is extended or adjusted under 35 U.S.C. 154(b) by 0 days.

(21) Appl. No.: 17/333,005

(22) Filed: May 27, 2021

(65) Prior Publication Data

US 2021/0371822 A1 Dec. 2, 2021

Related U.S. Application Data

(60) Provisional application No. 63/030,592, filed on May 27, 2020.

(51) Int. Cl.
| | |
|---|---|
| *C12N 15/86* | (2006.01) |
| *A61K 40/11* | (2025.01) |
| *A61K 40/31* | (2025.01) |
| *A61K 40/42* | (2025.01) |
| *A61K 40/46* | (2025.01) |
| *A61K 40/50* | (2025.01) |
| *C07K 16/10* | (2006.01) |
| *C12N 5/0783* | (2010.01) |

(52) U.S. Cl.
CPC .............. *C12N 15/86* (2013.01); *A61K 40/11* (2025.01); *A61K 40/31* (2025.01); *A61K 40/4211* (2025.01); *A61K 40/46* (2025.01); *C07K 16/1003* (2023.08); *C12N 5/0636* (2013.01); *C12N 5/0638* (2013.01); *A61K 40/50* (2025.01); *A61K 2239/31* (2023.05); *A61K 2239/38* (2023.05); *A61K 2239/48* (2023.05); *C12N 2501/515* (2013.01); *C12N 2502/1114* (2013.01); *C12N 2502/99* (2013.01); *C12N 2510/00* (2013.01); *C12N 2740/15043* (2013.01)

(58) Field of Classification Search
None
See application file for complete search history.

(56) References Cited

U.S. PATENT DOCUMENTS 7,109,304 B2 9/2006 Hansen et al.

FOREIGN PATENT DOCUMENTS

WO WO-2021232048 A1 * 11/2021 ............. A61K 35/17

OTHER PUBLICATIONS

Hasan et al. A panel of artificial APCs expressing prevalent HLA alleles permits generation of cytotoxic T cells specific for both dominant and subdominant viral epitopes for adoptive therapy. J Immunol. Aug. 15, 2009;183(4):2837-50. (Year: 2009).*
Kluger HM, Dudek AZ, McCann C, Ritacco J, Southard N, Jilaveanu LB, Molinaro A, Sznol M. A phase 2 trial of dasatinib in advanced melanoma. Cancer. May 15, 2011;117(10):2202-8. doi: 10.1002/cncr.25766. Epub Nov. 29, 2010. PMID: 21523734; PMCID: PMC3116034. (Year: 2010).*
Popescu A, Anghel RM. Tyrosine-kinase Inhibitors Treatment in Advanced Malignant Melanoma. Maedica (Bucur). Dec. 2017; 12(4): 293-296. PMID: 29610594; PMCID: PMC5879586. (Year: 2017).*
Guerra N, Lanier LL. Editorial: Emerging Concepts on the NKG2D Receptor-Ligand Axis in Health and Diseases. Front Immunol. Apr. 7, 2020;11:562. doi: 10.3389/fimmu.2020.00562. PMID: 32318064; PMCID: PMC7155425. (Year: 2020).*
Baig, Abdul M., "Neurological Manifestations in COVID-19 Caused by SARS-CoV-2", CNS Neuroscience & Therapeutics, vol. 26, Mar. 14, 2020, pp. 499-501.
Bollard et al., "T Cells for Viral Infections After Allogeneic Hematopoietic Stem Cell Transplant", Blood, vol. 127, No. 26, Jun. 30, 2016, pp. 3331-3340.
Cao et al., "High-Dose Intravenous Immunoglobulin as a Therapeutic Option for Deteriorating Patients With Coronavirus Disease 2019", Open Forum Infectious Diseases, Mar. 19, 2020, pp. 1-6.
Caso et al., "Could SARS-coronavirus-2 Trigger Autoimmune And/or Autoinflammatory Mechanisms In Genetically Predisposed Subjects?", Autoimmunity Reviews, vol. 19, 2020, 3 pages.
Giavridis et al., "CAR T Cell-Induced Cytokine Release Syndrome is Mediated by Macrophages and Abated by IL-1 Blockade", Nature Medicine, vol. 24, No. 6, Jun. 2018, 19 pages.
Hill et al., "CAR-T-and a Side Order of IgG, to Go?—Immunoglobulin Replacement in Patients Receiving CAR-T Cell Therapy", Blood Reviews, vol. 38, Nov. 2019, 25 pages.
Humar et al., "Elevated Serum Cytokines Are Associated With Cytomegalovirus Infection and Disease in Bone Marrow Transplant Recipients", The Journal of Infectious Diseases, vol. 179, No. 2, Feb. 1999, 1 page.
Iannaccone et al., "Weathering the Cytokine Storm in COVID-19: Therapeutic Implications", CardioRenal Medicine, vol. 10, Jun. 29, 2020, 11 pages.

(Continued)

*Primary Examiner* — Allison M Fox
*Assistant Examiner* — Alyssa G Weston
(74) *Attorney, Agent, or Firm* — IPath PLC; Steven J. Miller, Esq.

(57) ABSTRACT

Provided herein are methods for preparing and characterizing SARS-co2 antigen specific immune cell cultures and preparations and methods of using the same in adoptive immunotherapy for cancer, infections and immune disorders. Also, provided are compositions and methods for generating immune cells expressing synthetic antigen binding receptors targeting SARS-cov2 and methods of use of these cells for the treatment and prevention of COVID-19. Also provided are compositions and methods for determining immune response to SARs-cov2 in a subject, detecting SARS-cov2, measuring cytotoxicity induced by SARS-cov2, and detecting the expression and cytotoxicity of synthetic antigen binding receptors targeting SARS-cov2.

18 Claims, No Drawings

Specification includes a Sequence Listing.

(56) References Cited

OTHER PUBLICATIONS

Mclaughlin et al., "Adoptive T Cell Therapy for Epstein-Barr Virus Complications in Patients With Primary Immunodeficiency Disorders", Frontiers in Immunology, vol. 9, No. 556, Mar. 2018, 7 pages.
Moore et al., "Cytokine Release Syndrome in Severe COVID-19", Science, vol. 368, No. 6490, May 1, 2020, pp. 473-474.
Neelapu et al., "Chimeric Antigen Receptor T-cell Therapy—Assessment and Management of Toxicities", Nature Reviews Clinical Oncology, vol. 15, No. 1, Jan. 2018, 37 pages.
Riphagen et al., "Hyperinflammatory Shock in Children During Covid-19 Pandemic", Correspondence, vol. 395, No. 10237, May 23, 2020, pp. 1607-1608.
Rodríguez et al., "Autoinflammatory and Autoimmune Conditions at the Crossroad of COVID-19", Journal of Autoimmunity, vol. 114, 2020, 19 pages.
Shi et al., "Successful Treatment With Plasma Exchange Followed by Intravenous Immunoglobulin in a Critically Ill Patient With COVID-19", International Journal of Antimicrobial Agents, vol. 56, 2020, 5 pages.
Toscano et al., "Guillain-Barré Syndrome Associated With SARS-CoV-2", The New England Journal Of Medicine, Apr. 17, 2020, 3 pages.
Weiss et al., "Clinical Course and Mortality Risk of Severe COVID-19", vol. 395, Mar. 16, 2020, 3 pages.
Zhao et al., "Guillain-Barré Syndrome Associated With SARS-CoV-2 Infection: Causality or Coincidence?", Lancet Neurology, vol. 19, Apr. 1, 2020, pp. 383-384.
Zhou et al., "Clinical and Autoimmune Characteristics of Severe and Critical Cases of COVID-19", Clinical and Translational Science, vol. 13, 2020, pp. 1077-1086.
Zulfiqar et al., "Immune Thrombocytopenia Purpura in a Patient With COVID-19", The New England Journal Of Medicine, Apr. 15, 2020, 2 pages.

\* cited by examiner

METHODS FOR EXPANDING SARS-COV2-ANTIGEN-SPECIFIC T CELLS, COMPOSITIONS AND USES RELATED THERETO

CROSS REFERENCE TO RELATED APPLICATIONS

The application claims priority under 35 U.S.C. § 119 to U.S. Provisional Application Ser. No. 63/030,592, filed May 27, 2020, the disclosures of which are incorporated herein by reference.

TECHNICAL FIELD

The disclosure provides methods for preparing and characterizing SARS-co2 antigen specific immune cell cultures and preparations and methods of using the same in adoptive immunotherapy for cancer, infections and immune disorders.

INCORPORATION BY REFERENCE OF SEQUENCE LISTING

Accompanying this filing is a Sequence Listing entitled "Sequence-Listing_ST25.txt", created on May 27, 2021 and having 3,708,371 bytes of data, machine formatted on IBM-PC, MS-Windows operating system. The sequence listing is hereby incorporated herein by reference in its entirety for all purposes.

BACKGROUND

Adoptive immunotherapy involves implanting or infusing disease-specific and/or engineered T cells, such as antigen-specific cytotoxic cells (CTLs) and synthetic antigen binding receptor (SABR)-expressing T cells, into individuals with the aim of recognizing, targeting, and destroying disease-associated cells.

CARs are synthetic immune-receptors, which can redirect T cells to selectively kill tumor cells. To overcome some of the design limitation of conventional 2nd generation CARs, several alternative designs, collectively termed next generation CARs, have been described, including Ab-TCR (WO 2017/070608 A1 incorporated herein by reference), TCR receptor fusion proteins or TFP (WO 2016/187349 A1 incorporated herein by reference), Synthetic Immune Receptors (SIRS) (see, WO 2018/102795 A1, incorporated herein by reference), Tri-functional T cell antigen coupler (Tri-TAC) (see, WO 2015/117229 A1, incorporated herein by reference) and zSIR (see WO2019232503, incorporated herein by reference). The term SABR as described herein comprise single chain immune receptors (e.g., $1^{st}$, $2^{nd}$ and $3^{rd}$ generation synthetic antigen binding receptors, TFPs, Tri-TAC and the like) and multiple chain immune receptors (e.g., SIR, zSIR, cTCR, ab-TCRs, αβTFP, γdTFP, recombinant TCRs, SAR etc.). SABR are capable of recognizing their target antigen in MHC-dependent and MHC-independent manner. SABRs are synthetic receptors typically consisting of a targeting/binding moiety that is associated with one or more signaling domains in one or more fusion molecules.

The proliferation and persistence of SABR-T cells in vivo is an important factor in treatment efficacy. To this end, we herein describe methods for the generation and/or production of autologous and allogeneic antigen-specific T cells (e.g., T cells specifically sensitized to detect, for example, SARS-cov2-associated antigen(s)), and have also been engineered to express at least one functional synthetic antigen binding receptor directed against a disease-associated antigen of choice.

SUMMARY OF THE INVENTION

Provided herein are methods of generating allogeneic or autologous T cells that express a T cell receptor that specifically binds to an antigen (e.g., a virus antigen such as an SARS-cov2 peptide) presented on a major histocompatibility complex (MHC) and a synthetic antigen binding receptor (SABR) that specifically binds to a target-cell antigen or cell surface marker (e.g., a cancer cell-associated antigen such as CD 19). In some embodiments, the antigen-specific T cells are generated by incubating a sample comprising T cells (responder cells, e.g., a PBMC sample or T cells isolated therefrom) with antigen presenting cells (APCs, i.e., stimulator cells) presenting an antigen (e.g., viral peptide) on an MHC (e.g., a class I MHC encoded by an allele that is present in the subject), thereby inducing proliferation of antigen-specific responder T cells. Preferably, the antigen-specific responder T cells are transduced with a viral vector comprising a nucleic acid sequence encoding a SABR. Also provided herein are methods for inducing ex vivo proliferation of a population of SABR-expressing antigen-specific T cells, comprising culturing a population of isolated T cells with antigen-presenting stimulator cells and transducing the resultant antigen-specific T cells with a viral vector comprising a nucleic acid sequence encoding a SABR. In some embodiments, the transduced T cells are cultured with the antigen-presenting stimulator cells to induce proliferation of antigen-specific SABR T cells. In certain other embodiments, the isolated T cells are transduced with a SABR-encoding viral vector prior to culturing with APCs. In yet further embodiments, the isolated T cells are cultured with APCs prior to and following transduction with a SABR-encoding viral vector.

In some aspects, provided herein are ex vivo methods for enriching central memory T cells. In certain embodiments, such methods comprise obtaining a sample of cells from a subject comprising CD3+ T cells and contacting said CD3+ T cells with antigen-presenting stimulator cells. In preferred embodiments, the CD3+ T cells are isolated from the sample prior to contacting the antigen-presenting stimulator cells by methods known in the art (e.g., positive selection of CD3+ cells from the sample and/or negative selection by depletion of undesired cells or components from the sample). For example, and without limitation, such methods include selection with anti-CD3 beads (e.g., magnetic beads), plastic adherence, elutriation, depletion of NK cells (e.g., using anti-CD56 beads), and/or combinations thereof. In some such embodiments, the CD3+ T cells are transduced with a viral vector encoding a synthetic antigen binding receptor (SABR) before and/or after contact with the antigen-presenting stimulator cells. In some such embodiments the SABR-expressing, CD3+, antigen-specific T cells are cultured with antigen-presenting stimulator cells.

In some embodiments, the stimulator cells are made to present at least one virus peptide antigen by incubating the intended stimulator cells with one or more of the virus peptides. In some embodiments, the virus is SARS-cov2.

The disclosure also provides isolated nucleic acids, polypeptides and vectors encoding SABR, wherein the antigen specific domain of the SABR targets the spike glycoprotein of SARS-cov2. The disclosure also provides cells and cell populations (such as T cells, NK cells, iPSC) comprising vectors encoding nucleic acids encoding SABR, wherein the antigen specific domain of the SABR targets spike glycoprotein of SARS-cov2.

The disclosure also provides isolated nucleic acids, isolated polypeptides, vectors and kits for a fast, economical, sensitive and specific assay for detection of antibodies, antibody fragments and non-immunoglobulin antigen binding domains targeting the Spike glycoprotein of SARS-cov2.

DETAILED DESCRIPTION

Definitions

For convenience, certain terms employed in the specification, examples, and appended claims are collected here.

The term "antigen" or "Ag" refers to a molecule that provokes an immune response. This immune response may involve either antibody production, or the activation of specific immunologically-competent cells, or both.

The term "antigen presenting cell" or "APC" refers to an immune system cell such as an accessory cell (e.g., a B-cell, a dendritic cell, and the like) that displays a foreign antigen complexed with major histocompatibility complexes (WIC's) on its surface.

An "antigen binding domain" or "antigen binding module" or "antigen binding segment" or "antigen specific domain" (ASD) refers to a polypeptide or peptide that due to its primary, secondary or tertiary sequence, post-translational modifications and/or charge binds to an antigen with a high degree of specificity.

The term "Ab-TCR" or "AbTCR" refers to a next generation CAR platform as described in WO 2017/070608 A1 which is incorporated herein by reference.

The term "accessory module" refers to any molecule that is expressed in an immune cell (e.g., T cell, e.g., SABR-T cell, e.g., CAR-T cell or TCR-T cell) to decrease, regulate or modify the activity of the immune cell.

As used herein, the term "backbone" or "architecture" refers to the configuration of the different components (e.g., antigen binding domains, hinge domains, transmembrane domains, signaling domains) that comprise different SABR (e.g., CAR, SIR, cTCR, Ab-TCR, TFP etc.) and any accessory module which is generally optional.

Table A1: Exemplary SABR architectures. First generation conventional CARs (Conventional CAR I) have an intracellular signaling (ISD) domain (e.g. CD3z) and no costimulatory domain. The TCR fusion proteins (TFP) are another example of conventional CAR 1. Second generation conventional CARs (Conventional CAR 2 or CAR II) have one costimulatory domain (e.g. 41BB or CD28) and an intracellular signaling (ISD) domain (e.g. CD3z). Third generation conventional CARs (Conventional CAR 3 or CAR III) have two costimulatory domains (e.g. 41BB and CD28) and an intracellular signaling (ISD) domain (e.g. CD3z). Ab-TCRs are duel chain receptors incorporating a vL-linker-TCR domain (TCRD and a vH-linker-TCR domain (TCRD) and have been described in PCT/US2016/058305. cTCRs are single chain, one-and-half, or double chain receptors consisting of antigen binding domain derived from a vL and vH fragment that are fused to one or more TCR constant chain (TCR-C) and result in activation of T cell signaling. Exemplary configurations of cTCR are described in PCT/US2017/064379 or WO 2018/102795 A1. Synthetic immune receptors are next generation SABR and are described in PCT/US2017/064379 or WO 2018/102795 A1. zSIRs are double chain receptors comprising two CD3z chains or fragments thereof with optional linkers and are described in PCT/US2019/035096. SABR may target a single antigen, two antigens or multiple antigens. SABR may target the single epitope of a single antigen or two or more epitopes of one or more antigens. The present disclosure covers unispecific, bispecific, multispecific, uni-paratopic, bi-paratopic and multi-paratopic SABRs.

TABLE A1

Exemplary SABR Architectures

| | | | | | | |
|---|---|---|---|---|---|---|
| 1 | CAR 1 or CAR I (including TFP) | ASD | HR | TMD | ISD | |
| 2 | CAR 2 (CAR II) | ASD | HR | TMD | CSD | ISD |
| 3 | CAR 3 (CAR III) | ASD | HR | TMD | CSD-I | CSD-II | ISD |
| 4 | Ab-TCR | vL-cL | TCRD(1) | 2A | vH-CH1 | TCRD (II) |
| 5 | Double Chain cTCR/SIR-1 | vL | TCR-C(1) | 2A | vH | TCR-C (II) |
| 6 | Double Chain zSIR | vL-linker | CD3z | 2A | vH-linker | CD3z |
| 6 | One & Half Chain cTCR/SIR-3 | | TCR-C(1) | 2A | ASD | TCR-C (II) |

TABLE 1

| SEQ ID NO | Name of vector or component | SEQ ID NO | |
|---|---|---|---|
| 1 | pLenti-EF1a | 11 | pLENTI-NLuc-AcV5-Blasticidin-Pa08 |
| 2 | pLenti-EF1a-DWPRE | 12 | pLENTI-Gluc-Flag-blast-B07 |
| 3 | MSCV-Bgl2-AvrII-Bam-EcoR1-Xho-BstB1-Mlu-Sal-ClaI.I03 | 13 | PolyA |
| 4 | pCCLc-MNDU3-WPRE | 14 | PolyA |
| 5 | pCCLc-MNDU3-Eco-Nhe-Sal-WPRE | 15 | PolyA |
| 6 | pCCLc-MNDU3-delta-WPRE | 16 | polyA |
| 7 | EF1alpha_(EF1a)_Promoter_Variant | 17 | pCDNA3 |

TABLE 1-continued

| SEQ ID NO | Name of vector or component | SEQ ID NO | |
|---|---|---|---|
| 8 | pSBbi-Pur | 18 | DNA barcode 11 |
| 9 | MSCVhygro-GLuc-HA-G02 | 19 | DNA barcode 12 |
| 10 | MSCVpac-GLUC-R03 | 20 | DNA barcode 13 |

TABLE 2

| NAME | SEQ ID NO (DNA) | SEQ ID NO (PRT) |
|---|---|---|
| LucPPe-146-1H2 | 21 | 491 |
| LucPPe-133-1B2 | 22 | 492 |
| LucPPe-78-0B10 | 23 | 493 |
| LucPPe49-7C6A | 24 | 494 |
| LucPpL-81-6G1 | 25 | 495 |
| GLuc | 26 | 496 |
| NLuc | 27 | 497 |
| TLuc | 28 | 498 |
| MLuc7-M43L/M110L | 29 | 499 |
| LoLuc | 30 | 500 |
| HtLuc | 31 | 501 |
| PaLuc1 | 32 | 502 |
| PaLuc2 | 33 | 503 |
| MpLuc1 | 34 | 504 |
| McLuc1 | 35 | 505 |
| MaLuc1 | 36 | 506 |
| MoLuc1 | 37 | 507 |
| MoLuc2 | 38 | 508 |
| MLuc39 | 39 | 509 |
| PsLuc1 | 40 | 510 |
| LoLuc1-3 | 41 | 511 |
| HtLuc2 | 42 | 512 |
| Renilla-Luc | 43 | 513 |

TABLE 3

| NAME | SEQ ID NO (DNA) | SEQ ID NO (PRT) |
|---|---|---|
| CD8_Signal_Peptide | 45 | 515 |
| CD8-SIGNAL-PEPTIDE | 46 | 516 |
| IgH_Signal_Peptide | 47 | 517 |
| IgH_Signal_Peptide | 48 | 518 |
| (GGGGS)x3-Linker | 56 | 526 |
| (GGSG)7_Linker | 57 | 527 |
| (GGSG)7_Linker_2 | 58 | 528 |
| DDAKK_linker | 59 | 529 |

TABLE 4

Exemplary Tags and Linkers

| Name of fragment | SEQ ID NO (DNA) | SEQ ID NO (PRT) |
|---|---|---|
| G4S | 61 | 531 |
| G3Sx2 | 62 | 532 |
| G4Sx2 | 63 | 533 |
| G4Sx3 | 64 | 534 |
| Myc-(P)-TAG | 65 | 535 |
| MYC2-TAG | 66 | 536 |
| MYC4-TAG | 67 | 537 |
| V5-TAG | 68 | 538 |

TABLE 5

Exemplary SABR components

| Name of fragment | SEQ ID NO (DNA) | SEQ ID NO (PRT) |
|---|---|---|
| hTCR-alpha-constant_X02883.1 | 78 | 548 |
| hTCRa-WT | 79 | 549 |
| hTCRa-CSDVP | 80 | 550 |
| hTCRa-opt2 | 81 | 551 |
| hTCRa-opt3 | 82 | 552 |
| hTCRa-T48C-opt | 83 | 553 |
| hTCRa-T48C-opt1 | 84 | 554 |
| hTCRa-SDVP | 85 | 555 |
| hTCRa-S61R | 86 | 556 |
| hTCRa-SDVPR | 87 | 557 |
| hTCRa-SD | 88 | 558 |
| hTCRaECD-CD3zECDTMCP-opt2 | 89 | 559 |
| mTCRa-opt | 90 | 560 |
| cTCRa-opt | 91 | 561 |
| hTCR-b1-constant-region_X00437.1 | 92 | 562 |
| hTCR-b2-constant-region_L34740 | 93 | 563 |
| hTCRb-WT | 94 | 564 |
| hTCRb-S57C-opt1 | 95 | 565 |
| hTCRb-KACIAH | 96 | 566 |
| 41BB-CP-opt2 | 134 | 604 |
| CD3zECDTM-28z-opt | 135 | 605 |
| CD3zECDTM-BBz-opt | 136 | 606 |
| CD3zECDTM-28z-opt2 | 137 | 607 |
| CD3zECDTM-BBz-opt2 | 138 | 608 |
| TCRa-wt2-opt-6MD | 139 | 609 |
| TCRb-wt2-opt-6MD | 140 | 610 |
| TCRg-6MD | 141 | 611 |
| TCRd-6MD | 142 | 612 |
| IgCL | 143 | 613 |
| IgG1-CH1 | 144 | 614 |
| IgG1-CH1-DeltaC | 145 | 615 |
| IgG1-CH1-Hinge | 146 | 616 |
| IgG1-CH1-v2 | 147 | 617 |
| IgG1-CH1-DeltaC-v2 | 148 | 618 |
| IgG1-CH1-Hinge-v2 | 149 | 619 |
| IgG2-0C-CH1 | 150 | 620 |
| IgG2-IC-CHI1 | 151 | 621 |
| IgG3-CHI1 | 152 | 622 |

TABLE 6

Therapeutic Controls

| Name of fragment | SEQ ID NO (DNA) | SEQ ID NO (PRT) |
|---|---|---|
| PuroR_Variant-(PAC) | 190 | 660 |
| BlastR | 191 | 661 |
| CNB30 | 192 | 662 |
| GMCSF-SP-tEGFR | 193 | 663 |
| tEGFRviii | 194 | 664 |
| tCD19 | 195 | 665 |
| tBCMA | 196 | 666 |
| K13 | 197 | 667 |
| MC159 | 198 | 668 |
| K13-opt | 199 | 669 |
| icaspase-9 | 200 | 670 |

TABLE 7A

| SARS-cov2 vL, vH and ScFv | | | | | |
|---|---|---|---|---|---|
| Name of fragment | SEQ ID NO (DNA) | SEQ ID NO (PRT) | CDR1 | CDR2 | CDR3 |
| SARS-cov2-vL | | | | | |
| SARScov2-CR3022-vL | 213 | 683 | 960 | 961 | 962 |
| SARScov2-S-RBD-B38-vL | 214 | 684 | 963 | 964 | 965 |
| SARS-cov2-S-RBD-H4-vL | 215 | 685 | 966 | 967 | 968 |
| SARS-cov2-vH | | | | | |
| SARScov2-CR3022-vH | 217 | 687 | 970 | 971 | 972 |
| SARScov2-S-RBD-B38-vH | 218 | 688 | 973 | 974 | 975 |
| SARS-cov2-S-RBD-H4-vH | 219 | 689 | 976 | 977 | 978 |
| SARS-cov2-scFv | | | | | |
| SARScov2-CR3022-scFv | 221 | 691 | | | |
| SARScov2-S-RBD-B38-scFv | 222 | 692 | | | |
| SARS-cov2-S-RBD-H4-scFv | 223 | 693 | | | |

TABLE 7B

| SARS-cov2 | | |
|---|---|---|
| Name of fragment | SEQ ID NO (DNA) | SEQ ID NO (PRT) |
| SARS-cov2-Poly-epitopes and Polypeptides | | |
| SARS-cov2-Spike-Glycoprotein-S2 | 224 | 694 |
| SARScov2-HLA-A0201-Polypeptides | 225 | 695 |
| Ub-G76A-SARScov2-HLA-A0201-Polyepitopes | 226 | 696 |
| SARScov2-HLA-DRB10401-Polyepitopes | 227 | 697 |
| Ub-G76A-SARScov2-HLA-DRB10401-Polyepitopes | 228 | 698 |
| CD8SP-StreptagII-R1-S-Protein-RBD-Mlu-mCD8-hinge-TM | 229 | 699 |
| SARS-cov2 and Relevant Cellular Proteins | | |
| SARS-cov2-Spike-Glycoprotein-1-RBD (S1-RBD) | 230 | 700 |
| SARS-cov2-Spike-Glycoprotein | 231 | 701 |
| SARS-cov2-nucleocapside-phosphoprotein | 232 | 702 |
| SARS-cov2-membrane-glycoprotein | 233 | 703 |
| orf3a | 234 | 704 |
| ACE2 | 235 | 705 |
| TMPRSS2 | 236 | 706 |
| SARS-cov2-Spike-Glycoprotein-S1-ND1 | 237 | 707 |
| SARS-cov2-Spike-Glycoprotein-S1-ND2 | 242 | 712 |
| SARS-cov2-Spike-Glycoprotein-S2 | 224 | 694 |
| MALIBU-Glo Reagents | | |
| CD8SP-hu-mROO5-1-(vL-vH)-GGSG-NLuc-4xFLAG-x2STREP-8xHis-T2A-PAC | 238 | 708 |
| CD8SP-SARScov2-CR3022-(vL-vH)-GGSG-NLuc-4xFLAG-x2STREP-8xHis-T2A-PAC | 239 | 709 |
| CD8SP-SARS-cov2-S-RBD-H4-(vL-vH)-GGSG-NLuc-4xFLAG-x2STREP-8xHis-T2A-PAC | 240 | 710 |
| CD8SP-SARScov2-S-RBD-B38-(vL-vH)-GGSG-NLuc-4xFLAG-x2STREP-8xHis-T2A-PAC | 241 | 711 |
| Topanga Reagents | | |
| CD19-ECD-GGSG-NLuc-4xFlag-2xStreptag-8xHis-T2A-Pac | 243 | 713 |
| CD33-ECD-GGSG-NLuc-4xFlag-2xStreptag-8xHis-T2A-Pac | 244 | 714 |
| CD8SP-BCMA-ECD-GGSG-NLuc-4xFlag-2xStreptag-8xHis-T2A-Pac | 245 | 715 |
| CD8SP-StreptagII-R1-S1-Protein-RBD-ECD-GGSG-NLuc-4xFlag-2xStreptag-8xHis-T2A-Pac | 246 | 716 |
| CD8SP-R1-S1-Protein-RBD-ECD-GGSG-NLuc-4xFlag-2xStreptag-8xHis-T2A-Pac | 247 | 717 |
| S-Protein-ECD-GGSG-NLuc-4xFlag-2xStreptag-8xHis | 248 | 718 |
| SARS-cov2-nucleocapsid-GGS-NLuc-4xFlag-2xStreptag-8xHis-T2A-PAC | 249 | 719 |
| orf3a-GGSG-NLuc-4xFlag-2xStreptag-8xHis | 250 | 720 |
| ACE2-ECD-GGS-NLuc-4xFlag-2xStreptag-8xHis | 251 | 721 |

TABLE 8

Exemplary SABR Targeting CD19

| Name of fragment | SEQ ID NO (DNA) | SEQ ID NO (PRT) |
|---|---|---|
| CD8SP-hu-mROO5-1-vL-Gly-Ser-Linker-hu-mROO5-1-vH-Myc-CD8TM-BBz-T2A-PAC | 253 | 723 |
| CD8SP-hu-mROO5-1-vL-Gly-Ser-Linker-hu-mROO5-1-vH-Myc-28z-T2A-PAC | 254 | 724 |
| CD8SP-hu-mROO5-1-vL-Gly-Ser-Linker-hu-mROO5-1-vH-Myc-28z | 255 | 725 |
| CD8SP-hu-mROO5-1-vL-Gly-Ser-Linker-hu-mROO5-1-vH-Myc-CD8TM-BBz | 256 | 726 |
| CD8SP-hu-mROO5-1-vH-Gly-Ser-Linker-vL-Myc-CD8TM-BBz | 257 | 727 |
| CD8SP-hu-mROO5-1-vL-Gly-Ser-Linker-hu-mROO5-1-vH-Myc-CD8TM-z-P2A-K13-FLAG-T2A-PAC | 258 | 728 |
| CD8SP-hu-mROO5-1-vL-[hTCRa-CSDVP]-F-F2A-SP-hu-mROO5-1-vH-[hTCRb-KACIAH]-F-P2A-PAC | 259 | 729 |
| CD8SP-hu-mROO5-1-vL-[hTCRb-KACIAH]-F-F2A-SP-hu-mROO5-1-vH-[hTCRa-CSDVP]-F-P2A-PAC | 260 | 730 |
| CD8SP-hu-mROO5-1-vL-[hTCRb-S57C]-F-F2A-SP-hu-mROO5-1-vH-[hTCRa-T48C] | 261 | 731 |
| CD8SP-hu-mROO5-1-vL-[hTCRb-S57C]-F-F2A-SP-hu-mROO5-1-vH-[hTCRa-T48C]-F-F2A-K13-opt | 262 | 732 |
| CD8SP-hu-mROO5-1-vL-[hTCRa-T48C]-F-F2A-SP-hu-mROO5-1-vH-[hTCRb-S57C] | 263 | 733 |
| CD8SP-hu-mROO5-1-vL-[hTCRa-T48C]-F-F2A-SP-hu-mROO5-1-vH-[hTCRb-S57C]-F-P2A-K13-opt | 264 | 734 |
| CD8SP-V5-[hTCRb-KACIAH]-F-P2A-CD8SP-hu-mROO5-1-vL-Gly-Ser-Linker-hu-mROO5-1-vH-Myc-[hTCRa-CSDVP]-F-F2A-PAC | 265 | 735 |
| CD8SP-MYC-[hTCRa-T48C-opt1]-F-F2A-SP-hu-mROO5-1-vL-Gly-Ser-Linker-hu-mROO5-1-vH-V5-[hTCRb-S57C-opt1]-F-P2A-PAC | 266 | 736 |
| CD8SP-hu-mROO5-1-vL-[hTCRb-opt2]-F-P2A-SP-hu-mROO5-1-vH-[hTCRa-opt2]-F-F2A-PAC | 267 | 737 |
| CD8SP-hu-mROO5-1-vL-[hTCRb-opt2]-F-P2A-SP-hu-mROO5-1-vH-Myc-[preTCRa-Del48]-F-F2A-PAC | 268 | 738 |
| CD8SP-[hTCRb-opt2]-F-P2A-CD8SP-hu-mROO5-1-vL-Gly-Ser-Linker-hu-mROO5-1-vH-Myc4-[preTCRa-Del48]-F-F2A-PAC | 269 | 739 |
| CD8SP-hu-mROO5-1-vL-V5-[hTCRg1-opt]-F-P2A-SP-hu-mROO5-1-vH-Myc-[hTCRd-opt]-F-P2A-PAC | 270 | 740 |
| CD8SP-hu-mROO5-1-vL-[hTCRd-opt]-F-P2A-SP-hu-mROO5-1-vH-[hTCRg1-opt] | 271 | 741 |
| CD8SP-V5-[hTCRg1-opt]-F-P2A-CD8SP-hu-mROO5-1-vL-Gly-Ser-Linker-hu-mROO5-1-vH-Myc-[hTCRd-opt]-F-P2A-PAC | 272 | 742 |
| CD8SP-hu-mROO5-1-vL-IgCL-Bam-CD3zECDTMCP-opt-F-P2A-Spe-SP-Bst-hu-mROO5-1-vH-IgG1-CH1-KPN-CD3zECDTMCP-opt2-F-F2A-Xba-PAC | 273 | 743 |
| CD8SP-hu-mROO5-1-vL-[hTCRbECD-Bam-CD3zECDTMCP-opt]-F-P2A-SP-hu-mROO5-1-vH-[hTCRaECD-Kpn-CD3zECDTMCP-opt2] | 274 | 744 |
| CD8SP-hu-mROO5-1-vL-[hTCRb-KAC-ECD-Bam-CD3zECDTMCP-opt]-F-P2A-SP-hu-mROO5-1-vH-[hTCRa-CSDVP-ECD-Kpn-CD3zECDTMCP-opt2] | 275 | 745 |
| CD8SP-hu-mROO5-1-vL-V5-[hTCRbECD-Bam-CD3zECDTMCP-opt]-F-P2A-SP-hu-mROO5-1-vH-Myc-[hTCRaECD-Kpn-CD3zECDTM-28z-opt2] | 276 | 746 |
| CD8SP-hu-mROO5-1-vL-V5-[hTCRbECD-Bam-CD3zECDTM-28z-opt]-F-P2A-SP-hu-mROO5-1-vH-Myc-[hTCRaECD-Kpn-CD3zECDTM-28z-opt2] | 277 | 747 |
| CD8SP-hu-mROO5-1-vL-V5-[hTCRbECD-Bam-CD3zECDTMCP-opt]-F-P2A-SP-hu-mROO5-1-vH-Myc4-[hTCRaECD-Kpn-CD3zECDTM-BBz-opt2] | 278 | 748 |
| CD8SP-hu-mROO5-1-vL-V5-[hTCRbECD-Bam-CD3zECDTM-BBz-opt]-F-P2A-SP-hu-mROO5-1-vH-Myc4-[hTCRaECD-Kpn-CD3zECDTM-BBz-opt2] | 279 | 749 |
| CD8SP-hu-mROO5-1-vL-CD3zECDTMCP-opt-F-P2A-Spe-SP-Bst-hu-mROO5-1-vH-Mlu-CD3zECDTMCP-opt2-F-F2A-PAC | 280 | 750 |
| CD8SP-hu-mROO5-1-vL-[IgCL-TCRg-6MD]-F-P2A-SP-hu-mROO5-1-vH-[IgG1-CH1-TCRd-6MD] | 281 | 751 |
| CD8SP-hu-mROO5-1-vL-[IgCL-TCRb-IAH-6MD]-F-P2A-SP-hu-mROO5-1-vH-[IgG1-CH1-TCRa-SDVP-6MD] | 282 | 752 |
| CD8SP-hu-mROO5-1-vL-[IgCL-TCRb-wt-opt2-6MD]-F-P2A-SP-hu-mROO5-1-vH-[IgG1-CH1-TCRa-wt-op2-6MD] | 283 | 753 |
| CD8SP-hu-mROO5-1-(vL-vH)-CD3e-ECDTMCP-opt2 | 284 | 754 |
| CD8SP-hu-mROO5-1-(vL-vH)-CD3d-ECDTMCP-opt2 | 285 | 755 |
| CD8SP-hu-mROO5-1-(vL-vH)-CD3g-ECDTMCP-opt2 | 286 | 756 |
| CD8SP-hu-mROO5-1-(vL-vH)-CD3z-ECDTMCP-opt2 | 287 | 757 |
| CD8SP-hu-mROO5-1-(vH-vL)-CD3e-ECDTMCP-opt2 | 288 | 758 |
| CD8SP-hu-mROO5-1-(vH-vL)-CD3d-ECDTMCP-opt2 | 289 | 759 |
| CD8SP-hu-mROO5-1-(vH-vL)-CD3g-ECDTMCP-opt2 | 290 | 760 |
| CD8SP-hu-mROO5-1-(vH-vL)-CD3z-ECDTMCP-opt2 | 291 | 761 |
| CD8SP-hu-mROO5-1-vL-Gly-Ser-Linker-hu-mROO5-1-vH-[hTCRa-opt2]-F-F2A-PAC | 292 | 762 |

TABLE 8-continued

Exemplary SABR Targeting CD19

| Name of fragment | SEQ ID NO (DNA) | SEQ ID NO (PRT) |
|---|---|---|
| CD8SP-hu-mROO5-1-vL-Gly-Ser-Linker-hu-mROO5-1-vH-[hTCRb-opt2]-F-F2A-PAC | 293 | 763 |
| CD8SP-hu-mROO5-1-vL-Gly-Ser-Linker-hu-mROO5-1-vH-Myc4-[preTCRa-Del48]-F-F2A-PAC | 294 | 764 |
| CD8SP-hu-mROO5-1-vL-[hTCRb-opt2]-F-P2A-PAC | 295 | 765 |
| CD8SP-hu-mROO5-1-vL-[hTCRb-opt2] | 296 | 766 |
| IgHSP-hu-mROO5-1-vH-[hTCRa-opt2]-F-F2A-BlastR | 297 | 767 |
| IgHSP-hu-mROO5-1-vH-[hTCRa-opt2] | 298 | 768 |
| CD8SP-hu-mROO5-1-vL-V5-[hTCRb-S57C-opt]-F-P2A-PAC | 299 | 769 |
| CD8SP-hu-mROO5-1-vL-V5-[hTCRb-S57C-opt] | 300 | 770 |
| IgHSP-hu-mROO5-1-vH-Myc-[hTCRa-T48C-opt]-F-F2A-BlastR | 301 | 771 |
| IgHSP-hu-mROO5-1-vH-Myc-[hTCRa-T48C-opt] | 302 | 772 |
| CD8SP-hu-mROO5-1-vL-Gly-Ser-Linker-hu-mROO5-1-vH-[hTCRa-SDVP]-F-F2A-PAC | 303 | 773 |
| CD8SP-hu-mROO5-1-vL-Gly-Ser-Linker-hu-mROO5-1-vH-[hTCRb-KAIAH]-F-P2A-PAC | 304 | 774 |
| CD8SP-hu-mROO5-1-(vL-vH)-G4S-CD3e-ECDTMCP-opt2-F-F2A-PAC | 305 | 775 |
| CD8SP-hu-mROO5-1-(vL-vH)-G4S-CD3d-ECDTMCP-opt2-F-F2A-PAC | 306 | 776 |
| CD8SP-hu-mROO5-1-(vL-vH)-G4S-CD3g-ECDTMCP-opt2-F-F2A-PAC | 307 | 777 |
| CD8SP-hu-mROO5-1-(vL-vH)-G4S-CD3z-ECDTMCP-opt2-F-F2A-PAC | 308 | 778 |

TABLE 9

Exemplary SABR Targeting SARS-cov2 S-RBD

| Name of fragment | SEQ ID NO (DNA) | SEQ ID NO (PRT) |
|---|---|---|
| CD8SP-SARScov2-CR3022-vL-GS-linker-SARScov2-CR3022-vH-CD8TM-BBz | 309 | 779 |
| CD8SP-SARScov2-CR3022-vL-GS-linker-SARScov2-CR3022-vH-Myc-CD8TM-BBz-T2A-PAC | 310 | 780 |
| CD8SP-SARScov2-CR3022-vL-GS-linker-SARScov2-CR3022-vH-Myc-28z-T2A-PAC | 311 | 781 |
| CD8SP-SARScov2-CR3022-vL-GS-linker-SARScov2-CR3022-vH-Myc-28z | 312 | 782 |
| CD8SP-SARScov2-CR3022-vL-GS-linker-SARScov2-CR3022-vH-Myc-CD8TM-BBz | 313 | 783 |
| CD8SP-SARScov2-CR3022-vH-GS-linker-vL-Myc-CD8TM-BBz | 314 | 784 |
| CD8SP-SARScov2-CR3022-vL-GS-linker-SARScov2-CR3022-vH-Myc-CD8TM-z-P2A-K13-FLAG-T2A-PAC | 315 | 785 |
| CD8SP-SARScov2-CR3022-vL-[hTCRa-CSDVP]-F-F2A-SP-SARScov2-CR3022-vH-[hTCRb-KACIAH]-F-P2A-PAC | 316 | 786 |
| CD8SP-SARScov2-CR3022-vL-[hTCRb-KACIAH]-F-F2A-SP-SARScov2-CR3022-vH-[hTCRa-CSDVP]-F-P2A-PAC | 317 | 787 |
| CD8SP-SARScov2-CR3022-vL-[hTCRb-S57C]-F-F2A-SP-SARScov2-CR3022-vH-[hTCRa-T48C] | 318 | 788 |
| CD8SP-SARScov2-CR3022-vL-[hTCRb-S57C]-F-F2A-SP-SARScov2-CR3022-vH-[hTCRa-T48C]-F-F2A-K13-opt | 319 | 789 |
| CD8SP-SARScov2-CR3022-vL-[hTCRa-T48C]-F-F2A-SP-SARScov2-CR3022-vH-[hTCRb-S57C] | 320 | 790 |
| CD8SP-SARScov2-CR3022-vL-[hTCRa-T48C]-F-F2A-SP-SARScov2-CR3022-vH-[hTCRb-S57C]-F-P2A-K13-opt | 321 | 791 |
| CD8SP-V5-[hTCRb-KACIAH]-F-P2A-CD8SP-SARScov2-CR3022-vL-GS-linker-SARScov2-CR3022-vH-Myc-[hTCRa-CSDVP]-F-F2A-PAC | 322 | 792 |
| CD8SP-MYC-[hTCRa-T48C-opt1]-F-F2A-SP-SARScov2-CR3022-vL-GS-linker-SARScov2-CR3022-vH-V5-[hTCRb-S57C-opt1]-F-P2A-PAC | 323 | 793 |
| CD8SP-SARScov2-CR3022-vL-[hTCRb-opt2]-F-P2A-SP-SARScov2-CR3022-vH-[hTCRa-opt2]-F-F2A-PAC | 324 | 794 |
| CD8SP-SARScov2-CR3022-vL-[hTCRb-opt2]-F-P2A-SP-SARScov2-CR3022-vH-Myc-[preTCRa-Del48]-F-F2A-PAC | 325 | 795 |
| CD8SP-[hTCRb-opt2]-F-P2A-CD8SP-SARscov2-CR3022-vL-GS-linker-SARScov2-CR3022-vH-Myc4-[preTCRa-Del48]-F-F2A-PAC | 326 | 796 |
| CD8SP-SARScov2-CR3022-vL-V5-[hTCRg1-opt]-F-P2A-SP-SARScov2-CR3022-vH-Myc-[hTCRd-opt]-F-F2A-PAC | 327 | 797 |
| CD8SP-SARScov2-CR3022-vL-[hTCRd-opt]-F-P2A-SP-SARScov2-CR3022-vH-[hTCRg1-opt] | 328 | 798 |
| CD8SP-V5-[hTCRg1-opt]-F-P2A-CD8SP-SARScov2-CR3022-vL-GS-linker-SARScov2-CR3022-vH-Myc-[hTCRd-opt]-F-F2A-PAC | 329 | 799 |

TABLE 9-continued

Exemplary SABR Targeting SARS-cov2 S-RBD

| Name of fragment | SEQ ID NO (DNA) | SEQ ID NO (PRT) |
|---|---|---|
| CD8SP-SARScov2-CR3022-vL-IgCL-Bam-CD3zECDTMCP-opt-F-P2A-Spe-SP-Bst-SARScov2-CR3022-vH-IgG1-CH1-KPN-CD3zECDTMCP-opt2-F-F2A-Xba-PAC | 330 | 800 |
| CD8SP-SARScov2-CR3022-vL-[hTCRbECD-Bam-CD3zECDTMCP-opt]-F-P2A-SP-SARScov2-CR3022-vH-[hTCRaECD-Kpn-CD3zECDTMCP-opt2] | 331 | 801 |
| CD8SP-SARScov2-CR3022-vL-[hTCRb-KAC-ECD-Bam-CD3zECDTMCP-opt]-F-P2A-SP-SARScov2-CR3022-vH-[hTCRa-CSDVP-ECD-Kpn-CD3zECDTMCP-opt2] | 332 | 802 |
| CD8SP-SARScov2-CR3022-vL-V5-[hTCRbECD-Bam-CD3zECDTMCP-opt]-F-P2A-SP-SARScov2-CR3022-vH-Myc-[hTCRaECD-Kpn-CD3zECDTM-28z-opt2] | 333 | 803 |
| CD8SP-SARScov2-CR3022-vL-V5-[hTCRbECD-Bam-CD3zECDTM-28z-opt]-F-P2A-SP-SARScov2-CR3022-vH-Myc-[hTCRaECD-Kpn-CD3zECDTM-28z-opt2] | 334 | 804 |
| CD8SP-SARScov2-CR3022-vL-V5-[hTCRbECD-Bam-CD3zECDTMCP-opt]-F-P2A-SP-SARScov2-CR3022-vH-Myc4-[hTCRaECD-Kpn-CD3zECDTM-BBz-opt2] | 335 | 805 |
| CD8SP-SARScov2-CR3022-vL-V5-[hTCRbECD-Bam-CD3zECDTM-BBz-opt]-F-P2A-SP-SARScov2-CR3022-vH-Myc4-[hTCRaECD-Kpn-CD3zECDTM-BBz-opt2] | 336 | 806 |
| CD8SP-SARScov2-CR3022-vL-CD3zECDTMCP-opt-F-P2A-Spe-SP-Bst-SARSv2-CR3022-vH-Mlu-CD3zECDTMCP-opt2-F-F2A-PAC | 337 | 807 |
| CD8SP-SARScov2-CR3022-vL-[IgCL-TCRg-6MD]-F-P2A-SP-SARScov2-CR3022-vH-[IgG1-CH1-TCRd-6MD] | 338 | 808 |
| CD8SP-SARScov2-CR3022-vL-[IgCL-TCRb-IAH-6MD]-F-P2A-SP-SARScov2-CR3022-vH-[IgG1-CH1-TCRa-SDVP-6MD] | 339 | 809 |
| CD8SP-SARScov2-CR3022-vL-[IgCL-TCRb-wt-opt2-6MD]-F-P2A-SP-SARScov2-CR3022-vH-[IgG1-CH1-TCRa-wt-op2-6MD] | 340 | 810 |
| CD8SP-SARScov2-CR3022-(vL-vH)-CD3e-ECDTMCP-opt2 | 341 | 811 |
| CD8SP-SARScov2-CR3022-(vL-vH)-CD3d-ECDTMCP-opt2 | 342 | 812 |
| CD8SP-SARScov2-CR3022-(vL-vH)-CD3g-ECDTMCP-opt2 | 343 | 813 |
| CD8SP-SARScov2-CR3022-(vL-vH)-CD3z-ECDTMCP-opt2 | 344 | 814 |
| CD8SP-SARScov2-CR3022-(vH-vL)-CD3e-ECDTMCP-opt2 | 345 | 815 |
| CD8SP-SARScov2-CR3022-(vH-vL)-CD3d-ECDTMCP-opt2 | 346 | 816 |
| CD8SP-SARScov2-CR3022-(vH-vL)-CD3g-ECDTMCP-opt2 | 347 | 817 |
| CD8SP-SARScov2-CR3022-(vH-vL)-CD3z-ECDTMCP-opt2 | 348 | 818 |
| CD8SP-SARScov2-CR3022-vL-GS-linker-SARScov2-CR3022-vH-[hTCRa-opt2]-F-F2A-PAC | 349 | 819 |
| CD8SP-SARScov2-CR3022-vL-GS-linker-SARScov2-CR3022-vH-[hTCRP-opt2]-F-F2A-PAC | 350 | 820 |
| CD8SP-SARScov2-CR3022-vL-GS-linker-SARScov2-CR3022-vH-Myc4-[preTCRa-Del48]-F-F2A-PAC | 351 | 821 |
| CD8SP-SARScov2-CR3022-vL-[hTCRb-opt2]-F-P2A-PAC | 352 | 822 |
| CD8SP-SARScov2-CR3022-vL-[hTCRb-opt2] | 353 | 823 |
| IgHSP-SARScov2-CR3022-vH-[hTCRa-opt2]-F-F2A-BlastR | 354 | 824 |
| IgHSP-SARScov2-CR3022-vH-[hTCRa-opt2] | 355 | 825 |
| CD8SP-SARScov2-CR3022-vL-V5-[hTCRP-S57C-opt]-F-P2A-PAC | 356 | 826 |
| CD8SP-SARScov2-CR3022-vL-V5-[hTCRP-S57C-opt] | 357 | 827 |
| IgHSP-SARScov2-CR3022-vH-Myc-[hTCRa-T48C-opt]-F-F2A-BlastR | 358 | 828 |
| IgHSP-SARScov2-CR3022-vH-Myc-[hTCRa-T48C-opt] | 359 | 829 |
| CD8SP-SARScov2-CR3022-vL-GS-linker-SARScov2-CR3022-vH-[hTCRa-SDVP]-F-F2A-PAC | 360 | 830 |
| CD8SP-SARScov2-CR3022-vL-GS-linker-SARScov2-CR3022-vH-[hTCRP-KAIAH]-F-P2A-PAC | 361 | 831 |
| CD8SP-SARScov2-CR3022-(vL-vH)-G4S-CD3e-ECDTMCP-opt2-F-F2A-PAC | 362 | 832 |
| CD8SP-SARScov2-CR3022-(vL-vH)-G4S-CD3d-ECDTMCP-opt2-F-F2A-PAC | 363 | 833 |
| CD8SP-SARScov2-CR3022-(vL-vH)-G4S-CD3g-ECDTMCP-opt2-F-F2A-PAC | 364 | 834 |
| CD8SP-SARScov2-CR3022-(vL-vH)-G4S-CD3z-ECDTMCP-opt2-F-F2A-PAC | 365 | 835 |

TABLE 10

Exemplary SABR Targeting SARS-cov2 S-RBD

| Name of fragment | SEQ ID NO (DNA) | SEQ ID NO (PRT) |
|---|---|---|
| CD8SP-SARScov2-S-RBD-H4-vL-GS-linker-SARScov2-S-RBD-H4-vH-Myc-CD8TM-BBz-T2A-PAC | 367 | 837 |
| CD8SP-SARScov2-S-RBD-H4-vL-GS-linker-SARScov2-S-RBD-H4-vH-Myc-28z-T2A-PAC | 368 | 838 |
| CD8SP-SARScov2-S-RBD-H4-vL-GS-linker-SARScov2-S-RBD-H4-vH-Myc-28z | 369 | 839 |
| CD8SP-SARScov2-S-RBD-H4-vL-GS-linker-SARScov2-S-RBD-H4-vH-Myc-CD8TM-BBz | 370 | 840 |
| CD8SP-SARScov2-S-RBD-H4-vH-GS-linker-vL-Myc-CD8TM-BBz | 371 | 841 |
| CD8SP-SARScov2-S-RBD-H4-vL-GS-linker-SARScov2-S-RBD-H4-vH-Myc-CD8TM-z-P2A-K13-FLAG-T2A-PAC | 372 | 842 |
| CD8SP-SARScov2-S-RBD-H4-vL-[hTCRa-CSDVP]-F-F2A-SP-SARScov2-S-RBD-H4-vH-[hTCRb-KACIAH]-F-P2A-PAC | 373 | 843 |
| CD8SP-SARScov2-S-RBD-H4-vL-[hTCRb-KACIAH]-F-P2A-SP-SARScov2-S-RBD-H4-vH-[hTCRa-CSDVP]-F-F2A-PAC | 374 | 844 |
| CD8SP-SARScov2-S-RBD-H4-vL-[hTCRb-S57C]-F-P2A-SP-SARScov2-S-RBD-H4-vH-[hTCRa-T48C] | 375 | 845 |
| CD8SP-SARScov2-S-RBD-H4-vL-[hTCRb-S57C]-F-P2A-SP-SARScov2-S-RBD-H4-vH-[hTCRa-T48C]-F-F2A-K13-opt | 376 | 846 |
| CD8SP-SARScov2-S-RBD-H4-vL-[hTCRa-T48C]-F-P2A-SP-SARScov2-S-RBD-H4-vH-[hTCRb-S57C] | 377 | 847 |
| CD8SP-SARScov2-S-RBD-H4-vL-[hTCRa-T48C]-F-P2A-SP-SARScov2-S-RBD-H4-vH-[hTCRb-S57C]-F-F2A-K13-opt | 378 | 848 |
| CD8SP-V5-[hTCRb-KACIAH]-F-P2A-CD8SP-SARScov2-S-RBD-H4-vL-GS-linker-SARScov2-S-RBD-H4-vH-Myc-[hTCRa-CSDVP]-F-F2A-PAC | 379 | 849 |
| CD8SP-MYC-[hTCRa-T48C-opt1]-F-F2A-SP-SARScov2-S-RBD-H4-vL-GS-linker-SARScov2-S-RBD-H4-vH-V5-[hTCRb-S57C-opt1]-F-P2A-PAC | 380 | 850 |
| CD8SP-SARScov2-S-RBD-H4-vL-[hTCRb-opt2]-F-P2A-SP-SARScov2-S-RBD-H4-vH-[hTCRa-opt2]-F-F2A-PAC | 381 | 851 |
| CD8SP-SARScov2-S-RBD-H4-vL-[hTCRb-opt2]-F-P2A-SP-SARScov2-S-RBD-H4-vH-Myc-[preTCRa-Del48]-F-F2A-PAC | 382 | 852 |
| CD8SP-[hTCRb-opt2]-F-P2A-CD8SP-SARScov2-S-RBD-H4-vL-GS-linker-SARScov2-S-RBD-H4-vH-Myc4-[preTCRa-Del48]-F-F2A-PAC | 383 | 853 |
| CD8SP-SARScov2-S-RBD-H4-vL-V5-[hTCRg1-opt]-F-P2A-SP-SARScov2-S-RBD-H4-vH-Myc-[hTCRd-opt]-F-F2A-PAC | 384 | 854 |
| CD8SP-SARScov2-S-RBD-H4-vL-[hTCRd-opt]-F-P2A-SP-SARScov2-S-RBD-H4-vH-[hTCRg1-opt] | 385 | 855 |
| CD8SP-V5-[hTCRg1-opt]-F-P2A-CD8SP-SARScov2-S-RBD-H4-vL-GS-linker-SARScov2-S-RBD-H4-vH-Myc-[hTCRd-opt]-F-F2A-PAC | 386 | 856 |
| CD8SP-SARScov2-S-RBD-H4-vL-IgCL-Bam-CD3zECDTMCP-opt-F-P2A-Spe-SP-Bst-SARScov2-S-RBD-H4-vH-IgG1-CH1-KPN-CD3zECDTMCP-opt2-F-F2A-Xba-PAC | 387 | 857 |
| CD8SP-SARScov2-S-RBD-H4-vL-[hTCRbECD-Bam-CD3zECDTMCP-opt]-F-P2A-SP-SARScov2-S-RBD-H4-vH-[hTCRaECD-Kpn-CD3zECDTMCP-opt2] | 388 | 858 |
| CD8SP-SARScov2-S-RBD-H4-vL-[hTCRb-KAC-ECD-Bam-CD3zECDTMCP-opt]-F-P2A-SP-SARScov2-S-RBD-H4-vH-[hTCRa-CSDVP-ECD-Kpn-CD3zECDTMCP-opt2] | 389 | 859 |
| CD8SP-SARScov2-S-RBD-H4-vL-V5-[hTCRbECD-Bam-CD3zECDTMCP-opt]-F-P2A-SP-SARScov2-S-RBD-H4-vH-Myc-[hTCRaECD-Kpn-CD3zECDTM-28z-opt2] | 390 | 860 |
| CD8SP-SARScov2-S-RBD-H4-vL-V5-[hTCRbECD-Bam-CD3zECDTM-28z-opt]-F-P2A-SP-SARScov2-S-RBD-H4-vH-Myc-[hTCRaECD-Kpn-CD3zECDTM-28z-opt2] | 391 | 861 |
| CD8SP-SARScov2-S-RBD-H4-vL-V5-[hTCRbECD-Bam-CD3zECDTMCP-opt]-F-P2A-SP-SARScov2-S-RBD-H4-vH-Myc4-[hTCRaECD-Kpn-CD3zECDTM-BBz-opt2] | 392 | 862 |
| CD8SP-SARScov2-S-RBD-H4-vL-V5-[hTCRbECD-Bam-CD3zECDTM-BBz-opt]-F-P2A-SP-SARScov2-S-RBD-H4-vH-Myc4-[hTCRaECD-Kpn-CD3zECDTM-BBz-opt2] | 393 | 863 |
| CD8SP-SARScov2-S-RBD-H4-vL-CD3zECDTMCP-opt-F-P2A-Spe-SP-Bst-SARScov2-S-RBD-H4-vH-Mlu-CD3zECDTMCP-opt2-F-F2A-PAC | 394 | 864 |
| CD8SP-SARScov2-S-RBD-H4-vL-[IgCL-TCRg-6MD]-F-P2A-SP-SARScov2-S-RBD-H4-vH-[IgG1-CH1-TCRd-6MD] | 395 | 865 |
| CD8SP-SARScov2-S-RBD-H4-vL-[IgCL-TCRb-IAH-6MD]-F-P2A-SP-SARScov2-S-RBD-H4-vH-[IgG1-CH1-TCRa-SDVP-6MD] | 396 | 866 |
| CD8SP-SARScov2-S-RBD-H4-vL-[IgCL-TCRb-wt-opt2-6MD]-F-P2A-SP-SARScov2-S-RBD-H4-vH-[IgG1-CH1-TCRa-wt-op2-6MD] | 397 | 867 |
| CD8SP-SARScov2-S-RBD-H4-(vL-vH)-CD3e-ECDTMCP-opt2 | 398 | 868 |
| CD8SP-SARScov2-S-RBD-H4-(vL-vH)-CD3d-ECDTMCP-opt2 | 399 | 869 |
| CD8SP-SARScov2-S-RBD-H4-(vL-vH)-CD3g-ECDTMCP-opt2 | 400 | 870 |
| CD8SP-SARScov2-S-RBD-H4-(vL-vH)-CD3z-ECDTMCP-opt2 | 401 | 871 |

TABLE 10-continued

Exemplary SABR Targeting SARS-cov2 S-RBD

| Name of fragment | SEQ ID NO (DNA) | SEQ ID NO (PRT) |
|---|---|---|
| CD8SP-SARScov2-S-RBD-H4-(vH-vL)-CD3e-ECDTMCP-opt2 | 402 | 872 |
| CD8SP-SARScov2-S-RBD-H4-(vH-vL)-CD3d-ECDTMCP-opt2 | 403 | 873 |
| CD8SP-SARScov2-S-RBD-H4-(vH-vL)-CD3g-ECDTMCP-opt2 | 404 | 874 |
| CD8SP-SARScov2-S-RBD-H4-(vH-vL)-CD3z-ECDTMCP-opt2 | 405 | 875 |
| CD8SP-SARScov2-S-RBD-H4-vL-GS-linker-SARScov2-S-RBD-H4-vH-[hTCRa-opt2]-F-F2A-PAC | 406 | 876 |
| CD8SP-SARScov2-S-RBD-H4-vL-GS-linker-SARScov2-S-RBD-H4-vH-[hTCRb-opt2]-F-F2A-PAC | 407 | 877 |
| CD8SP-SARScov2-S-RBD-H4-vL-GS-linker-SARScov2-S-RBD-H4-vH-Myc4-[preTCRa-Del48]-F-F2A-PAC | 408 | 878 |
| CD8SP-SARScov2-S-RBD-H4-vL-[hTCRb-opt2]-F-P2A-PAC | 409 | 879 |
| CD8SP-SARScov2-S-RBD-H4-vL-[hTCRb-opt2] | 410 | 880 |
| IgHSP-SARScov2-S-RBD-H4-vH-[hTCRa-opt2]-F-F2A-BlastR | 411 | 881 |
| IgHSP-SARS-cov2-S-RBD-H4-vH-[hTCRa-opt2] | 412 | 882 |
| CD8SP-SARS-cov2-S-RBD-H4-vL-V5-[hTCRb-S57C-opt]-F-P2A-PAC | 413 | 883 |
| CD8SP-SARS-cov2-S-RBD-H4-vL-V5-[hTCRb-S57C-opt] | 414 | 884 |
| IgHSP-SARS-cov2-S-RBD-H4-vH-Myc-[hTCRa-T48C-opt]-F-F2A-BlastR | 415 | 885 |
| IgHSP-SARS-cov2-S-RBD-H4-vH-Myc-[hTCRa-T48C-opt] | 416 | 886 |
| CD8SP-SARS-cov2-S-RBD-H4-vL-Gly-Ser-Linker-SARS-cov2-S-RBD-H4-vH-[hTCRa-SDVP]-F-F2A-PAC | 417 | 887 |
| CD8SP-SARS-cov2-S-RBD-H4-vL-Gly-Ser-Linker-SARS-cov2-S-RBD-H4-vH-[hTCRb-KAIAH]-F-P2A-PAC | 418 | 888 |
| CD8SP-SARS-cov2-S-RBD-H4-(vL-vH)-G4S-CD3e-ECDTMCP-opt2-F-F2A-PAC | 419 | 889 |
| CD8SP-SARS-cov2-S-RBD-H4-(vL-vH)-G4S-CD3d-ECDTMCP-opt2-F-F2A-PAC | 420 | 890 |
| CD8SP-SARS-cov2-S-RBD-H4-(vL-vH)-G4S-CD3g-ECDTMCP-opt2-F-F2A-PAC | 421 | 891 |
| CD8SP-SARS-cov2-S-RBD-H4-(vL-vH)-G4S-CD3z-ECDTMCP-opt2-F-F2A-PAC | 422 | 892 |

TABLE 11

Exemplary SABR Targeting SARS-cov2 S-RBD

| Name of fragment | SEQ ID NO (DNA) | SEQ ID NO (PRT) |
|---|---|---|
| CD8SP-SARScov2-S-RBD-B38-vL-GS-linker-SARScov2-S-RBD-B38-vH-Myc-CD8TM-BBz-T2A-PAC | 424 | 894 |
| CD8SP-SARScov2-S-RBD-B38-vL-GS-linker-SARScov2-S-RBD-B38-vH-Myc-28z-T2A-PAC | 425 | 895 |
| CD8SP-SARScov2-S-RBD-B38-vL-GS-linker-SARScov2-S-RBD-B38-vH-Myc-28z | 426 | 896 |
| CD8SP-SARScov2-S-RBD-B38-vL-GS-linker-SARScov2-S-RBD-B38-vH-Myc-CD8TM-BBz | 427 | 897 |
| CD8SP-SARScov2-S-RBD-B38-vH-GS-linker-vL-Myc-CD8TM-BBz | 428 | 898 |
| CD8SP-SARScov2-S-RBD-B38-vL-GS-linker-SARScov2-S-RBD-B38-vH-Myc-CD8TM-z-P2A-K13-FLAG-T2A-PAC | 429 | 899 |
| CD8SP-SARScov2-S-RBD-B38-vL-[hTCRa-CSDVP]-F-F2A-SP-SARScov2-S-RBD-B38-vH-[hTCRb-KACIAH]-F-P2A-PAC | 430 | 900 |
| CD8SP-SARScov2-S-RBD-B38-vL-[hTCRb-KACIAH]-F-P2A-SP-SARScov2-S-RBD-B38-vH-[hTCRa-CSDVP]-F-F2A-PAC | 431 | 901 |
| CD8SP-SARScov2-S-RBD-B38-vL-[hTCRb-S57C]-F-P2A-SP-SARScov2-S-RBD-B38-vH-[hTCRa-T48C] | 432 | 902 |
| CD8SP-SARScov2-S-RBD-B38-vL-[hTCRb-S57C]-F-P2A-SP-SARScov2-S-RBD-B38-vH-[hTCRa-T48C]-F-F2A-K13-opt | 433 | 903 |
| CD8SP-SARScov2-S-RBD-B38-vL-[hTCRa-T48C]-F-P2A-SP-SARScov2-S-RBD-B38-vH-[hTCRb-S57C] | 434 | 904 |
| CD8SP-SARScov2-S-RBD-B38-vL-[hTCRa-T48C]-F-P2A-SP-SARScov2-S-RBD-B38-vH-[hTCRb-S57C]-F-P2A-K13-opt | 435 | 905 |
| CD8SP-V5-[hTCRb-KACIAH]-F-P2A-CD8SP-SARScov2-S-RBD-B38-vL-GS-linker-SARScov2-S-RBD-B38-vH-Myc-[hTCRa-CSDVP]-F-F2A-PAC | 436 | 906 |
| CD8SP-MYC-[hTCRa-T48C-opt1]-F-F2A-SP-SARScov2-S-RBD-B38-vL-GS-linker-SARScov2-S-RBD-B38-vH-V5-[hTCRb-S57C-opt1]-F-P2A-PAC | 437 | 907 |
| CD8SP-SARScov2-S-RBD-B38-vL-[hTCRb-opt2]-F-P2A-SP-SARScov2-S-RBD-B38-vH-[hTCRa-opt2]-F-F2A-PAC | 438 | 908 |
| CD8SP-SARScov2-S-RBD-B38-vL-[hTCRb-opt2]-F-P2A-SP-SARScov2-S-RBD-B38-vH-Myc-[preTCRa-Del48]-F-F2A-PAC | 439 | 909 |

TABLE 11-continued

Exemplary SABR Targeting SARS-cov2 S-RBD

| Name of fragment | SEQ ID NO (DNA) | SEQ ID NO (PRT) |
|---|---|---|
| CD8SP-[hTCRb-opt2]-F-P2A-CD8SP-SARScov2-S-RBD-B38-vL-GS-linker-SARScov2-S-RBD-B38-vH-Myc4-[preTCRa-Del48]-F-F2A-PAC | 440 | 910 |
| CD8SP-SARScov2-S-RBD-B38-vL-V5-[hTCRg1-opt]-F-P2A-SP-SARScov2-S-RBD-B38-vH-Myc-[hTCRd-opt]-F-F2A-PAC | 441 | 911 |
| CD8SP-SARScov2-S-RBD-B38-vL-[hTCRd-opt]-F-P2A-SP-SARScov2-S-RBD-B38-vH-[hTCRg1-opt] | 442 | 912 |
| CD8SP-V5-[hTCRg1-opt]-F-P2A-CD8SP-SARScov2-S-RBD-B38-vL-GS-linker-SARScov2-S-RBD-B38-vH-Myc-[hTCRd-opt]-F-F2A-PAC | 443 | 913 |
| CD8SP-SARScov2-S-RBD-B38-vL-IgCL-Bam-CD3zECDTMCP-opt-F-P2A-Spe-SP-Bst-SARScov2-S-RBD-B38-vH-IgG1-CH1-KPN-CD3zECDTMCP-opt2-F-F2A-Xba-PAC | 444 | 914 |
| CD8SP-SARScov2-S-RBD-B38-vL-[hTCRbECD-Bam-CD3zECDTMCP-opt]-F-P2A-SP-SARScov2-S-RBD-B38-vH-[hTCRaECD-Kpn-CD3zECDTMCP-opt2] | 445 | 915 |
| CD8SP-SARScov2-S-RBD-B38-vL-[hTCRb-KAC-ECD-Bam-CD3zECDTMCP-opt]-F-P2A-SP-SARScov2-S-RBD-B38-vH-[hTCRa-CSDVP-ECD-Kpn-CD3zECDTMCP-opt2] | 446 | 916 |
| CD8SP-SARScov2-S-RBD-B38-vL-V5-[hTCRbECD-Bam-CD3zECDTMCP-opt]-F-P2A-SP-SARScov2-S-RBD-B38-vH-Myc-zECDTM-28z-opt2] | 447 | 917 |
| CD8SP-SARScov2-S-RBD-B38-vL-V5-[hTCRbECD-Bam-CD3zECDTM-28z-opt]-F-P2A-SP-SARScov2-S-RBD-B38-vH-Myc-[hTCRaECD-Kpn-CD3zECDTM-28z-opt2] | 448 | 918 |
| CD8SP-SARScov2-S-RBD-B38-vL-V5-[hTCRbECD-Bam-CD3zECDTMCP-opt]-F-P2A-SP-SARScov2-S-RBD-B38-vH-Myc4-[hTCRaECD-Kpn-CD3zECDTM-BBz-opt2] | 449 | 919 |
| CD8SP-SARScov2-S-RBD-B38-vL-V5-[hTCRbECD-Bam-CD3zECDTM-BBz-opt]-F-P2A-SP-SARScov2-S-RBD-B38-vH-Myc4-[hTCRaECD-Kpn-CD3zECDTM-BBz-opt2] | 450 | 920 |
| CD8SP-SARScov2-S-RBD-B38-vL-CD3zECDTMCP-opt-F-P2A-Spe-SP-Bst-SARScov2-S-RBD-B38-vH-Mlu-CD3zECDTMCP-opt2-F-F2A-PAC | 451 | 921 |
| CD8SP-SARScov2-S-RBD-B38-vL-[IgCL-TCRg-6MD]-F-P2A-SP-SARScov2-S-RBD-B38-vH-[IgG1-CH1-TCRd-6MD] | 452 | 922 |
| CD8SP-SARScov2-S-RBD-B38-vL-[IgCL-TCRb-IAH-6MD]-F-P2A-SP-SARScov2-S-RBD-B38-vH-[IgG1-CH1-TCRa-SDVP-6MD] | 453 | 923 |
| CD8SP-SARScov2-S-RBD-B38-vL-[IgCL-TCRb-wt-opt2-6MD]-F-P2A-SP-SARScov2-S-RBD-B38-vH-[IgG1-CH1-TCRa-wt-op2-6MD] | 454 | 924 |
| CD8SP-SARScov2-S-RBD-B38-(vL-vH)-CD3e-ECDTMCP-opt2 | 455 | 925 |
| CD8SP-SARScov2-S-RBD-B38-(vL-vH)-CD3d-ECDTMCP-opt2 | 456 | 926 |
| CD8SP-SARScov2-S-RBD-B38-(vL-vH)-CD3g-ECDTMCP-opt2 | 457 | 927 |
| CD8SP-SARScov2-S-RBD-B38-(vL-vH)-CD3z-ECDTMCP-opt2 | 458 | 928 |
| CD8SP-SARScov2-S-RBD-B38-(vH-vL)-CD3e-ECDTMCP-opt2 | 459 | 929 |
| CD8SP-SARScov2-S-RBD-B38-(vH-vL)-CD3d-ECDTMCP-opt2 | 460 | 930 |
| CD8SP-SARScov2-S-RBD-B38-(vH-vL)-CD3g-ECDTMCP-opt2 | 461 | 931 |
| CD8SP-SARScov2-S-RBD-B38-(vH-vL)-CD3z-ECDTMCP-opt2 | 462 | 932 |
| CD8SP-SARScov2-S-RBD-B38-vL-GS-linker-SARScov2-S-RBD-B38-vH-[hTCRa-opt2]-F-F2A-PAC | 463 | 933 |
| CD8SP-SARScov2-S-RBD-B38-vL-GS-linker-SARScov2-S-RBD-B38-vH-[hTCRb-opt2]-F-F2A-PAC | 464 | 934 |
| CD8SP-SARScov2-S-RBD-B38-vL-GS-linker-SARScov2-S-RBD-B38-vH-Myc4-[preTCRa-Del48]-F-F2A-PAC | 465 | 935 |
| CD8SP-SARScov2-S-RBD-B38-vL-[hTCRb-opt2]-F-P2A-PAC | 466 | 936 |
| CD8SP-SARScov2-S-RBD-B38-vL-[hTCRb-opt2] | 467 | 937 |
| IgHSP-SARScov2-S-RBD-B38-vH-[hTCRa-opt2]-F-F2A-BlastR | 468 | 938 |
| IgHSP-SARS-cov2-S-RBD-B38-vH-[hTCRa-opt2] | 469 | 939 |
| CD8SP-SARS-cov2-S-RBD-B38-vL-V5-[hTCRb-S57C-opt]-F-P2A-PAC | 470 | 940 |
| CD8SP-SARS-cov2-S-RBD-B38-vL-V5-[hTCRb-S57C-opt] | 471 | 941 |
| IgHSP-SARS-cov2-S-RBD-B38-vH-Myc-[hTCRa-T48C-opt]-F-F2A-BlastR | 472 | 942 |
| IgHSP-SARS-cov2-S-RBD-B38-vH-Myc-[hTCRa-T48C-opt] | 473 | 943 |
| CD8SP-SARS-cov2-S-RBD-B38-vL-Gly-Ser-Linker-SARS-cov2-S-RBD-B38-vH-[hTCRa-SDVP]-F-P2A-PAC | 474 | 944 |
| CD8SP-SARS-cov2-S-RBD-B38-vL-Gly-Ser-Linker-SARS-cov2-S-RBD-B38-vH-[hTCRb-KAIAH]-F-P2A-PAC | 475 | 945 |
| CD8SP-SARS-cov2-S-RBD-B38-(vL-vH)-G4S-CD3e-ECDTMCP-opt2-F-F2A-PAC | 476 | 946 |
| CD8SP-SARS-cov2-S-RBD-B38-(vL-vH)-G4S-CD3d-ECDTMCP-opt2-F-F2A-PAC | 477 | 947 |
| CD8SP-SARS-cov2-S-RBD-B38-(vL-vH)-G4S-CD3g-ECDTMCP-opt2-F-F2A-PAC | 478 | 948 |
| CD8SP-SARS-cov2-S-RBD-B38-(vL-vH)-G4S-CD3z-ECDTMCP-opt2-F-F2A-PAC | 479 | 949 |

TABLE 12

| Name of fragment | SEQ ID NO (DNA) | SEQ ID NO (PRT) |
|---|---|---|
| Therapeutic Controls | | |
| F2A | 481 | 951 |
| T2A | 482 | 952 |
| P2A | 483 | 953 |
| E2A | 484 | 954 |
| SGSG | 485 | 955 |
| FURINE-CLEAVAGE-SITE | 486 | 956 |
| FURINE-CLEAVAGE-SITE | 487 | 957 |
| FURINE-CLEAVAGE-SITE | 488 | 958 |
| Miscellaneous | | |
| FKBP12-F36V | 1041 | 1161 |
| IKZF1-ZF2-145-167 | 1042 | 1162 |
| IKZF1-ZF2-ZF3-145-197 | 1043 | 1163 |
| IKZF1-ZF2-ZF3-145-243 | 1044 | 1164 |
| IKZFl-ZF2H1ZF2H2ZF2H3-ZF2H2x3 | 1045 | 1165 |
| SARS-cov2-S-Prt-F-P2A-Membrane-gp-F-F2A-Nucleocapsid-F-E2A-orf3 | 1047 | 1167 |
| CD8SP-StreptagII-R1-S-Protein-RBD-Mlu-mCD8-hinge-TM-F-P2A-Membrane-gp-F-F2A-Nucleocapsid | 1048 | 1168 |
| SARS-cov2-S-Prt-F-P2A-Membrane-gp-F-F2A-Nucleocapsid | 1049 | 1169 |
| SARScov2-HLA-A0201-PEPTIDES-F-P2A-Membrane-gp-F-F2A-Nucleocapsid | 1050 | 1170 |
| Ub-G76A-SARScov2-HLA-A0201-Polyepitopes-F-P2A-Membrane-gp-F-F2A-Nucleocapsid | 1051 | 1171 |
| SARScov2-HLA-DRB10401-Polyepitopes-F-P2A-Membrane-gp-F-F2A-Nucleocapsid | 1052 | 1172 |
| Ub-G76A-SARScov2-HLA-DRB10401-Polyepitopes-F-P2A-Membrane-gp-F-F2A-Nucleocapsid | 1053 | 1173 |
| SARS-cov2-Spike-Glycoprotein-1-RBD-(S1-RBD)-FKBP12-F36V | 1054 | 1174 |
| SARS-cov2-Spike-Glycoprotein-1-RBD-(S1-RBD)-IKZF1-ZF2-ZF3-145-243 | 1055 | 1175 |
| SARS-cov2-Spike-Glycoprotein-FKBP12-F36V | 1056 | 1176 |
| SARS-cov2-Spike-Glycoprotein-IKZF1-ZF2-ZF3-145-243 | 1057 | 1177 |
| SARS-cov2-nucleocapsid-FKBP12-F36V | 1058 | 1178 |
| SARS-cov2-nucleocapsid-IKZF1-ZF2-ZF3-145-243 | 1059 | 1179 |
| SARS-cov2-membrane-Glycoprotein-FKBP12-F36V | 1060 | 1180 |
| SARS-cov2-membrane-Glycoprotein-IKZF1-ZF2-ZF3-145-243 | 1061 | 1181 |
| CD8SP-StreptagII-R1-S-Protein-RBD-Mlu-mCD8-hinge-TM-F-P2A-Membrane-gp-F-F2A-Nucleocapsid-FKBP12-F36V | 1062 | 1182 |
| CD8SP-StreptagII-R1-S-Protein-RBD-Mlu-mCD8-hinge-TM-F-P2A-Membrane-gp-F-F2A-Nucleocapsid-IKZF1-ZF2-145-167 | 1063 | 1183 |
| CD8SP-StreptagII-R1-S-Protein-RBD-Mlu-mCD8-hinge-TM-F-P2A-Membrane-gp-F-F2A-Nucleocapsid-IKZF1-ZF2-ZF3-145-197 | 1064 | 1184 |
| CD8SP-StreptagII-R1-S-Protein-RBD-Mlu-mCD8-hinge-TM-F-P2A-Membrane-gp-F-F2A-Nucleocapsid-IKZF1-ZF2-ZF3-145-243 | 1065 | 1185 |
| SARS-cov2-S-Prt-F-P2A-Membrane-gp-F-F2A-Nucleocapsid-FKBP12-F36V | 1066 | 1186 |
| SARScov2-HLA-A0201-PEPTIDES-F-P2A-Membrane-gp-F-F2A-Nucleocapsid-FKBP12-F36V | 1067 | 1187 |
| Ub-G76A-SARScov2-HLA-A0201-Polyepitopes-F-P2A-Membrane-gp-F-F2A-Nucleocapsid-FKBP12-F36V | 1068 | 1188 |
| SARScov2-HLA-DRB10401-Polyepitopes-F-P2A-Membrane-gp-F-F2A-Nucleocapsid-FKBP12-F36V | 1069 | 1189 |
| Ub-G76A-SARScov2-HLA-DRB10401-Polyepitopes-F-P2A-Membrane-gp-F-F2A-Nucleocapsid-FKBP12-F36V | 1070 | 1190 |
| SARS-cov2-S-Prt-F-P2A-Membrane-gp-F-F2A-Nucleocapsid-IKZF1-ZF2-ZF3-145-243 | 1071 | 1191 |
| SARScov2-HLA-A0201-PEPTIDES-F-P2A-Membrane-gp-F-F2A-Nucleocapsid-IKZF1-ZF2-ZF3-145-243 | 1072 | 1192 |
| Ub-G76A-SARScov2-HLA-A0201-Polyepitopes-F-P2A-Membrane-gp-F-F2A-Nucleocapsid-IKZF1-ZF2-ZF3-145-243 | 1073 | 1193 |
| SARScov2-HLA-DRB10401-Polyepitopes-F-P2A-Membrane-gp-F-F2A-Nucleocapsid-IKZF1-ZF2-ZF3-145-243 | 1074 | 1194 |
| Ub-G76A-SARScov2-HLA-DRB10401-Polyepitopes-F-P2A-Membrane-gp-F-F2A-Nucleocapsid-IKZF1-ZF2-ZF3-145-243 | 1075 | 1195 |
| | 1076 | 1196 |
| SARS-cov2-Spike-Glycoprotein-S2-GGSG-NLuc-4xFLAG-x2STREP-8xHis-T2A-PAC | 1077 | 1197 |
| SARS-cov2-Spike-Glycoprotein-S1-ND1-GGSG-NLuc-4xFLAG-x2STREP-8xHis-T2A-PAC | 1078 | 1198 |
| SARS-cov2-Spike-Glycoprotein-S1-ND2-GGSG-NLuc-4xFLAG-x2STREP-8xHis-T2A-PAC | 1079 | 1199 |
| CD8SP-StreptagII-R1-S-Protein-RBD-Mlu-mCD8-hinge-TM | 1080 | 1200 |
| CD8SP-hu-mROO5-1-(vL-vH)-GGSG-NLuc-4xFLAG-x2STREP-8xHis-T2A-PAC | 1081 | 1201 |

TABLE 12-continued

| Name of fragment | SEQ ID NO (DNA) | SEQ ID NO (PRT) |
|---|---|---|
| CD8SP-SARScov2-CR3022-(vL-vH)-GGSG-NLuc-4xFLAG-x2STREP-8xHis-T2A-PAC | 1082 | 1202 |
| CD8SP-SARS-cov2-S-RBD-H4-(vL-vH)-GGSG-NLuc-4xFLAG-x2STREP-8xHis-T2A-PAC | 1083 | 1203 |
| CD8SP-SARScov2-S-RBD-B38-(vL-vH)-GGSG-NLuc-4xFLAG-x2STREP-8xHis-T2A-PAC | 1084 | 1204 |
| CD19-ECD-GGSG-NLuc-4xFlag-2xStreptag-8xHis-T2A-Pac | 1085 | 1205 |
| CD33-ECD-GGSG-NLuc-4xFlag-2xStreptag-8xHis-T2A-Pac | 1086 | 1206 |
| CD8SP-BCMA-ECD-GGSG-NLuc-4xFlag-2xStreptag-8xHis-T2A-Pac | 1087 | 1207 |
| CD8SP-StreptagII-R1-S1-Protein-RBD-ECD-GGSG-NLuc-4xFlag-2xStreptag-8xHis-T2A-Pac | 1088 | 1208 |
| CD8SP-R1-S1-Protein-RBD-ECD-GGSG-NLuc-4xFlag-2xStreptag-8xHis-T2A-Pac | 1089 | 1209 |
| S1-Protein-ECD-GGSG-NLuc-4xFlag-2xStreptag-8xHis | 1090 | 1210 |
| SARS-cov2-nucleocapsid-GGS-NLuc-4xFlag-2xStreptag-8xHis-T2A-PAC | 1091 | 1211 |
| orf3a-GGSG-NLuc-4xFlag-2xStreptag-8xHis | 1092 | 1212 |
| ACE2-ECD-GGS-NLuc-4xFlag-2xStreptag-8xHis | 1093 | 1213 |
| SARS-cov2-Spike-Glycoprotein-S2-GGSG-Gluc-4xFLAG-x2STREP-8xHis-T2A-PAC | 1095 | 1215 |
| SARS-cov2-Spike-Glycoprotein-S1-ND1-GGSG-Gluc-4xFLAG-x2STREP-8xHis-T2A-PAC | 1096 | 1216 |
| SARS-cov2-Spike-Glycoprotein-S1-ND2-GGSG-Gluc-4xFLAG-x2STREP-8xHis-T2A-PAC | 1097 | 1217 |
| CD8SP-hu-mROO5-1-(vL-vH)-GGSG-Gluc-4xFLAG-x2STREP-8xHis-T2A-PAC | 1098 | 1218 |
| CD8SP-SARScov2-CR3022-(vL-vH)-GGSG-Gluc-4xFLAG-x2STREP-8xHis-T2A-PAC | 1099 | 1219 |
| CD8SP-SARS-cov2-S-RBD-H4-(vL-vH)-GGSG-Gluc-4xFLAG-x2STREP-8xHis-T2A-PAC | 1100 | 1220 |
| CD8SP-SARScov2-S-RBD-B38-(vL-vH)-GGSG-Gluc-4xFLAG-x2STREP-8xHis-T2A-PAC | 1101 | 1221 |
| CD19-ECD-GGSG-Gluc-4xFlag-2xStreptag-8xHis-T2A-Pac | 1102 | 1222 |
| CD33-ECD-GGSG-Gluc-4xFlag-2xStreptag-8xHis-T2A-Pac | 1103 | 1223 |
| CD8SP-BCMA-ECD-GGSG-Gluc-4xFlag-2xStreptag-8xHis-T2A-Pac | 1104 | 1224 |
| CD8SP-StreptagII-R1-S1-Protein-RBD-ECD-GGSG-Gluc-4xFlag-2xStreptag-8xHis-T2A-Pac | 1105 | 1225 |
| CD8SP-R1-S1-Protein-RBD-ECD-GGSG-Gluc-4xFlag-2xStreptag-8xHis-T2A-Pac | 1106 | 1226 |
| S1-Protein-ECD-GGSG-Gluc-4xFlag-2xStreptag-8xHis | 1107 | 1227 |
| SARS-cov2-nucleocapsid-GGS-Gluc-4xFlag-2xStreptag-8xHis-T2A-PAC | 1108 | 1228 |
| orf3a-GGSG-Gluc-4xFlag-2xStreptag-8xHis | 1109 | 1229 |
| ACE2-ECD-GGS-Gluc-4xFlag-2xStreptag-8xHis | 1110 | 1230 |
| SARS-cov2-Spike-Glycoprotein-S2-GGSG-TLuc-4xFLAG-x2STREP-8xHis-T2A-PAC | 1112 | 1232 |
| SARS-cov2-Spike-Glycoprotein-S1-ND1-GGSG-TLuc-4xFLAG-x2STREP-8xHis-T2A-PAC | 1113 | 1233 |
| SARS-cov2-Spike-Glycoprotein-S1-ND2-GGSG-TLuc-4xFLAG-x2STREP-8xHis-T2A-PAC | 1114 | 1234 |
| CD8SP-hu-mROO5-1-(vL-vH)-GGSG-TLuc-4xFLAG-x2STREP-8xHis-T2A-PAC | 1115 | 1235 |
| CD8SP-SARScov2-CR3022-(vL-vH)-GGSG-TLuc-4xFLAG-x2STREP-8xHis-T2A-PAC | 1116 | 1236 |
| CD8SP-SARS-cov2-S-RBD-H4-(vL-vH)-GGSG-TLuc-4xFLAG-x2STREP-8xHis-T2A-PAC | 1117 | 1237 |
| CD8SP-SARScov2-S-RBD-B38-(vL-vH)-GGSG-TLuc-4xFLAG-x2STREP-8xHis-T2A-PAC | 1118 | 1238 |
| CD19-ECD-GGSG-TLuc-4xFlag-2xStreptag-8xHis-T2A-Pac | 1119 | 1239 |
| CD33-ECD-GGSG-TLuc-4xFlag-2xStreptag-8xHis-T2A-Pac | 1120 | 1240 |
| CD8SP-BCMA-ECD-GGSG-TLuc-4xFlag-2xStreptag-8xHis-T2A-Pac | 1121 | 1241 |
| CD8SP-StreptagII-R1-S1-Protein-RBD-ECD-GGSG-TLuc-4xFlag-2xStreptag-8xHis-T2A-Pac | 1122 | 1242 |
| CD8SP-R1-S1-Protein-RBD-ECD-GGSG-TLuc-4xFlag-2xStreptag-8xHis-T2A-Pac | 1123 | 1243 |
| S1-Protein-ECD-GGSG-TLuc-4xFlag-2xStreptag-8xHis | 1124 | 1244 |
| SARS-cov2-nucleocapsid-GGS-TLuc-4xFlag-2xStreptag-8xHis-T2A-PAC | 1125 | 1245 |
| orf3a-GGSG-TLuc-4xFlag-2xStreptag-8xHis | 1126 | 1246 |
| ACE2-ECD-GGS-TLuc-4xFlag-2xStreptag-8xHis | 1127 | 1247 |
| SARS-cov2-Spike-Glycoprotein-S2-GGSG-MLuc7-M43L-M110L-4xFLAG-x2STREP-8xHis-T2A-PAC | 1129 | 1249 |
| SARS-cov2-Spike-Glycoprotein-S1-ND1-GGSG-MLuc7-M43L-M110L-4xFLAG-x2STREP-8xHis-T2A-PAC | 1130 | 1250 |
| SARS-cov2-Spike-Glycoprotein-S1-ND2-GGSG-MLuc7-M43L-M110L-4xFLAG-x2STREP-8xHis-T2A-PAC | 1131 | 1251 |
| CD8SP-hu-mROO5-1-(vL-vH)-GGSG-MLuc7-M43L-M110L-4xFLAG-x2STREP-8xHis-T2A-PAC | 1132 | 1252 |

TABLE 12-continued

| Name of fragment | SEQ ID NO (DNA) | SEQ ID NO (PRT) |
|---|---|---|
| CD8SP-SARScov2-CR3022-(vL-vH)-GGSG-MLuc7-M43L-M110L-4xFLAG-x2STREP-8xHis-T2A-PAC | 1133 | 1253 |
| CD8SP-SARS-cov2-S-RBD-H4-(vL-vH)-GGSG-MLuc7-M43L-M110L-4xFLAG-x2STREP-8xHis-T2A-PAC | 1134 | 1254 |
| CD8SP-SARScov2-S-RBD-B38-(vL-vH)-GGSG-MLuc7-M43L-M110L-4xFLAG-x2STREP-8xHis-T2A-PAC | 1135 | 1255 |
| CD19-ECD-GGSG-MLuc7-M43L-M110L-4xFlag-2xStreptag-8xHis-T2A-Pac | 1136 | 1256 |
| CD33-ECD-GGSG-MLuc7-M43L-M110L-4xFlag-2xStreptag-8xHis-T2A-Pac | 1137 | 1257 |
| CD8SP-BCMA-ECD-GGSG-MLuc7-M43L-M110L-4xFlag-2xStreptag-8xHis-T2A-Pac | 1138 | 1258 |
| CD8SP-StreptagII-R1-S1-Protein-RBD-ECD-GGSG-MLuc7-M43L-M110L-4xFlag-2xStreptag-8xHis-T2A-Pac | 1139 | 1259 |
| CD8SP-R1-S1-Protein-RBD-ECD-GGSG-MLuc7-M43L-M110L-4xFlag-2xStreptag-8xHis-T2A-Pac | 1140 | 1260 |
| S1-Protein-ECD-GGSG-MLuc7-M43L-M110L-4xFlag-2xStreptag-8xHis | 1141 | 1261 |
| SARS-cov2-nucleocapsid-GGS-MLuc7-M43L-M110L-4xFlag-2xStreptag-8xHis-T2A-PAC | 1142 | 1262 |
| orf3a-GGSG-MLuc7-M43L-M110L-4xFlag-2xStreptag-8xHis | 1143 | 1263 |
| ACE2-ECD-GGS-MLuc7-M43L-M110L-4xFlag-2xStreptag-8xHis | 1144 | 1264 |

As used herein, the term "biological equivalent thereof" or "variant" or "functional variant" is intended to be synonymous with "equivalent thereof" when referring to a reference protein, antibody or fragment thereof, polypeptide or nucleic acid, intends those having minimal homology while still maintaining desired structure or functionality.

As used herein, the term "CDR" or "complementarity determining region" is intended to mean the non-contiguous antigen combining sites found within the variable region of both heavy and light chain polypeptides. The SEQ IDs of the CDRs of the different vL and vH segments that can be used in the construction of antigen binding domains of SABR targeting the receptor binding domain of the spike glycoprotein of SARS-cov2 of the current disclosure are provided in Table 7A.

The SEQ IDs of the CDRs of the different vL and vH segments that can be used in the construction of antigen binding domains of SABR targeting different antigens (e.g., CD19, CD20, CD22, Mesothelin etc.) of the current disclosure are provided in SEQ ID NO: 13204-14121 and SEQ ID NO: 14122-15039, respectively (Tables 6A, B) of PCT/US18/53247 and in Tables 5-6 in PCT/US2017/064379, which are incorporated herein by reference.

"Chimeric antigen receptors" (CARs) are artificial (non-naturally occurring) immune cell (e.g., T cell) receptors contemplated for use as a therapy for cancer, using a technique called adoptive cell transfer.

The term "SABR" or "Synthetic Antigen Binding Receptor", "Synthetic Antigen Receptor (SAR)" or "Antigen binding Receptor" or "ABR" as described herein refers to any receptor that has an antigen binding domain and is capable of transmitting a signal to an immune cell (e.g., T cell, NK cell, macrophage etc.) when expressed in the said immune cell. SABR when expressed in an effector cell, provides the cell with specificity for a target cell (e.g., a virally infected cell or a cancer cell) that express the antigen bound by the SABR. The antigen binding domain of a SABR may comprise of a scFv, a vL, vH, antibody, antibody fragment (e.g., Fab), antibody like moiety, Vα, Vβ, cytokine, receptor etc. in one embodiment, a SABR has at least one antigen binding domain and at least one transmembrane or membrane anchoring domain that allows it to be expressed on the cell surface. The term "Synthetic Antigen Binding Receptor (SABR)", as used herein, comprises CARs and also encompasses newer approaches to conferring antigen specificity onto cells, such as Antibody-TCR chimeric molecules or Ab-TCR (WO 2017/070608 A1 incorporated herein by reference), TCR receptor fusion proteins or TFP (WO 2016/187349 A1 incorporated herein by reference), Synthetic Immune Receptors (SIRs) (see, WO 2018/102795 A1, incorporated herein by reference), Tri-functional T cell antigen coupler (Tri-TAC or TAC) (see, WO 2015/117229 A1, incorporated herein by reference) and zSIR (see, PCT/US2019/035096, incorporated herein by reference). The nucleic acid sequences of several exemplary TFPs comprising the different antigen binding domains (e.g., vL and vH fragments, vHH, ligands and receptors etc.) and based on CD3ε, CD3δ, CD3γ and CD3ζ chains and co-expressing the optional accessory module NEMO-K277A are presented in SEQ ID NO:1900-2205, 2206-2511, 2512-2817, 2818-3123, respectively (Table 13) of PCT/US18/53247, which is incorporated in its entirety by reference herein. The order of the antigen binding domains contained in the construct of different CAR architectures and BiTE listed in Table 13 of PCT/US18/53247, which is incorporated in its entirety by reference herein is the same as the order of the constructs on the zCAR-K277A architecture presented in Table 12 of PCT/US18/53247, which is incorporated in its entirety by reference herein. Typically, the term "SABR-T cell" is used, to refer to T-cells that have been engineered to express a Synthetic antigen binding receptor. Thus, T lymphocytes bearing such SABRs are generally referred to as SABR-T lymphocytes. If the SABR is a CAR, then the T cells are referred to as CAR-T cells. SABRs can be also expressed in cells other than T cells, such as hematopoietic stem cells, induced pluripotent stem cells (iPSC), NK cells and macrophage.

The term "binding" or "interacting" refers to an association, which may be a stable association, between two molecules, e.g., between a TCR and a peptide/MHC, due to, for example, electrostatic, hydrophobic, ionic and/or hydrogen-bond interactions under physiological conditions.

The term "single chain variable fragment" or "scFv" refers to an Fv fragment in which the heavy chain domain and the light chain domain are linked.

The term "Fv fragment" refers to the fragment of an antibody comprising the variable domains of its heavy chain and light chain.

The term "specifically bind", "specific binding", or "targeting", as used herein, when referring to a polypeptide (including antibodies) or receptor, refers to a binding reaction which is determinative of the presence of the protein or polypeptide or receptor in a heterogeneous population of proteins and other biologicals.

The term "epitope" means a protein determinant capable of specific binding to an antibody or TCR.

The term "expression vector" refers to a vector comprising a recombinant polynucleotide comprising expression control sequences operatively linked to a nucleotide sequence to be expressed.

"Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

"Immune effector cell," as that term is used herein, refers to a cell that is involved in an immune response, e.g., in the promotion of an immune effector response.

"Immune effector function" or "immune effector response," "effector function" refers to the specialized function of a differentiated immune cell.

"Native" or "Naturally occurring" or "endogenous" as used herein refers to a gene, protein, nucleic acid (e.g., DNA, RNA etc.) or fragment thereof that is native to a cell or is naturally expressed in a cell.

As used herein a "non-naturally occurring agent" or "non-native" or "exogenous" refers to an agent that is not naturally expressed in a cell. Stated another way, the non-naturally occurring agent is "engineered" to be expressed in a cell. As used herein a "non-naturally occurring immune receptor" or "exogenous immune receptor" refers to an immune receptor that is not naturally expressed in an immune cell. Stated another way, the non-naturally occurring immune receptor is "engineered" to be expressed in an immune cell.

The term "Synthetic Immune Receptor" or alternatively a "SIR" refers to next generation CAR platforms that are described in WO 2018/102795 A1 which is incorporated herein by reference.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body.

As used herein, "specific binding" refers to the ability of a SAM to bind to a protein or to a peptide presented on an MHC (e.g. class I MEC or class II MEC). T In certain embodiments, agents of the invention may be used alone or conjointly administered with another type of therapeutic agent.

The terms "T-cell" and "T-lymphocyte" are interchangeable and used synonymously herein. Examples include but are not limited to naïve T cells ("lymphocyte progenitors"), central memory T cells, effector memory T cells, stem memory T cells (Tscm), iPSC-derived T cells, synthetic T cells or combinations thereof.

The term "TCR receptor fusion proteins" or "TFP" refers to a next generation SAR platform as described in WO 2016/187349 A1 which is incorporated herein by reference.

"SARS-cov2" or "novel coronavirus" or "severe acute respiratory syndrome coronavirus 2" as described herein is the etiological agent of coronavirus disease 2019 (COVID-19) or a variant thereof.

"SARS-cov2 immune" or "SARS-cov2 positive" as the term used herein refers to subjects or donors who have evidence of cellular and/or humoral immunity to SARS-cov2. In an embodiment, the SARS-cov2 immune subjects are subjects who have a history of infection with SARS-cov2. In an embodiment, the SARS-cov2 immune subjects are subjects who have a history of having received a SARS-cov2 vaccine. In an embodiment, the SARS-cov2 immune subjects have T cells that recognize one or more antigens encoded by SARS-cov2. In an embodiment, the SARS-cov2 immune subjects have antibodies against one or more antigens encoded by SARS-cov2. Exemplary antigens encoded by SARS-cov2 include Spike glycoprotein, nucleocapsid protein and membrane glycoprotein.

"SARS-Cov2 specific T cells" or "SARS-Cov2 reactive T cells" as described herein refer to T cells that bind to one or more SARS-Cov2 peptides when presented by the MHC complex. SARS-Cov2 specific T cells can be recognized by methods known in the art, such as staining with MHC tetramers.

Matador Assay as the term used herein refers to a non-radioactive luciferase-based cytotoxicity assay as described in PCT/US2017/024843 and Matta H, et al. (2018) Scientific reports 8(1):199, which are incorporated in their entirety by reference herein.

Topanga Assay as the term used herein refers to a non-radioactive luciferase based assay for detection of an antigen binding domain or an SABR incorporating an antigen binding domain as described in Gopalakrishnan R, et al. (2019) Scientific reports 9(1):1957, which is incorporated in their entirety by reference herein.

Malibu-Glo assay as the term used herein refers to a non-radioactive luciferase based assay for detection of an antigen as described in Natarajan V, et al. (2020) Scientific reports 10(1):2318, which is incorporated in their entirety by reference herein.

Generation and Expansion of Viral Specific (e.g., SARS-Cov2 Specific) T Cells for Adoptive Cellular Therapy In one aspect, the studies disclosed herein seek to determine the impact of various SABR-T cell stimuli amenable to a high-yield manufacturing process, and/or for enriching memory T cell immunophenotypes in a final therapeutic product. Standard anti-CD3/CD28 bead-based stimulation is widely used in the field as a method to expand T cells ex vivo or in vitro prior to transduction with SABR-encoding vectors. However, disclosed herein are manufacturing processes for SARS-Cov2 antigen-stimulated T cells (e.g., SARS-CoV2-specific T cells) that also express one or more SABRs. Such processes may comprise an initial T-cell enrichment step, wherein $CD3^+$ T cells are enriched/purified from a more heterogeneous mixture of cells (e.g., from whole blood, from PBMCs, and the like); stimulated to recognize and respond to pre-selected antigens (e.g., viral antigens or other tumor/disease-associated antigens, etc.); and transduced with one or more SABR constructs. For example, a sample of cells obtained from a SARS-Cov2 subject comprising $CD3^+$ T cells (e.g., PBMC) may be enriched for $CD3^+$ T cells, and said $CD3^+$ T cells brought into contact with antigen-presenting stimulator cells.

In an embodiment, the SARS-Cov2 specific T cells are directly used to manufacture SABR-T cells. In an embodiment, the SARS-Cov2 specific T cells are used to generate iPSC cells. In an embodiment, the iPSC (induced pluripotent stem cells) generated from SARS-Cov2 specific T cells are used to express SABR and then differentiated into SARS-Cov2 specific T cells expressing the SABR. Methods to generate iPSC from T cells and methods to generate T cells from iPSC are known in the art.

In an embodiment, the $CD3^+$ T cells are isolated from the sample and then expanded by making contact with the SARS-Cov2 antigen-presenting stimulator cells. More preferably, the T cells and SARS-Cov2 antigen-presenting stimulator cells (e.g., BLCLs, T cells) are derived from the same sample and are thus HLA-matched. Such cell selection methods and techniques generally include positive selection of $CD3^+$ and/or $CD19^+$ cells from the sample and/or negative selection by depletion of undesired cells or components from the sample. For example, and without limitation, such methods comprise selection with live cell sorting techniques (e g, fluorescence activated cell sorting), anti-CD3 and/or anti-CD19 beads (e.g., magnetic beads), plastic adherence, depletion of B cells, elutriation, and/or combinations thereof. A portion of the resultant $CD3^+$ T cells may be transduced with a viral vector encoding a synthetic antigen binding receptor or SABR (e.g. a CAR, SIR, Ab-TCR, cTCR, TFP etc.) before and/or after contact with antigen-presenting stimulator cells. In an exemplary embodiment, SABR targeting CD19 are presented in SEQ ID NO: 253-308 (Table 8). In an embodiment, the remaining $CD3^+$ T cell population may be transduced with a vector encoding one or more proteins or peptides encoded by a virus (e.g., SARS-cov2) and expanded to generate antigen-presenting stimulator cells. In an exemplary embodiment, SARS-cov2 encoded proteins that can be used for generation of stimulator cells are provided in nucleic acid SEQ ID NO:231-234 and amino acid SEQ ID NO:701-704 (Table 7). SARS-cov2 encoded polypeptides and polyepitopes that can be used for generation of stimulator cells are provided in nucleic acid SEQ ID NO:225-229 and amino acid SEQ ID NO:695-699 (Table 7). In an embodiment, B cells or BLCLs may be transduced with a vector encoding one or more proteins (SEQ NO:701-704) or polypeptides (SEQ ID NO:225-229) encoded by a virus (e.g., SARS-cov2) and expanded to generate antigen-presenting stimulator cells.

Until now, methods for the manufacture of SABR-T cells known in the art have relied on either a crude and heterogeneous starting material, such as PBMC (see Sun et al. Journal for ImmunoTherapy of Cancer (2015) 3:5) or highly purified isolates of specific T cell types, i.e., $CD4^+$, $CD8^+$ T cells, or specific ratios thereof (see Terakura et al. Blood (2011) 119: 1 and Turtle et al. Sci Transl Med. (2016) September 7; 8). However, the invention disclosed herein provides ex vivo methods for enriching SARS-cov2 antigen-specific T cells to be used in the manufacture of SABR-T cells and for use as cellular vaccine. Notably, in some preferred embodiments, such methods comprise obtaining a sample of cells (e.g., PBMC) from a SARS-cov2-immune subject comprising $CD3^+$ cells and contacting said $CD3^+$ cells with SARS-cov2 antigen-presenting stimulator cells. In an embodiment, the $CD3^+$ T cells are isolated from the sample prior to contacting the SARS-cov2 antigen-presenting stimulator cells by methods known in the art (e.g., positive selection of $CD3^+$ cells from the sample and/or negative selection by depletion of undesired cells or components from the sample). For example, and without limitation, such methods include selection using fluorescence activated cell sorting (FACS), with anti-CD3 beads (e.g., magnetic beads), plastic adherence, depletion of NK cells using anti-CD56, elutriation, and/or combinations thereof. Sensitizing the selected $CD3^+$ cells to SARS-cov2 viral antigen, may promote a central memory phenotype in the resultant SARS-cov2 antigen-specific T cell population. Such cells may be transduced with a viral vector encoding a synthetic antigen binding receptor (SABR) before and/or after contact with the SARS-cov2 antigen-presenting stimulator cells. In an exemplary embodiment, T cells are transduced with one or more SABRs targeting CD19, which are presented in SEQ ID NO: 253-308 (Table 8). Exemplary SABR targeting other antigens are known in the art and described in WO 2017/070608 A1, WO 2016/187349 A1, WO 2018/102795 A1, WO 2015/117229 A1, PCT/US2019/035096, which are all incorporated herein by reference. In some such embodiments the SABR-expressing SARS-cov2 antigen-specific $CD3^+$ T cells are cultured with the SARS-cov2 antigen-presenting stimulator cells.

The initial $CD3^+$ enrichment step disclosed herein provides a starting material that is significantly less heterogeneous than a PBMC sample yet retains some level of heterogeneity over highly purified cell fractions. Without wishing to be bound by theory, it is postulated that by using an initial $CD3^+$ enrichment step, the starting material comprises a mixture of cells (including at least a plurality of effector T cell types, T helper cells ($CD4^+$ T cells/TH cells), cytotoxic T cells ($cD8^+$ T cells/CTLs), memory T cell types (i.e., central memory T cells (TCM cells), effector memory T cells (TEM cells), tissue resident memory T cells (TRI), and virtual memory T cells (TVM cells)), regulatory T cells (Treg cells), natural killer T cells (NKT cells), mucosal associated invariant cells (MAIT cells), gamma delta T cells (gd T cells), double-negative T cells (DNTs), $CD3^+$ B cells, or any combination thereof) which may work synergistically or provide an advantageous milieu to promote increased viability and proliferation of SARS-cov2-antigen-specific T cells following contact with SARS-cov2-presenting APCs, improved transduction efficiency of SABR-expressing vector in such SARS-cov2 antigen-specific T cells, and a higher percentage of TCM cells in the final therapeutic composition.

In some embodiments, further enrichment is conducted following T cell stimulation with a SARS-cov2 antigen. For example, NK depletion (e.g., CD56 depletion) may be employed prior to a subsequent antigen stimulation step (i.e. prior to re-stimulation of enriched, SARS-cov2 antigen-specific, T cells with one or more SARS-cov2 antigens)

Stimulation and Transduction

Manufacture of T cells expressing an SABR (e.g., a CAR, SIR, Ab-TCR, or recombinant TCR) that specifically binds to a protein or a peptide presented on a class I MHC requires T cell expansion against defined antigens. In some embodiments, the T cells express a SABR (e.g., a CAR, SIR, Ab-TCR, TFP, recombinant TCR etc.) that specifically binds to a disease-associated peptide (e.g., a tumor-associate peptide, antigen, ligand, or the like) or protein antigen (e.g., CD19, CD20, CD22, BCMA, Mesothelin, PSMA etc.).

SARS-cov2 antigen delivery may be via viral infection by native virus, or via transduction using recombinant virus, of a sample of peripheral blood mononuclear cells (PBMCs) from healthy donors, isolated B cell lymphoblastoid cells (e.g., $CD19^+$ BLEU) therefrom or isolated T cells (e.g., $CD3^+$ T cells) therefrom. In an embodiment, SARS-cov2 antigen delivery may be via viral infection by native virus, or via transduction using recombinant virus, of an antigen presenting cell line. Exemplary antigen presenting cell lines include, but are not limited to, K562, REC-1, MINO, JEKO-1, and GRANTA-519. In an embodiment, in addition to presenting SARS-cov2 specific antigens, the APC (e.g., K562, REC-1, MINO, JEKO-1, and GRANTA-519 cells) are engineered to express one or more co-stimulatory molecules (e.g., 4-1BBL, CD32, CD80, CD83 and CD86) or cytokines (IL2, IL15 and IL21 etc.).

Thus, the infected or transduced cells act as antigen-presenting cells and are referred to as "stimulators". In certain embodiments, the stimulator cells also express a peptide (i.e., antigen) or protein on the cell surface that is recognized by the SABR. The stimulator cells may endogenously express such SABR-targeted peptides (e.g., peptides derived from CD1.9, CD20, CD22, NY-ESO-1, WT1, Myc, AFP etc.) or proteins (e.g., CD19, CD20, CD22, BCMA, Mesothelin, PSMA etc.), or protein fragments (e.g. tCD19, tBCMA etc.) or be engineered to express such peptides/proteins. The SEQ ID of tEGFRviii, tCD19 and tBCMA are provided in SEQ ID NO: 194-196 (Table 6). The stimulator cells may also co-express a protein that selectively activates the NF-κB pathway. The nucleic acid and amino acid sequence of vFLIP K13, an exemplary protein that selectively activates NF-κB pathway, are provided in SEQ ID NO: 199 and 669, respectively. Other exemplary proteins known to selectively activate the NF-κB pathway include NEMO-K277A and constitutive active mutants of IKKα, IKKβ, NIK and MYD88. The viral vector used to transduce stimulators may be a recombinant, replication incompetent virus (e.g., an adenovirus or a lentiviral vector such as pLENTI-EF1α; SEQ ID NO: 1). Alternatively, said stimulator cells are infected with a wild type/native virus.

A separate sample or culture (e.g., PBMCs from the same donor that are not used for transduction, a sample of PBMCs from a different donor, or CD3$^+$ cells isolated therefrom) comprises "responders" and contains T cells that become the active component of a therapy, expressing a T cell receptor that specifically binds to a peptide or protein antigen presented by stimulator cells.

In an embodiment, SARS-Cov2 specific T cells are obtained from an SARS-CoV2 immune subject. In an embodiment, SARS-Cov2 specific T cells are obtained from a SARS-CoV2 immune subject who has received a SARS-Cov2 specific vaccine. In an embodiment, SARS-Cov2 specific T cells are obtained from a SARS-CoV2 immune subject who has received a booster dose of a SARS-Cov2 specific vaccine. In an embodiment, the SARS-Cov2 specific T cells are obtained from a subject 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months or 2 years after receiving a primary and/or booster dose of a SARS-Cov2 specific vaccine. In an exemplary embodiment, the SARS-CoV2 vaccine is a vaccine that is manufactured by Moderna, Pfizer, Astrazaneca or Johnson and Johnson. The SARS-Cov2 specific T cells can be isolate by any of the methods known in the art.

In an embodiment, the donor from whom the responder T cells are collected is a SARS-cov2 immune donor who has recovered from a SARS-cov2 infection and/or shows evidence of cellular and/or humoral immunity to SARS-cov2. A number of test to determine cellular and humoral immunity to SARS-cov2 are known in the art, including, but not limited to, presence of IgG antibodies or cells specific to one or more proteins (e.g. Spike glycoprotein or nucleocapsid protein) or peptide antigens encoded by SARS-cov2. In an embodiment, the donor from whom the responder T cells are collected is a SARS-cov2 immune donor who has received a SARS-cov2 vaccine and shows evidence of cellular and/or humoral immunity to SARS-cov2. In an embodiment, the donor from whom the responder T cells are collected is a SARS-cov2 immune donor who is administered one or more booster doses of a SARS-cov2 vaccine prior to collection of PBMC and T cells. A number of SARS-cov2 vaccines are being tested and are known in the art. In an embodiment, the donor is given up to 5 or more booster doses (e.g., 2, 3, 4, 5 booster doses etc.) of SARS-cov2 vaccine prior to collection of PBMC and T cells. In an embodiment, the PBMC and T cells are collected from the donor between 1 and 30 days after the last dose of the SARS-cov2 vaccine. In an embodiment, the donor from whom the responder T cells are collected is a SARS-cov2 immune donor who is selected for donation based on the level of SARS-cov2 specific antibodies (e.g., level of IgG antibodies against SARS-cov2) or percentage of SARS-cov2 reactive CD4 and CD8 T cells as determined by methods known in the art (Grifoni et al., 2020, Cell Host & Microbe 27, 671-680). In an embodiment, the donor is selected based on the level of SARS-cov2 specific antibodies that are at least 20% higher than a reference control (i.e., a subject who is not SARS-cov2 immune). In an embodiment, the donor is selected based on the level of SARS-cov2 specific T cells (CD4 or CD8 T cells) that are at least 20% higher than a reference control (i.e., a subject who is not SARS-cov2 immune). In an embodiment, the donor is selected based on the level of SARS-cov2 specific IgG antibodies that are in the top 20, 30, 40, 50, 60, 70, 80, 90 percentile of the SARS-cov2 immune subjects. In an embodiment, the donor is selected if they show level of SARS-cov2 specific T cells (Cat or CD8 T cells) that are at least 20% higher than a reference control (i.e., a subject who is not SARS-cov2 immune). In an embodiment, the donor is selected if they show level of SARS-cov2 specific T cells (CD4 or CD8 T cells) that are in the top 20, 30, 40, 50, 60, 70, 80, 90 percentile of the SARS-cov2 immune subjects.

In another embodiment, the donor from whom the responder T cells are collected is not a SARS-cov2 immune donor.

The responder T cells may be isolated from PBMC by any suitable method, of which many are well known in the art. In an embodiment, the "stimulator" cells (e.g., PBMCs, I cells or BLCLs) are obtained from the same cell population (e.g., PBMC sample) as are the "responder" cells such that they are identically HLA-matched. For example, a PBMC sample from a donor is split into a "stimulator" cell fraction and a "responder" cell fraction, wherein the responder cells may be enriched for CD3$^+$ cells; and stimulator cells are transduced or infected so as to present particular SARS-cov2 antigens on the cell surface. In an alternate embodiment, the PBMC sample from a donor is enriched for CD3$^+$ cells, which are then split into "stimulator" cell fraction and a "responder" cell fraction. The "stimulator" CD3$^+$ cell fraction is transduced or infected so as to present particular SARS-cov2 antigens on the cell surface. Optionally, the stimulator cell fraction may be enriched by methods known in the art prior to transduction/infection, such as by selection for CD19$^+$ cells. Thus, the SARS-cov2 antigen-presenting cells (e.g., PBMCs, CD3$^+$T cells, or BLCLs) will present the SARS-cov2 antigen to responder T cells (e.g., CD3$^+$-enriched cells), thus activating and inducing proliferation of SARS-cov2 antigen-specific T cells. In some such embodiments, the responder T cells (e.g., isolated T cells) are transduced with a SABR-encoding vector prior to presentation of SARS-cov2 antigen by the stimulator fraction (e.g., PBMCs, CD3⁺T cells, or BLCLs). In certain embodiments, the responder T cells (e.g., isolated. T cells) are transduced with a SABR-encoding vector after presentation of SARS-cov2 antigen by the stimulator fraction (e.g., PBMCs, CD3⁺T cells, or BLCLs). In alternate embodiment, cell lines (e.g., aK562, JEMO-1, REC-1 etc.) can be transduced or infected so as to present particular SARS-cov2 antigens on the cell surface and act as "stimulator" or antigen presenting cells.

Accordingly, provided herein are methods of generating allogeneic or autologous T cells that express a T cell receptor that specifically binds to, for example, an SARS-cov2 peptide presented on a class I or II MHC and further express a synthetic antigen binding receptor (SABR) that binds to a selected target (e.g., CD 19). In some embodiments, APCs are generated through viral infection of stimulator cells, e.g., by wild type/native SARS-cov2 or an adenoviral vector that encodes a polyepitope of defined CTL epitopes from SARS-cov2 Spike Glycoprotein, nucleocapside protein, membrane glycoprotein sequence or orf 1 ab. In some embodiments, the stimulator cells are mixed with non-infected, isolated T cells (responders) so as to present the SARS-cov2 polyepitopes to said T cells. In some embodiments, isolated, virus-specific T cells presented with SARS-cov2 polyepitopes are activated and induced for proliferation.

In some embodiments, the responder cells and the stimulator cells are each derived from peripheral blood mononuclear cells (PBMC). In some such embodiments, the responder cells and the stimulator cells are each derived from PBMCs from the same donor. In other embodiments, the responder cells and the stimulator cells are each derived from PBMCs from different donors. In other embodiments, the responder cells derived from PBMCs from a SARS-cov2 immune donor, e.g., a SARS-cov2 positive donor, e.g., a donor with history of infection with SARS-cov2 or a history of immunization with a SARS-cov2 vaccine. In some such embodiments, prior to contact with stimulator cells, responder cells are isolated and/or purified so as to consist essentially of T cells. In preferred embodiments, the responder cells are isolated and/or purified so as to consist essentially of CD3⁺ cells. Most preferably, the responder cells consist essentially of CD3⁺ T cells.

Prior to presentation to responder cells (e.g., T cells), stimulator cells may be infected with a native virus, such as SARS-cov2, thereby presenting viral antigens on their surface. In some embodiments, the stimulator cells are transduced with a viral vector, preferably an adenoviral vector or a lentiviral vector, comprising a nucleic acid sequence encoding a SARS-cov2 antigen. In some such embodiments, the adenoviral vector is replication incompetent. More preferably, the vector comprises a nucleic acid sequence encoding one or more SARS-cov2 antigens. The one or more SARS-cov2 antigens may comprise a Spike Glycoprotein (SEQ II) NO: 231 and SEQ ID NO: 701) or fragment thereof (e.g., S1-RBD), S2 protein (SEQ ID NO: 694) or fragment thereof, a nucleocapsid polypeptide (SEQ ID NO: 232 and SEQ ID NO: 702) or fragment thereof, membrane glycoprotein (SEQ ID NO: 233 and SEQ ID NO: 703) or fragment thereof, orf3 (SEQ ID NO: 234 and 704) or fragment thereof and/or orf 1 ab or fragment thereof. In an embodiment, the SARS-cov2 antigen is the receptor binding domain of the Spike glycoprotein (S1-RBD) (SEQ ID NO: 230 and 700). In an embodiment the S1-RBD is expressed on the cell surface in fusion with a heterologous transmembrane domain or a membrane anchoring domain. The nucleic acid and amino acid sequence of an exemplary S1-RBD fusion protein comprising the S1-RBD in fusion with the hinge and transmembrane domains of mouse CD8 are presented in SEQ ID NO:229 and 699, respectively.

In an embodiment, the one or more SARS-cov2 antigens are expressed in fusion with a protein degradation domain, such as ubiquitin or a ubiquitin mutant. An exemplary ubiquitin mutant is ubiquitin G67A. The protein degradation domain may be fused to the amino or the carboxy terminus of the one or more SARS-cov2 antigens.

In an embodiment, the one or more SARS-cov2 antigen proteins are expressed in fusion with a drug inducible protein degradation domain (DIPDD). Exemplary DIPDD include FKBP12-F36V (SEQ ID NO: 1161), IKZF1-ZF2-145-167 (SEQ ID NO: 1162), IKZF1-ZF2-ZF3-145-197 (SEQ ID NO: 1162) and IKZF1-ZF2-ZF3-145-243 (SEQ ID NO: 1163). The DIPDD can be attached to the N- or the C-terminus of the SARS-cov2 encoded proteins and/or polyepitopes. Exemplary SARS-cov2 proteins and polyepitopes in fusion with the different DIPDD are represented by SEQ ID NO: 1176-1195. The proteins carrying the FKBP12-F36V (SEQ ID NO: 1161) DIPDD are degraded by addition of dTAG13 and its homologs, while proteins carrying IKZF1-ZF2-145-167 (SEQ ID NO: 1162), IKZF1-ZF2-ZF3-145-197 (SEQ ID NO: 1162) and IKZF1-ZF2-ZF3-145-243 (SEQ ID NO: 1163) are degraded by the addition of IMiDs (immune modulatory drugs), such as pomalidomide, lenalidomide, CC220, and CC885. Other DIPDDs are known in the art and can be used in alternate embodiment of the disclosure. In an embodiment, the stimulator cells expressing the SARS-cov2 antigen-DIPDD fusions are treated with dTAG13 or IMIDs in vitro. In an embodiment, the stimulator cells expressing the SARS-cov2 antigen-DIPDD fusions are treated with dTAG13 or IMIDs in vivo. In an embodiment, treatment with dTAG13 or IMIDs is carried out for between 1-30 days. In an embodiment, cell are treated with dTAG13 or its homologs at concentration of between 1 nM to 1 μM. In an embodiment, cell are treated with IMIDs at concentration of between 10 pM to 1 μM.

In an embodiment, the vector encodes poly epitope derived from different antigens of SARS-cov2, such as spike glycoprotein, nucleocapsid and membrane glycoprotein, orf3a and/or orf 1 ab. In an embodiment, the vector encodes a poly epitope of defined CTL epitopes from spike glycoprotein, nucleocapsid and membrane glycoprotein, orf3a and/or orf 1 ab. An exemplary poly epitope derived from SARS-cov2 antigens that are presented by HLA-A0201 is represented by nucleic acid and amino acid SEQ II) NO: 225 and 695, respectively. In an embodiment, the vector encodes a poly epitope of defined cm epitopes from spike glycoprotein, nucleocapsid and membrane glycoprotein and/or orf 1 ab fused to ubiquitin or a mutant thereof. An exemplary ubiquitin mutant is ubiquitin G67A (SEQ ID NO: 212 and SEQ ID NO: 682). The protein degradation domain may be fused to the amino or the carboxy, terminus of the one or more SARS-cov2 antigens or polyepitopes. An exemplary poly epitope derived from SARS-cov2 antigens that is presented by HLA-A0201 and in fusion with a Ub-G67A mutant is represented by nucleic acid and amino acid SEQ ID NO: 226 and 696, respectively. An exemplary poly epitope derived from SARS-cov2 antigens that is presented by HLA-DRB10401 is represented by nucleic acid and amino acid SEQ ID NO: 227 and 697, respectively. An exemplary poly epitope derived from SARS-cov2 antigens that is presented by HLA-DRB10401 and in fusion with a Ub-G67A mutant is represented by nucleic acid and amino acid SEQ ID NO: 228 and 698, respectively. In an embodiment, the vector encodes a poly epitope derived from spike glycoprotein, nucleocapsid and membrane glycoprotein and/or orf 1 ab fused to one or more proteins encoded by SARS-cov2. In an embodiment, the vector encodes a poly epitope of defined CTL epitopes from nucleocapsid and membrane glycoprotein fused to Spike Glycoprotein.

In some embodiments, the stimulator cells are incubated with one or more cytokines prior to culturing with (i.e., presentation to) responder cells (e.g., non-infected PBMC or CD3+ enriched cells). Such stimulator cells may comprise B cells (e.g., BLCLs), antigen-presenting T-cells, dendritic cells, artificial antigen-presenting cells, and/or aK562 cells. In preferred embodiments, the stimulator cells are antigen-presenting BLCLs. In some embodiments, the stimulator cells also express a module that results in NF-κB activation. Exemplary module that results in NF-κB activation is vFLIP K13 (SEQ ID NO: 199 and SEQ ID NO: 669) and hNEMO-K277A.

Though antigen-specific cells achieve activation and proliferation when presented with antigen by the stimulator fraction, such stimulator cells are not desirable in the final harvested SABR-T cell product. Moreover, in order to minimize the risk of any viral recombination events in proliferating cells leading to formation of competent virus, the stimulator cells are treated and/or modified prior to culturing with responder T cells so as to inhibit proliferation, e.g., by irradiation with gamma rays or exposure to an agent such as mitomycin C. For example, in such culture conditions, responder cells (e.g., I-cells) are presented with peptide antigens by non-proliferating stimulator cells. In some such embodiments, the culture is maintained from at least 24 hours to at least 28 days prior to transduction with a SABR-encoding vector. In some embodiments, the culture is maintained for at least 24 hours, at least 2 days, at least 3 days, at least 4 days, at least 0.5 days, at least 6 days, at least 7 days, at least 8 days, at least 9 days, at least 9 days, at least 10 days, at least 11 days, at least 12 days, at least 13 days, at least 14 days, at least 17 days, or at least 28 days prior to transduction with a SABR-encoding vector. Preferably, the culture is maintained for at least 2 days after antigen presentation by stimulator cells prior to transduction with a SABR-encoding vector, Most preferably, the culture is maintained for at least 6 days after antigen presentation by stimulator cells prior to transduction with a SABR-encoding vector. In further embodiments, the culture is maintained from at least 24 hours to at least 28 days following transduction with a SABR-encoding vector. In certain embodiments, the culture is maintained for at least 24 hours, at least 2 days, at least 3 days, at least 4 days, at least 5 days, at least 6 days, at least 7 days, at least 8 days, at least 9 days, at least 9 days, at least 10 days, at least 11 days, at least 12 days, at least 13 days, at least 14 days, at least 17 days, or at least 28 days following transduction with a SABR-encoding vector. In some embodiments, the culture is re-seeded and/or re-stimulated as necessary.

For example, responder T cells undergo at least a first stimulation step (i.e., presented with antigen on APCs) and may be re-seeded and/or re-stimulated as needed (i.e., a second time or more). Said re-seeded and/or re-stimulated culture is maintained for at least 24 hours, at least 3 days, at least 9 days, at least 11 days, at least 14 days, at least 17 days, or at least 28 days prior to/or following transduction with a SABR-encoding vector. In preferred embodiments, a responder cell culture is stimulated at least once prior to transduction with a SABR-encoding vector. More preferably, the responder culture is stimulated multiple times, wherein subsequent stimulation steps are separated by anywhere from 2 to 14 days. For example, a culture undergoing a first stimulation may undergo a second stimulation (e.g., re-stimulation) 11 days after the first stimulation; optionally, a third stimulation (e.g., re-stimulation) is initiated 7 days after the second stimulation step. A culture undergoing a stimulation step (e.g., re-stimulation) is maintained for at least 1 to 10 days before transduction with a SABR-encoding vector. Preferably, the culture is maintained for at least 2 days before transduction with a SABR-encoding vector. Most preferably, the culture is maintained for at least 6 days after antigen presentation by stimulator cells prior to transduction with a SABR-encoding vector. Optionally, an NK depletion step is employed prior to stimulation. For Example, CD56+ cells may be depleted from culture (e.g. with anti-CD56 beads) immediately prior to stimulation by APCs.

In certain embodiments, after at least a first presentation of antigen to achieve activation and proliferation, the SARS-cov2 antigen-specific T-cells may be frozen and stored prior to and/or following transduction with a SABR-encoding vector, to be thawed at a future date. In some embodiments, said thawed culture is re-stimulated and/or re seeded as necessary, and said re-stimulated and/or re-seeded culture is maintained for at least 24 hours, at least 2 days, at least 3 days, at least 9 days, at least 11 days, at least 14 days, at least 17 days, or at least 28 days prior to/or following transduction with a SABR-encoding vector as described herein. Likewise, in such cases wherein the culture is re stimulated multiple times, subsequent stimulation steps are separated by anywhere from 2 to 14 days, as described herein.

The activation and proliferation of antigen-specific T cells also requires a sufficient amount of antigen-presentation by stimulator cells. Accordingly, the stimulation cultures contemplated herein (e.g., including re-stimulation cultures) comprise known ratios of responder cells to simulator cells. For example, the ratio of responder cells to simulator cells is about 0.1:1 to about 20:1. For example, and without limitation, in preferred embodiments, the initial stimulation comprises a responder: stimulator ratio of about 0.43:1. A subsequent stimulation (e.g., re stimulation) may comprise a responder: stimulator ratio of 0.25:1 and a yet further stimulation (e.g., re-stimulation) comprises a responder: stimulator ratio of 4:1.

In certain aspects, provided herein are methods of generating allogeneic or autologous SABR-T cells expressing TCRs that specifically bind to peptides (e.g., antigens) comprising T cell epitopes presented on MHC (e.g. class I MHC), and SABRs that bind to a selected target, such as a disease-associated peptide target, for treating autoimmune disorders and cancers (e.g., MS, SAD, IBD, and/or CD19+ B-cell malignancies, lymphomas, leukemias, and/or solid tumors). Contemplated herein are T cells suitable for the production of SABR-T cells generated by incubating a sample comprising T cells (e.g., a PBMC sample or CD3+ cells isolated therefrom) with antigen-presenting cells (APCs) that present one or more of the T cell epitopes described herein (e.g., APCs that present a peptide described herein comprising a SARS-cov2 epitope on a MHC complex, such as SARS-cov2-infected or recombinantly transduced BLCLs, T cells or aK562).

In some embodiments, the peptides comprising a T cell epitope, as described herein, comprise epitope from SARS-cov2. In some embodiments, the epitopes are HLA class restricted T cell epitopes. In other embodiments, the epitopes are HLA class H-restricted.

The peptides provided herein may comprise a sequence of any SARS-cov2 viral protein (e.g., a sequence of at least 5, 6, 7, 8, 9, 10, 11, 12, 13, 14, 15, 16, 17, 18, 19 or 20 contiguous amino acids of any SARS-cov2 protein). In some embodiments, the peptides provided herein comprise no more than 25, 20, 19, 18, 17, 16, 15, 14, 13, 12, 11 or 10 contiguous amino acids of the SARS-cov2 viral protein.

The peptides provided herein may comprise a sequence of Spike Glycoprotein (e.g., a sequence of at least 5, 6, 7, 8, 9, 10, 11, 12, 13, 14, 15, 16, 17, 18, 19 or 20 contiguous amino acids of Spike Glycoprotein). In some embodiments, the peptides provided herein comprise no more than 25, 20, 19, 18, 17, 16, 15, 14, 13, 12, 11 or 10 contiguous amino acids of Spike Glycoprotein. Several variants of Spike glycoprotein have been isolated and are covered in alternate embodiment of the disclosure. An exemplary Spike Glycoprotein amino acid sequence is provided in SEQ ID NO: 701.

In some embodiments, the peptides provided herein comprise a sequence of SARS-cov2 nucleocapsid phosphoprotein (e.g., a sequence of at least 5, 6, 7, 8, 9, 10, 11, 12, 14, 15, 16, 17, 18, 19 or 20 contiguous amino acids). In some embodiments, the peptides provided herein comprise no more than 25, 20, 19, 18, 17, 16, 15, 14, 13, 12, 11 or 10 contiguous amino acids of SARS-cov2 nucleocapsid phosphoprotein. An exemplary SARS-cov2 nucleocapsid phosphoprotein amino acid sequence is provided in SEQ ID NO: 702.

In some embodiments, the peptides provided herein comprise a sequence of SARS-cov2 membrane glycoprotein (e.g., a sequence of at least 5, 6, 7, 8, 9, 10, 11, 12, 13, 14, 15, 16, 17, 18, 19 or 20 contiguous amino acids of SARS-cov2 membrane glycoprotein). In some embodiments, the peptides provided herein comprise no more than 25, 20, 19, 18, 17, 16, 15, 14, 13, 12, 11 or 10 contiguous amino acids of SARS-cov2 membrane glycoprotein. An exemplary SARS-cov2 membrane glycoprotein amino acid sequence is provided in SEQ ID NO: 703.

Preferably, the peptide comprises the sequence of an epitope listed in Table 13,

TABLE 13

MHC RESTRICTED SARS-cov2 PEPTIDEs

| NAME | SEQ ID NO | SEQUENCE | MHC restriction |
|---|---|---|---|
| SARS-cov2-S-Prt-Pep1 | 980 | KLPDDFTGCV | HLA-A*0201 |
| SARS-cov2-S-Prt-Pep2 | 981 | ILPDPSKPS | HLA-A*0201 |
| SARS-cov2-S-Prt-Pep3 | 982 | VLNDILSRL | HLA-A*0201 |
| SARS-cov2-S-Prt-Pep4 | 983 | VVFLHVTYV | HLA-A2 |
| SARS-cov2-S-Prt-Pep5 | 984 | LITGRLQSL | HLA-A2 |
| SARS-cov2-S-Prt-Pep6 | 985 | FIAGLIAIV | HLA-A2 |
| SARS-cov2-S-Prt-Pep7 | 986 | RLNEVAKNL | HLA-A*0201 |
| SARS-cov2-S-Prt-Pep8 | 987 | NLNESLIDL | HLA-A*0201 |
| SARS-cov2-S-Prt-Pep9 | 988 | ALNTLVKQL | HLA-A*0201 |
| SARS-cov2-S-Prt-Pep10 | 989 | SIIAYTMSL | HLA-A*0201 |
| SARS-cov2-S-Prt-Pep11 | 990 | IRGWIFGTTLDSKTQSLL | DRB1*04:01 |
| SARS-cov2-S-Prt-Pep12 | 991 | CTFEYVSQPFLMD | DRB1*04:01 |
| SARS-cov2-S-Prt-Pep13 | 992 | QPFLMDLEGKQGN | DRB1*04:01 |
| SARS-cov2-S-Prt-Pep14 | 993 | TRFQTLLALHRSYLTPG DSSSGW | DRB1*04:01 |
| SARS-cov2-S-Prt-Pep15 | 994 | KSFTVEKGIYQTSNFRV Q | DRB1*04:01 |
| SARS-cov2-S-Prt-Pep16 | 995 | KSFTVEKGIYQTSNFRV Q | DRB1*07:01 |
| SARS-cov2-S-Prt-Pep17 | 996 | SASFSTFKCYGVSPTKL | DRB1*07:01 |
| SARS-cov2-S-Prt-Pep18 | 997 | SASFSTFKCYGVSPTKL | DR8 |
| SARS-cov2-S-Prt-Pep19 | 998 | QLIRAAEIRASANLAATK | DRB1*04:01 |
| SARS-cov2-S-Prt-Pep20 | 999 | HWFVTQRNFYEPQII | DRB1*04:01 |
| SARS-cov2-S-Prt-Pep21 | 1000 | NLDSKVGGNYNYLYRL FR | Class II |
| SARS-cov2-S-Prt-Pep22 | 1001 | LLNKHIDAYKTFP | HLADR2, DR3 |
| SARS-cov2-S-Prt-Pep23 | 1002 | LQLPQGTTL | HLA-A*0201 |

TABLE 13-continued

| MHC RESTRICTED SARS-cov2 PEPTIDEs | | | |
|---|---|---|---|
| NAME | SEQ ID NO | SEQUENCE | MHC restriction |
| SARS-cov2-Nucleocapsid-Pep1 | 1003 | ALNTPKDHI | HLA-A*0201 |
| SARS-cov2-Nucleocapsid-Pep2 | 1004 | GDAALALLL | HLA-B*4001 |
| SARS-cov2-Nucleocapsid-Pep3 | 1005 | LLLDRLNQL | HLA-A*0201 |
| SARS-cov2-Nucleocapsid-Pep4 | 1006 | RLNQLESKM | HLA-A*0201 |
| SARS-cov2-Nucleocapsid-Pep5 | 1007 | GMSRIGMEV | HLA-A*0201 |
| SARS-cov2-Nucleocapsid-Pep6 | 1008 | LALLLLDRL | HLA-A*0201 |
| SARS-cov2-Nucleocapsid-Pep7 | 1009 | GDAALALLLL | HLA-A*0201 |
| SARS-cov2-Nucleocapsid-Pep8 | 1010 | LLLLDRLNQL | HLA-A*0201 |
| SARS-cov2-Nucleocapsid-Pep9 | 1011 | TKAYNVTQAF | HLA-B*1525 |
| SARS-cov2-Nucleocapsid-Pep10 | 1012 | NFKDQVILL | HLA-A*2402 |
| SARS-cov2-Nucleocapsid-Pep11 | 1013 | KTFPPTEPK | HLA-A*1101 |
| SARS-cov2-Nucleocapsid-Pep12 | 1014 | MEVTPSGTWL | HLA-B*4001 |
| SARS-cov2-Nucleocapsid-Pep13 | 1015 | TKAYNVTQAF | Class I |
| SARS-cov2-Nucleocapsid-Pep14 | 1016 | NFKDQVILL | A*24:02 |
| SARS-cov2-Membrane-Glycoprt-Pep1 | 1017 | TLACFVLAAV | HLA-A*0201 |
| SARS-cov2-Membrane-Glycoprt-Pep2 | 1018 | GLMWLSYFI | HLA-A*0201 |
| SARS-cov2-Membrane-Glycoprt-Pep3 | 1019 | HLRIAGHHL | HLA-B*1502 |
| SARS-cov2-Membrane-orf1ab-pep1 | 1020 | CLEASFNYL | HLA-A*0201 |
| SARS-cov2-Membrane-orf1ab-pep2 | 1021 | WLMWLIINL | HLA-A*0201 |
| SARS-cov2-Membrane-orf1ab-pep3 | 1022 | ILLLDQALV | HLA-A*0201 |
| SARS-cov2-Membrane-orf1ab-pep4 | 1023 | SACVLAAEC | HLA-A*0201 |
| SARS-cov2-Membrane-orf1ab-pep5 | 1024 | SLPGVFCGV | HLA-A*0201 |
| SARS-cov2-Membrane-orf1b-pep6 | 1025 | TLMNVLTLV | HLA-A*0201 |
| SARS-cov2-Membrane-orf1ab-pep7 | 1026 | SMWALIISV | HLA-A*0201 |
| SARS-cov2-Membrane-orf3a-pep1 | 1027 | RIFTIGTVTLKQGEI | B*58:01 |
| SARS-cov2-Membrane-orf3a-pep1 | 1028 | TVTLKQGEI | B*58:01 |

In some embodiments, the peptides provided herein comprise two or more of the T cell epitopes (e.g., viral epitopes). In some embodiments, the peptides provided herein comprise at least 2, 3, 4, 5, 6, 7, 8, 9, 10, 11, 12, 13, 14, 15, 16, 17, 18, 19 or 20 T cell epitopes. For example, in some embodiments, the peptides provided herein comprise two or more of the T cell epitopes connected by linkers (e.g., polypeptide linkers). In some embodiments, the polypeptide or protein further comprises an intervening amino acid sequence between at least two of the plurality of epitopes. In some embodiments, the intervening amino acids or amino acid sequences are proteasome liberation amino acids or amino acid sequences. Non-limiting examples of proteasome liberation amino acids or amino acid sequences are or comprise AD, K or R. In some embodiments, the intervening amino acids or amino acid sequence are TAP recognition motifs. Typically, TAP recognition motifs may conform to the following formula: (R/N:I/Q:W/Y)n where n is any integer >1. Non-limiting examples of TAP recognition motifs include RIW, RQW, MIW and NQY, In some embodiments, the epitopes provided herein are linked or joined by the proteasome liberation amino acid sequence and, optionally, the TAP recognition motif at the carboxyl terminus of each epitope. Exemplary SARS-cov2 polyepitopes containing proteasome liberation sequences and TAP recognition motifs are presented in SEQ NO: 695 and SEQ ID NO:697.

In an embodiment, the one or more SARS-cov2 polyepitopes are expressed in fusion with a drug inducible protein degradation domain (DIPDD).

In some embodiments, the sequence of the peptides comprises a SARS-cov2 viral protein sequence except for 1 or more (e.g., 1, 2, 3, 4, 5, 6, 7, 8, 9, 10 or more) conservative sequence modifications.

In some embodiments, the peptides provided herein comprise a sequence that is at least 80%, 85%, 90%, 95% or 100% identical to a protein sequence (e.g., the sequence of a fragment of a viral protein).

The peptide can be a chimeric or fusion peptide. Exemplary SARS-cove polyepitopes containing proteasome liberation sequences and TAP recognition motifs are presented in SEQ ID NO: 695 and SEQ ID NO:697. In some embodiments, the peptide provided herein is linked to another peptide comprising a distinct epitope.

In certain aspects, provided herein are nucleic acid molecules encoding the peptides described herein. In some embodiments, the nucleic acid molecule is a vector. In some embodiments, the vector provided herein encodes at least 2, 3, 4, 5, 6, 7, 8, 9, 10, 11, 12, 13, 14, 15, 16, 17, 18, 19 or 20 epitopes provided herein (e.g., epitopes provided in Table 13). In some embodiments, the vector is a viral vector (e.g. a lentiviral vector).

In some embodiments, provided herein are cells that contain a nucleic acid described herein (e.g., a nucleic acid encoding a peptide described herein).

SABR-T Cells

Provided herein are methods of treating cancers, autoimmune diseases (e.g., MS, SAD, IBD) and infectious diseases (e.g., HIV-1, SARS, MERS, SARS-cov2, influenza, EBV, CMV etc.) by administering to the subject allogeneic or autologous SABR-T cells expressing a T cell receptor that specifically binds to an antigen (e.g., a virus peptide antigen) presented on a or major histocompatibility complex (MHC) molecule, and a synthetic antigen binding receptor molecule with the ability to both specifically bind a selected target peptide (e.g., a WT1 peptide, or Ras peptide, or NY-ESO peptide) or protein (e.g., CD19, CD20, CD22, CD33, CD123, Mesothelin, BCMA, CD70, Her2, PSMA, CD38, CD138, MPL etc.) and transduce subsequent activation signals.

In some embodiments, the antigen-specific T cells used for generating the SABR-T cells of the invention are selected from a cell bank or library. Preferably, the MHC is a class I MHC. In certain embodiments, the MHC is a class II MHC and has an a (or α) chain polypeptide that is HLA-DMA, HLA-DOA, HLA-DPA, HLA-DQA or HLA-DRA. In some such embodiments, the class II MHC has a b (or β) chain polypeptide that is HLA-DMB, HLA-DOB, HLA-DPB, HLA-DQB or HLA-DRB. Such T cells, as described herein (e.g., antigen-specific T cells and antigen-specific T cells expressing a SABR), are stored in a cell library or bank before they are administered to the subject.

Also provided herein are APCs that present a peptide described herein (e.g. a peptide comprising a T cell epitope). In some embodiments the APCs are B cells, antigen presenting T-cells, dendritic cells, or artificial antigen-presenting cells (e.g., aK562 cells).

In certain preferred embodiments, the APCs are derived from lymphoblastoid cells, such as BLCLs. Exemplary antigen-presenting BLCLs are described in O'Reily et al., Immunol Res 2007 38:237-250 and Koehne et al., Blood 2002 99: 1730-1740, which are hereby incorporated by reference. Dendritic cells for use in the process may be prepared by taking PBMCs from a patient sample and adhering them to plastic. In some embodiments, the APC is an artificial antigen-presenting cell, such as an aK562 cell.

In certain aspects, provided herein are methods of generating APCs that present the one or more of the T cell epitopes described herein comprising contacting an APC with a SARS-cov2 peptide comprising an epitope and/or with a nucleic acid encoding said epitope. In an embodiment, the SARS-cov2 proteins and/or peptides are presented to APC as fusion with an amphiphile. In some embodiments, the APCs are irradiated. A cell presenting a peptide described herein can be produced by standard techniques known in the art.

In some embodiments, provided herein are T cells (e.g., CD4 T cells and/or CD8 T cells) that express a TCR (e.g., an αβ TCR or γδ TCR) that recognizes a SARS-cov2 peptide described herein presented on a MHC. In some embodiments, the T cell is a CD8 T cell (a CTL) that expresses a TCR that recognizes a SARS-cov2 peptide described herein presented on a class I MHC. In some embodiments, the T cell is a CD4 T cell (a helper T cell) that recognizes a SARS-cov2 peptide described herein presented on a class II MHC.

In some embodiments, provided herein are methods of generating, activating and/or inducing proliferation of SABR-T cells that recognize one or more of the SARS-cov2 epitopes described herein and also express a synthetic antigen binding receptor (e.g., SARS-cov2-specific, antiCD19-SABR-T cells). In some embodiments, a culture (or sample thereof) comprising T cells (i.e., isolated T cells) is incubated in culture with an APC provided herein (e.g., an APC that presents a peptide comprising an SARS-cov2 epitope on a class I MHC complex, such as the virally transduced PBMCs described herein). In some embodiments, the APCs are autologous to the subject from whom the T cells were obtained. In some embodiments, the APCs are not autologous to the subject from whom the T cells were obtained. In some embodiments, the sample containing cells are incubated 2 or more times with APCs provided herein. In some embodiments, the T cells (and/or SABR-T cells) are incubated with the APCs in the presence of at least one cytokine. In some embodiments, the cytokine is IL-2, IL-4, IL-7 and/or IL-15. Similarly, T cell and/or SABR-T cell cultures may be maintained in the presence at least one cytokine, such as IL-2, IL-7 and/or IL-15. Exemplary methods for inducing proliferation of T cells using APCs are provided, for example, in U.S. Pat. Pub. No. 2015/0017723, which is hereby incorporated by reference. In preferred embodiments, such antigen-specific (e.g., SARS-cov2-specific) T cells are transduced with a vector comprising nucleic acid sequence encoding a synthetic antigen binding receptor (SABR).

Exemplary antigens targeted by SABR include, but are not limited to, tumor antigens, i.e., proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, Non-limiting examples of target antigens include: CD5; CD19; CD123; CD22; CD30; CD171; CS1 (also referred to as CD2 subset 1, CRACC, MPL, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8)aNeu5Ac(2-3)bD-Galp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms Like Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); 137113 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha (FRa or FR1); Folate receptor beta (FRb); Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin 132; fibroblast activation protein alpha (FAP); insulin-like growth factor 1 receptor (IGF-1 receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); sialyl Lewis adhesion molecule (sLe); ganglioside GM3 (aNeu5Ac(2-3)bD-Clalp(1-4)bDGlcp(1-1)Cer); transglutaminase 5 (TGS5); high molecular weight-melanoma associated antigen (HMWMAA); o-acetyl-GD2 ganglioside (OAcGD2); tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CM79a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LADE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin Bl; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of Imprinted Sites), Squamous Cell Carcinoma Antigen Recognized. By T Cells 3 (SART3); Paired box protein Pax-5 (PAX5); proacrosin binding protein sp32 (OY-TESl); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RUE); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A), bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1); MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen); Fucosyl-GM1, PTK7, gpNMB, CDH1-CD324, DLL3, CD276/B7H3, IL11Ra, IL13Ra2, CD179b-IGLl1, TCRgamma-delta, NKG2D, CD32 (FCGR2A), Tn ag, Tim1-/HVCR1, CSF2RA (GM-CSFR-alpha), TGF-betaR2, Lews Ag, TCR-beta1 chain, TCR-beta2 chain, TCR-gamma chain, TCR-delta chain, FITC, Leutenizing hormone receptor (LHR), Follicle stimulating hormone receptor (FSHR), Gonadotropin Hormone receptor (CGHR or GR), CCR4, GD3, SLAMF6, SLAMF4, HIV1 envelope glycoprotein, CMV pp65, EBV-EBNA3c, KSHV K8.1, KSHV-gH, influenza A hemagglutinin (HA), GAD, PDL1, Guanylyl cyclase C (GCC), auto antibody to desmoglein 3 (Dsg3), auto antibody to desmoglein 1 (Dsg1), HLA, HLA-A, HLA-A2, HLA-B, HLA-C, HLA-DP, HLA-DM, HLA-DOA, HLA-DOB, HLA-DQ, HLA-DR, HLA-G, IgE, CD99, Ras G12V, Tissue Factor 1 (TF1), AFP, GPRC5D, Claudin18.2 (CLD18A2 or CLDN18A.2), P-glycoprotein, STEAP1, Liv1, Nectin-4, Cripto, gpA33, BST1/CD157, low conductance chloride channel, the antigen recognized by TNT antibody, CD229, Toso, BAFF-R, SARS-cov2 Spike glycoprotein and any combination thereof.

Also disclosed are polynucleotides and polynucleotide vectors encoding the disclosed target-specific SABRs that allow expression of said SABRs in the disclosed immune effector cells (e.g., T cells, e.g., SARS-cov2 specific T cells).

Nucleic acid sequences encoding the disclosed SABRs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding SABRs is typically achieved by operably linking a nucleic acid encoding the SABR polypeptide to a promoter, and incorporating the construct into an expression vector. The disclosed nucleic acid can be cloned into a number of types of vectors.

In another aspect, the disclosure provides an isolated SABR polypeptide molecule comprising one or more antigen binding domains (e.g., antibody or antibody fragment, a ligand or a receptor) that bind to antigens as described herein, and are jointed to one or more T cell receptor constant chains.

In order to assess the expression of a SABR polypeptide or portions thereof, the expression vector to be introduced into a cell (e.g., an antigen-specific T cell) can also contain either a selectable marker gene or a reporter gene or both to facilitate identification and selection of expressing cells from the population of cells sought to be transfected or infected through viral vectors. In some embodiments, the SABR-encoding vector comprises a nucleic acid sequence encoding an antibiotic-resistance gene such as blasticidin resistance (Blast) or puromycin resistance (PAC). In some such embodiments, the SABR T cells (e.g., the antigen-specific SABR T cells) are cultured in the presence of the selectable marker (e.g., blasticidin or puromycin), thereby allowing for selection and expansion of SABR-expressing T cells described herein.

Also provided herein are genetically engineered cells (such as T cells, NK cells, iPSC) comprising vectors encoding nucleic acids encoding SABR (including functional variants). In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. The cell can be an immune effector cell (e.g., a T cell or a NKT cell, or a combination thereof) or a stem/progenitor cell (e.g., iPSC) that can give rise to an immune effector cell or a synthetic T cell.

In some embodiments, the cell is an immune cell. Non-limiting examples of immune cells include T-cells and NK-cells. Further, non-limiting examples of T-cells include Tregs, CD8+ T cells, and CD4+ T cells. In one embodiment, the cell is a human T cell. In some embodiments, the cell is a human cell. In some embodiments, the cell is a dog cell.

In one embodiment, the cell is a T cell and the T cell is deficient in one or more of endogenous T cell receptor chains. In some embodiments, the cell in the methods is deficient in constant chains of endogenous T cell receptor α, β1, β2, pre-TCRα, γ or δ or combination thereof. In some embodiments, the cell in the methods is deficient in HLA antigens. In some embodiments, the cell in the methods is deficient in β2 microglobulin.

In some embodiments, the methods provided herein are directed to treating a cancer, infection (e.g., SARS-cov2) and/or an autoimmune disorder in a subject by administering to the subject autologous or allogeneic SABR-T cells as provided herein.

The methods of the present disclosure rely, in part, on the principles of T cell restriction to specific target antigens. For example, and without limitation, products and preparations comprising donor-derived CTLs targeted against antigens expressed by a virus, such as SARS-cov2, can be elicited on targeted antigen-presenting (e.g., stimulator) cell lines, including SARS-cov2-transformed B Lymphoblasts (BLCLs) or K562 cells expressing SARS-cov2 antigens. With respect to the disclosed virus-antigen-specific SABR T cell preparations, the target cells and/or recipients of the SABR-T products made by the methods provided herein, may be autologous or allogeneic. In an embodiment, in the case of allogeneic targets, the human leukocyte antigen (HLA) identity of the donor must be known and matched to the HLA identity of the target (i.e., cultured cell lines and/or recipients).

A preparation of SABR T cells may have a mixture of antigen-specific and non-specific CTLs.

Target cells for the assays disclosed herein are typically selected for their uniform phenotype and availability in large quantities. In certain embodiments, the target cell lines are antigen-presenting cells (APCs). In some such embodiments, the target cell lines are B cells, antigen-presenting T-cells, dendritic cells, or artificial antigen-presenting cells (e.g., aK562 cells). In certain embodiments, the target cell lines comprise peripheral blood mononuclear cells (PBMCs). In some such embodiments, the target cell lines are lymphoblasts. In certain preferred embodiments, the target cell lines are virally transformed. In preferred embodiments, the target cell lines comprise each of Phytohemagglutinin-stimulated peripheral blood lymphocytes (PHA-blasts/PHAbs) and Epstein-Barr virus-transformed B-lymphoblastoid cell lines (BLCLs).

In some embodiments, target cell lines comprise allogeneic cells. In some such embodiments, target cells carry Human Leukocyte Antigen (HLA) alleles that do not match the HLA alleles to which the SABR-T CTLs of the preparation are restricted. In other such embodiments, the target cells carry HLA alleles that are a partial match to the HLA alleles to which the SABR-T CTLs of the preparation are restricted. In still other such embodiments, the target cells carry HLA alleles that are a match to the HLA alleles to which the SABR-T CTLs of the preparation are restricted. In preferred embodiments, the SABR-T CTLs are restricted to HLA alleles of the target cells which encode MHC Class I proteins.

In other embodiments, the target cell lines comprise autologous cells. In some such embodiments the SABR-T CTL preparation is identified as suitable for use against target cells by confirming the ability of the preparation to lyse two or more autologous target cell lines at, above, or below predetermined thresholds.

In certain embodiments, the autologous or allogeneic SABR-T cells comprise central memory T cells (TCM e.g., at least 60%, 70%, 80% of the cells are Tcm cells. In some embodiments, the autologous or allogeneic SABR-T cells comprise a ratio of central memory T cells to effector memory cells (TCM:TEM) from at least 1:1 to at least 3:1, e.g. at least 1:1, 1.4:1, 2.5:1, or 3:1). In some such embodiments, the autologous or allogeneic SABR-T cells are predominantly CD4+ T cells. In some embodiments, the autologous or allogeneic SABR-T cells comprise at least 80% CD4+ SABR-T cells and at least 15% CD8+ SABR-T cells). In some embodiments, the autologous or allogeneic SABR-T cells comprise a ratio of CD4+ T cells to CD8+ T cells from at least 1:1 to at least 3:1, e.g., at least 1:1, 1.4:1, 2.5:1, or 3:1. In some of the methods described herein, allogenic T cells are selected from a cell bank (e.g., a pre-generated third party donor derived bank of epitope-specific T cells).

In some embodiments, provided herein are methods of treating a cancer in a subject by administering to the subject a therapeutic SABR-T cell preparation as described herein. In some embodiments, the methods provided herein can be used to treat any cancer.

In certain embodiment, the method is used to treat an infectious disease or autoimmune disease.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, the methods described herein include selecting allogeneic T cells from a cell bank (e.g., a pre-generated third party donor derived bank of epitope specific T cells). In some embodiments, the T cells are selected because they express a TCR restricted to a class I MHC that is encoded by an HLA allele that is present in the subject. In some embodiments, the T cells are selected if the T cells and subject share at least 2 (e.g., at least 3, at least 4, at least 5, at least 6) HLA alleles and the T cells are restricted through a shared HLA allele. In some embodiments, the method comprises testing the TCR repertoire of the pre-generated third-party-donor-derived epitope-specific T cells (i.e., allogeneic T cells) with flow cytometry. In some embodiments, epitope-specific T cells are detected using a tetramer assay, an ELISA assay, a western blot assay, a fluorescent microscopy assay, an Edman degradation assay and/or a mass spectrometry assay (e.g., protein sequencing). In some embodiments, the TCR repertoire is analyzed using a nucleic acid probe, a nucleic acid amplification assay and/or a sequencing assay.

In some embodiments, provided herein are compositions (e.g., therapeutic compositions) comprising T cells and/or APCs provided herein used to treat and/or prevent an autoimmune disease in a subject by administering to the subject an effective amount of the composition.

According to the invention, a lymphodepleting treatment is generally performed before administering the engineered immune cells to the patients. Such lymphodepleting treatment generally combines fludarabine and cyclophosphamide. As a preferred embodiment of the present invention, the lymphodepleting treatment can comprise an anti-CD52 antibody, such as alemtuzumab, alone or in combination. The lymphodepletion regimen may for instance combine cyclophosphamide, typically for 1 to 3 days, fludarabine for 1 to 5 days, and alemtuzumab from 1 to 5 days. More specifically, the lymphodepletion regimen can combine between cyclophosphamide 50 and 70 mg/kg/day, fludarabine between 20 and 40 mg/m2/day, and alemtuzumab 0.1 to 0.5 mg/kg/day.

According to the present methods, the above induction chemotherapy treatment and lymphodepletion steps are usually followed by a cell immunotherapy treatment using engineered immune cells.

The immune cells may originate from the patients (autologous engineered cells) or from donors (allogenic engineered immune cells). They are generally primary cells obtainable from leukapheresis or derived from iPS cells or cell lines. These Immune cells are generally population of lymphocytes, preferably NK or T-cells. The engineered immune cells of the present invention preferably express recombinant TCR or a SABR specific for an antigen marker. By "recombinant TCR" is meant that an exogenous TCR with a different specificity is introduced or expressed into the cell that partially or completely replace the expression of the endogenous TCR.

In one embodiment, the method includes administering a cell expressing the SABR molecule, as described herein, in combination with an agent which enhances the activity of a SABR-expressing cell, wherein the agent is a cytokine, e.g., IL-2, IL-7, IL-15, IL-21, or a combination thereof. The cytokine can be delivered in combination with, e.g., simultaneously or shortly after, administration of the SABR-expressing cell.

In other embodiments, the cells expressing a SABR molecule are administered in combination with an agent that ameliorates one or more side effects associated with administration of a cell expressing a SABR molecule.

SABR Targeting SARS-Cov2

In some embodiment, the disclosure also provides isolated nucleic acids encoding SABR, wherein the antigen specific domain of the SABR targets the spike glycoprotein of SARS-cov2. In an embodiment, the disclosure provides an isolated nucleic acid encoding SABR, wherein the antigen specific domain of the SABR targets the Receptor Binding domain of the spike glycoprotein of SARS-cov2. In exemplary embodiments, the nucleic acid sequences of SABR targeting the spike glycoprotein of SARS-cov2 are set forth in SEQ ID NOs: 310-365; 367-422; 424-479 (Tables 9-11).

In some embodiment, the disclosure also provides isolated polypeptides encoding SABR, wherein the antigen specific domain of the SABR targets the spike glycoprotein of SARS-cov2. In an embodiment, the disclosure provides isolated polypeptides encoding SABR, wherein the antigen specific domain of the SABR targets the Receptor Binding domain of the spike glycoprotein of SARS-cov2. In exemplary embodiments, the polypeptide sequences of SABR targeting the spike glycoprotein of SARS-cov2 are set forth in SEQ ID NOs: 780-835; 837-892; 894-949 (Tables 9-11).

The disclosure also provides novel vL, vH and scFv fragments targeting the spike glycoprotein of SARS-cov2 that can be used in the construction of single and double chain SABRs, including $2^{nd}$ generation CARs, single and double chain SIRs, single and double chain cTCRs, Ab-TCR, TFPs, TAC and the like. Exemplary vL, vH and scFv fragments and their CDRs are listed in Table 7A.

In some embodiments, the antigen specific domains of the SABRs targeting the Spike glycoprotein comprise one or more $V_L$ fragments described in Table 7A. In some embodiments, the polynucleotides encoding the one more $V_L$ fragments comprise, consist of or consist essentially of sequences set forth in any one or more of SEQ ID NOs: 213 to 215. In some embodiments, the polypeptides encoding the one more $V_L$ fragments comprise, consist of or consist essentially of sequences set forth in any one or more of SEQ ID NOS: 683 to 685 or sequences with 70-99% identity to sequences set forth in any one or more of SEQ ID NOS: 683 to 685 or sequences with 70-99% identity in the three complementarity determining regions (CDRs) to the sequences set forth in any one or more of SEQ ID NOS: 683 to 685 or sequences with less than 3 substitutions in the three CDRs of the sequences set forth in any one or more of SEQ ID NOS: 683 to 685 or sequences that bind to the same target antigens or the same epitopes on the target antigens as the sequences set forth in any one or more of SEQ ID NOS: 683 to 685. In some embodiments, the antigen specific domains of the CARs comprise one or more $V_H$ fragments described in Table 7a. In some embodiments, the polynucleotides encoding the one more $V_H$ fragments comprise, consist of or consist essentially of sequences set forth in any one or more of SEQ ID NOS: 217-219. In some embodiments, the polypeptides encoding the one more $V_H$ fragments comprise, consist of or consist essentially of sequences set forth in any one or more of SEQ ID NOS: 687-689 or sequences with 70-99% identity to sequences set forth in any one or more of SEQ ID NOS: 687-689 or sequences with 70-99% identity in the three complementarity determining regions (CDRs) to the sequences set forth in any one or more of SEQ ID NOS: 687-689 or sequences with less than 3 substitutions in the three CDRs of the sequences set forth in any one or more of SEQ ID NOS: 687-689 or sequences that bind to the same target antigens or the same epitopes on the target antigens as the sequences set forth in any one or more of SEQ ID NOS: 687-689.

Also provided are functional variants of the SABRs targeting SARS-cov2 described herein, which have substantial or significant sequence identity or similarity to a parent SABR, which functional variant retains the biological activity of the SABR of which it is a variant. Functional variants encompass, for example, those variants of the SABR described herein (the parent SABR) that retain the ability to recognize SARS-cov2-infected cells to a similar extent, the same extent, or to a higher extent, as the parent SABR. In reference to the parent SABR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent SABR.

A functional variant can, for example, comprise the amino acid sequence of the parent SABR with at least one conservative amino acid substitution. Alternatively or additionally, the functional variants can comprise the amino acid sequence of the parent SABR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent SABR.

The SABRs (including functional portions and functional variants) can be of any length, i.e., can comprise any number of amino acids, provided that the SABRs (or functional portions or functional variants thereof) retain their biological activity, e.g., the ability to specifically bind to SARS-cov3 spike glycoprotein, detect SARS-cov2 infected cells in a mammal, or treat or prevent SARS-cov2 associated disease (e.g., COVID-19) in a mammal, etc. For example, the SABR can be about 300 to about 5000 amino acids long, such as 300, 400, 500, 600, 700, 800, 900, 1000 or more amino acids in length.

Further provided herein are vectors encoding nucleic acids encoding SABR, wherein the antigen specific domain of the SABR targets spike glycoprotein of SARS-cov2.

Also provided herein are genetically engineered cells (such as T cells, NK cells, iPSC) comprising vectors encoding nucleic acids encoding SABR (including functional variants), wherein the antigen specific domain of the SABR targets spike glycoprotein of SARS-cov2. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. The cell can be an immune effector cell (e.g., a T cell or a NKT cell, or a combination thereof) or a stem/progenitor cell (e.g., iPSC) that can give rise to an immune effector cell or a synthetic T cell.

In some embodiments, the cells are a cell line. Exemplary cell lines that can be used to express a SABR of the disclosure targeting the spike glycoprotein of SARS-cov2 include NK92, NK92MI and the like.

In another aspect, the invention relates to a pharmaceutical composition comprising a cell or cell population (such as T cells, NK cells, iPSC) comprising vectors encoding nucleic acids encoding SABR, wherein the antigen specific domain of the SABR targets spike glycoprotein of SARS-cov2.

Cells that express a SABR of the invention are used in the treatment and prevention of SARS-cov2 infection and associated complications (e.g., COVID-19).

The disclosure provides methods of prevention and treatment of complications (e.g., COVID-19) arising from infection with viruses SARS-cov2 by treatment with a pharmaceutical composition targeting the spike glycoprotein of SARS-cov2 and comprising the cells described herein, the nucleic acids described herein, the polypeptides encoded by the nucleic acids described herein or vectors comprising the nucleic acids described herein, and a pharmaceutically acceptable carrier.

The invention thus relates to methods for the prevention and/or treatment of COVID-19, comprising administering to a subject a cell or cell population comprising a SABR as described herein, said method comprising administering, to a subject in need thereof, a pharmaceutically active amount of a cell and/or of a pharmaceutical composition of the invention. The invention also relates to a SABR, a cell or cell population comprising a SABR as described herein for use in therapy.

In another aspect, the invention relates to a method of providing an SARS-cov2 immunity in a subject, the method comprising administering to the mammal an effective amount of a cell or cell population genetically modified to express a SABR of the invention, wherein the antigen binding domain of SABR binds to spike glycoprotein of SARS-cov2.

In another aspect, the invention relates to a method for producing a genetically modified cell or cell population comprising expressing in said cell or cell population a SABR nucleic acid construct of the invention. The method may include introducing into the cell a nucleic acid as described herein (e.g., an in vitro transcribed RNA or synthetic RNA; an mRNA sequence encoding a SABR polypeptide as described herein). In embodiments, the RNA expresses the SABR polypeptide transiently. In one embodiment, the cell is a cell as described herein, e.g., an immune effector cell (e.g., T cells or NK cells, or cell population). Cells produced by such methods are also within the scope of the invention.

In another aspect, the invention relates to an ex vivo method for generating a population of cells for use in adaptive immunotherapy comprising transforming said cell with a SABR of the invention, Cell Lines for Sars-Cov2 Research and Development and Quality Control and Methods of Using the Same The disclosure also provides polynucleotides, polypeptides, vectors and primary cells and cell lines that express the different SARS-cov2 antigens and polyepitopes, singly or in combination. Exemplary SARS-cov2 antigens include spike glycoprotein and a fragment thereof, nucleocapsid protein and a fragment thereof membrane glycoprotein and a fragment thereof. Exemplary cell lines include K562, 293, VeroE6 and the like.

In an embodiment, the primary cells and cell line encodes poly epitope derived from different antigens of SARS-cov2, such as spike glycoprotein, nucleocapsid and membrane glycoprotein and/or orf 1 ab. In an embodiment, the SARS-cov2 antigens and polypeptides are expressed in the primary cells and cell lines stably. In an embodiment, the SARS-cov2 antigens and polypeptides are expressed in the primary cells and cell lines transiently. In an embodiment, the SARS-cov2 antigens and polypeptides are expressed in the primary cells and cell lines using a constitutive promoter (MND promoter, EF1α promoter, CMV promoter etc.). In an embodiment, the SARS-cov2 antigens and polypeptides are expressed in the primary cells and cell lines using an inducible promoter (e.g., tetracycline promoter). In an embodiment, the SARS-cov2 antigens and polypeptides are expressed in the primary cells and cell lines following infection with SARS-cov2. The disclosure also provides a method for the use of the primary cells and cell lines as antigen presenting cells (APC) for generation and expansion of SARS-cov2 reactive T cells. The disclosure also provides a method for the use of the primary cells and cell lines as antigen presenting cells (APC) for monitoring immune response to SARS-cov2 and for measuring the efficacy of therapeutics targeting SARS-cov2 (e.g., SARS-cov2 directed SABR, antibodies, antibody drug conjugates and the like).

In an embodiment, the primary cells and cell lines expressing the SARS-cov2 antigens and polyepitopes, singly or in combination, also express a luciferase. In an embodiment, the luciferase is a thermostable luciferase. Exemplary thermostable luciferase include marine luciferase (e.g., Gluc, NLuc, PaLuc, TurboLuc and the like) and thermostable beetle luciferase such as (e.g., LucPPE and its engineered variants such as LucPPe-146-1H2, LucPPe-133-1B2, LucPPe-78-0B10, LucPPe49-7C6A and LucPpL-81-6G1. The nucleic acid and amino acid. SEQ ID of exemplary luciferases are provided in Table 2.

Also provided herein are cell lines and/or compositions comprising primary cells and cell lines wherein the cell lines express one or more of SARS-cov2 antigens, antigen fragments, epitopes, polyepitopes, and also coexpress the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), *Renilla* Luc, Firefly luciferase (FfLuc or Fluc), LucPPe-146-1H2, LucPPe-133-1B2, LucPPe-78-0B10, LucPPe49-7C6A, LucPpL-81-6G1, CBGRluc, thermostable alkaline phosphatase or homologs or orthologs or mutants or derivatives thereof for the purpose of use as a target cell line for measuring cytotoxicity.

Also provided herein are primary cells and/or compositions comprising primary cells wherein the primary cells express one or more of SARS-cov2 antigens, antigen fragments, epitopes, polyepitopes, and also coexpress the non-secretory forms of GLuc, NLuc, MLuc7, HTLuc, PaLuc 1, PaLuc2, MpLuc1, McLuc1, MaLuc1, MoLuc1, MoLuc2, MLuc39, PsLuc1, LoLuc1-3, HtLuc2, TurboLuc16 (TLuc), *Renilla* Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or derivatives thereof.

In various embodiments, the primary cell and cell lines are modified and/or selected to lack the expression of one or more antigens.

The disclosure also provides a method for use of the primary cells and cell lines for measuring the cytotoxicity of SARS-cov2 directed therapeutics (e.g., T cells, SABR-T, antibodies, bispecific antibodies etc) using the non-radioactive luciferase based cytotoxicity assay (Matador cytotoxicity assay) as described in PCT/US17/52344, which is incorporated in its entirety by reference herein.

The methods include providing a target cell (e.g., a primary cell or cell line) that has been engineered to express a SARS-cov2 protein (e.g., Spike glycoprotein) or a fragment thereof and is optionally engineered to express intracellularly a reporter; exposing the target cell to SARS-cov2 directed agent capable of modulating cytotoxicity; and assaying the cytotoxicity of SARS-cov2 directed agent. In an embodiment, the cytotoxicity of the agent is measured by measuring the activity of the reporter. In one embodiment, the reporter is not expressed endogenously by the target cell. In another embodiment, the reporter is expressed endogenously by the target cell at a level lower than what is achieved by engineered expression. In an embodiment, the reporter is a thermostable luciferase. In one embodiment, a change in reporter activity relative to a reference value is indicative of the agent being able to modulate cytotoxicity of the target cell. In one embodiment, a change in reporter activity is an increase in reporter activity relative to a reference value. In some embodiments, the reporter is expressed endogenously by the target cell at a level that is at least 10-25%, 25-50%, 50-75% or 75-100% lower than what is achieved by engineered expression.

In on embodiment, the reporter activity is assayed in the cell media containing the target cells. In another embodiment, the reporter activity is assayed in the cell supernatant that is free of the target cells.

In various embodiments, the cytotoxicity of an agent is measured by obtaining (assaying) the reporter activity in cell pellet and cell free supernatant and normalizing the reporter activity measured in the cell free supernatant. In various embodiments, normalizing comprises dividing the activity in the cell free supernatant by the reporter activity measured in the cell pellet In various embodiments, the reporter is a non-secretory form of an enzyme that is stable under the assay conditions at 37° C. for more than 15 min, for more than 30 min, for more than 1 hour, for more than 2 hours, for more than 3 hours, for more than 4 hours, for more than 12 hours, 24 hours, for more than 36 hours, for more than 48 hours or for at least 96 hours.

In various embodiments, the reporter is a non-secretory form of a luciferase. In some embodiments, the non-secretory form of luciferase is obtained from copepods, deep sea shrimp, beetle, firefly, or homologs or orthologs thereof or mutants or variants or derivatives thereof.

In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata.*

In various embodiments, the luciferase is any one or more of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, *Renilla* Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or variants or derivatives thereof.

In various embodiments, the reporter is a non-secretory form of a luciferase obtained from copepods, deep sea shrimp, beetle, firefly or homologs or orthologs thereof or mutant or derivatives thereof and the reporter activity is assayed by exposing the target cells to a luciferase specific substrate.

In various embodiments, the luciferase-specific substrate is coelentrazine or an imidazopyrazinone substrate (furimazine) or a derivative thereof. In one embodiment, the luciferase-specific substrate is D-luciferin or a derivative thereof.

In one embodiment, the reporter is a thermostable luciferase. In one embodiment, the reporter is a thermostable beetle luciferase. In an embodiment, the thermostable beetle luciferase is obtained from *Photuris pennsylvanica* and *Pyrophorus plagiothalamus*

In some embodiments, the reporter is a non-secretory form of an alkaline phosphatase. In one embodiment, the alkaline phosphatase is a heat-stable alkaline phosphatase.

In some embodiments, the reporter is a non-secretory form of a fluorescent protein. In one embodiment, the non-secretory form of a fluorescent protein is green fluorescent protein.

In one embodiment, the target cells express a single type of reporter. In another embodiment, the target cells express more than one type of reporter. In various embodiments, the activity of the two reporters can be measured independent of each other either simultaneously or sequentially.

In some embodiments, the substrate for one of the reporters is coelentrazine or an imidazopyrazinone substrate (e.g., furimazine) or a derivative thereof and the substrate for the other reporter is D-luciferin or a derivative thereof.

In some embodiments, the substrate for one of the reporters is coelentrazine or an imidazopyrazinone substrate (e.g., furimazine) or a derivative thereof and the substrate for the other reporter is pNNP or a derivative thereof.

In some embodiments, the target cells expressing two or more reporters are mixed together prior to the assay.

In some embodiments, the reference value is the reporter activity in any one or more of (i) target cells that do not express reporter, (ii) target cells that express reporter but are not treated with the test agent(s); (iii) the target cells that are left untreated; (iv) target cells that are not treated with the substrate for the reporter, or (iii) a combination thereof.

In some embodiments, the agent capable of modulating cytotoxicity is any one or more of an antibody, small molecule, chemical compound, radiation agent, cytotoxic cells, biologics or combinations thereof.

In some embodiments, the cytotoxic cells are any one or more of T cells, NK cells, PBMCs or combinations thereof. In some embodiments, the cytotoxic cells are modified to express a chimeric or synthetic receptor or a T cell receptor.

In some embodiments, the antibodies are any one or more of chimeric antibodies, human antibodies, humanized antibodies, bispecific antibodies, bispecific T cell engager, DART, antibody drug conjugates or combination thereof.

In some embodiments, the reporter is expressed in cells by any one or more of plasmid vector, adenoviral vector, adenoassociated viral vector, sleeping beauty transposon, piggyback transposon, pCMV (cytomegalovirus) vectors, vaccinia virus vectors, retroviral vectors, lentiviral vectors, SV40 virus vectors, transfection of naked DNA or transfection of in vitro transcribed RNA. In some embodiments, the reporter is expressed using a non-vector method. In some embodiments, the reporter is expressed from a foreign promoter. In some embodiments, the reporter is expressed from a natural promoter.

In some embodiments, the target cells are exposed to the test agent in vitro. In some embodiments, the target cells are exposed to the test agent in vivo.

In some embodiments, the assay is performed in vitro. In some embodiments, the assay is performed in a high throughput fashion. In some embodiments, the assay is performed in vivo. In some embodiments, the target cells are present in a transgenic animal. In some embodiments, the assay is performed to identify agents that increase, decrease or have no effect on the cytotoxicity of an agent on a target cell. In some embodiments, the assay is performed with one or more agents used alone or in combination.

In some embodiments, the non-secretory form of the reporter is expressed using vectors encoding the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, *Renilla* Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or derivatives thereof.

In some embodiments, the target cell is a cell line expressing the non-secretory forms of GLuc, NLuc, MLuc7, HTLuc, PaLuc 1, PaLuc2, MpLuc1, McLuc1, MaLuc1, MoLuc1, MoLuc2, MLuc39, PsLuc1, LoLuc1-3, HtLuc2, TurboLuc16 (TLuc), *Renilla* Luc, Firefly luciferase (FfLuc or Fluc), LucPPe-146-1H2, LucPPe-133-1B2, LucPPe-78-0B10, LucPPe49-7C6A, LucPpL-81-6G1, CBGRluc, thermostable alkaline phosphatase or homologs or orthologs or mutants or derivatives or variant thereof.

In some embodiments, the target cell is a primary cell expressing the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), *Renilla* Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or derivatives thereof.

In some embodiments, the target cell has been modified and/or selected to lack the expression of one or more antigens. In some embodiments, the target cell has been modified and/or selected to express one or more antigens. In an embodiment, the target cell lines is engineered or modified to express one or more of the SARS-cov2 antigens, epitopes, polyepitopes or fragments thereof. The nucleic acid and amino acid SEQ ID NO of exemplary SARS-cov2 antigens, epitopes, polyepitopes or fragments are provided in Table 7B. In an embodiment, the target cell line is engineered or modified to express one or more of the SARS-cov2 receptors or fragments thereof. Exemplary SARS-cov2 receptor includes ACE2 (SEQ ID NO:235 and 705). In an embodiment, the target cell lines is engineered or modified to express one or more genes that enhance the entry and/or replication of SARS-cov2 (e.g. TMPRSS2; SEQ ID NO: 236 and 706).

Further provided herein are kits comprising components for assessing cytotoxicity of an agent targeting SARS-cov2. In various embodiments, the kits include target cells (for example, cells engineered to express intracellularly one or more reporters and/or cell lines expressing one or more reporters and/or primary cells expressing one or more reporters), and substrates for activating the reporter. The target cells, reporters and substrates are as described herein. In various embodiments, the kits further comprise instructions for use of the kit.

Engineered Cell Lines Stably Expressing Thermostable Luciferase for Measuring Viral Infectivity and Cytopathic Effect.

The disclosure provides cells and cell lines for testing the infection by viruses (e.g., SARS-cov2) using Matador assays. The method includes expression of a reporter in target cells in a manner so that it is preferentially retained within the healthy cells but is either released from virally infected dead and dying cells or whose activity can be preferentially measured in dead and dying cells. In one embodiment, the inventive method measures the activity of the reporter that has been released from the dead and dying cells. In some embodiments, the reporters are any one or more of: 1) non-secreted forms of luciferases from the copepods, such as *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri, Pleuromamma scutullata* or their homologs; 2) engineered luciferase reporters from deep sea shrimp, such as NanoLuc; 3) *Renilla* luciferase; 4) beetle luciferases, including firefly luciferases and engineered variants such as LucPPe-146-1H2. Other reporters, such as Green Fluorescent Protein, mCherry, and heat-stable alkaline phosphatase may also be used with the assays described herein. Vectors for expressing the reporter genes in stable and transient fashion, engineered cell lines stably expressing the reporter genes, and kits for practicing the invention are also disclosed. In some embodiments, the methods described herein measure the activity of the reporter inside dead and dying cells by addition of a substrate or a cofactor that is required for the activity of the reporter and which is excluded from the healthy cells but preferentially enters dead and dying cells. The method can be used to measure the titer of a virus.

Provided herein are methods for assessing infectivity and cytopathogenicity of a virus. The methods include providing a target cell that is permissive for virus infection and has been engineered to express intracellularly a reporter; exposing the target cell to an agent capable of modulating cytotoxicity; and assaying the activity of the reporter. In one embodiment, a change in reporter activity relative to a reference value is indicative of the presence of the virus. In one embodiment, a change in reporter activity is an increase in reporter activity relative to a reference value. In some embodiments, the reporter is expressed endogenously by the target cell at a level that is at least 10-25%, 25-50%, 50-75% or 75-100% lower than what is achieved by engineered expression.

In on embodiment, the reporter activity is assayed in the cell media containing the target cells. In another embodiment, the reporter activity is assayed in the cell supernatant that is free of the target cells.

In various embodiments, the infectivity of a virus or a preparation containing a virus is measured by obtaining (assaying) the reporter activity in cell pellet and cell free supernatant and normalizing the reporter activity measured in the cell free supernatant. In various embodiments, normalizing comprises dividing the activity in the cell free supernatant by the reporter activity measured in the cell pellet.

In various embodiments, the reporter is a non-secretory form of an enzyme that is stable under the assay conditions at 37° C. for more than 15 min, for more than 30 min, for more than 1 hour, for more than 2 hours, for more than 3 hours, for more than 4 hours, for more than 12 hours, 24 hours, for more than 36 hours, for more than 48 hours or for at least 96 hours.

In various embodiments, the reporter is a non-secretory form of a luciferase. In some embodiments, the non-secretory form of luciferase is obtained from copepods, deep sea shrimp, beetle, firefly, or homologs or orthologs thereof or mutants or variants or derivatives thereof. In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri,* and *Pleuromamma scutullata.*

In various embodiments, the luciferase is any one or more of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, *Renilla* Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or variants or derivatives thereof.

In various embodiments, the reporter is a non-secretory form of a luciferase obtained from copepods, deep sea shrimp, beetle, firefly or homologs or orthologs thereof or mutant or derivatives thereof and the reporter activity is assayed by exposing the target cells to a luciferase specific substrate. In various embodiments, the luciferase-specific substrate is coelentrazine or an imidazopyrazinone substrate (furimazine) or a derivative thereof. In one embodiment, the luciferase-specific substrate is D-luciferin or a derivative thereof.

In one embodiment, the reporter is a thermostable luciferase. In one embodiment, the reporter is a thermostable beetle luciferase. In an embodiment, the thermostable beetle luciferase is obtained from *Photuris pennsylvanica* and *Pyrophorus plagiothalamus.*

In some embodiments, the reference value is the reporter activity in any one or more of (i) target cells that do not express reporter, (ii) target cells that express reporter but are not infected with a virus (s); (iii) the target cells that are left untreated; (iv) target cells that are not treated with the substrate for the reporter, or (iii) a combination thereof.

In some embodiments, the target cells are exposed to the test agent in vitro. In some embodiments, the target cells are exposed to the test agent in vivo. In some embodiments, the assay is performed in vitro. In some embodiments, the assay is performed in a high throughput fashion. In some embodiments, the assay is performed in vivo.

In an embodiment, the cell line is any cell line that is capable of supporting the candidate viral infection. In an exemplary embodiment, the virus is a coronavirus (e.g., SARS-cov2) and the cell line is one or more of the following, but not limited to, VERO, VERO-E6, HEK-293, BGM, COS, CV-1, FRhK, LLC-MK2, MA-104, MEK, pCMK, HepG2, Huh-7 or RK-13. In some embodiments, the target cell is a primary cell (e.g., airway epithelial cells). In an exemplary embodiment, the cells are primary airway epithelial cells.

In some embodiments, the target cell has been modified and/or selected to lack or enhance the expression of one or more antigens. The nucleic acid and amino acid SEQ ID NO of exemplary SARS-cov2 antigens, epitopes, polyepitopes or fragments are provided in Table 7B. In an embodiment, the target cell line is engineered or modified to express one or more of the SARS-cov2 receptors or fragments thereof. Exemplary SARS-cov2 receptor includes ACE2 (SEQ ID NO:235 and 705). In an embodiment, the target cell lines is engineered or modified to express one or more genes that enhance the entry and/or replication of SARS-cov2 (e.g. TMPRSS2; SEQ ID NO: 236 and 706).

Further provided herein are kits comprising components for assessing viral (e.g., SARS-cov2) infectivity and cytopathic effects. In various embodiments, the kits include target cells (for example, cells engineered to express intracellularly one or more reporters and/or cell lines expressing one or more reporters and/or primary cells expressing one or more reporters), and substrates for activating the reporter.

Topanga Reagent Based on SARS-Cov2 Spike Glycoprotein and Nucleocapsid Proteins

In various embodiments, the instant invention provides a fast, economical, sensitive and specific Topanga assay and Topanga reagents for detection of antibodies, antibody fragments, non-immunoglobulin antigen binding modules (e.g. Centyrins, affibody, DARPINS etc.) and SABR targeting the proteins (e.g. spike glycoprotein and nucleocapsid) encoded by SARS-cov2 that does not require any expensive equipment. Due to their extreme sensitivity and broad dynamic range, the assay and reagents can be used as a quality-control tool during the manufacturing of SARS-cov2-specific SABR-expressing cells and to monitor their persistence in the body after infusion. The Topanga assay and Topanga reagents based on the spike glycoprotein and nucleocapsid of SARS-cov2 can be also used to detect antibodies, antibody fragments and non-immunoglobulin antigen binding modules (e.g. Centyrins, affibody, DARPINS etc.) targeting these proteins.

Provided herein is a method for detecting expression of an antibody, antibody fragment, non-immunoglobulin antibody binding module or SABR targeting Spike glycoprotein of SARS-cov2, comprising: obtaining a sample in need determination of expression of the antibody, antibody fragment, non-immunoglobulin antibody binding module or SABR; optionally immobilizing the antibody, antibody, antibody fragment, non-immunoglobulin antibody binding module to a solid surface (e.g., protein G or anti-IgG or anti-IgM coated plate or beads), contacting the sample with a fusion protein comprising a reporter fused to the spike glycoprotein of SARS-cov2 or a fragment or variant thereof; washing the samples to remove any un-bound reporter-Spike glycoprotein fusion protein, and assaying the activity of the reporter; wherein presence of reporter activity or increase in reporter activity relative to a reference value is indicative of the expression of the antibody, antibody, antibody fragment, non-immunoglobulin antibody binding module, or SABR in the sample. In an embodiment, the Spike glycoprotein is represented by SEQ ID NO:701 or a variant thereof having at least 70% homology to the amino acid sequence of SEQ ID NO:701. In an embodiment, the fragment of the Spike glycoprotein comprises its receptor binding domain (SEQ ID NO: 700) or a variant thereof having at least 70% homology to the amino acid sequence of SEQ ID NO: 700. The antibody, antibody fragment or the non-immunoglobulin antibody binding module that bind to the S1-RBD (SEQ ID NO: 700) is likely to have neutralizing activity against SARS-cov2. In an embodiment, the fragment of spike glycoprotein comprises its N-terminal domains represented by SEQ ID NO: 707 and 712 or variant thereof having at least 70% homology to the amino acid sequence of SEQ ID NO: 707 and 712. In an embodiment, the fragment of spike glycoprotein comprises its C-terminal domain (S2 protein) represented by SEQ ID NO: 694 or a variant thereof having at least 70% homology to the amino acid sequence of SEQ ID NO: 694.

Also provided herein is a method for detecting expression of an antibody, antibody fragment, non-immunoglobulin antibody binding module or SABR targeting nucleocapsid protein (SEQ ID NO: 702) of SARS-cov2, comprising: obtaining a sample in need determination of expression of the antibody, antibody fragment, non-immunoglobulin antibody binding module or SABR; optionally immobilizing the antibody, antibody, antibody fragment, non-immunoglobulin antibody binding module to a solid surface (e.g., protein G or anti-IgG or anti-IgM coated plate or beads), contacting the sample with a fusion protein comprising a reporter fused to the nucleocapsid protein of SARSC-cov2 or a fragment or variant thereof; washing the samples to remove any un-bound reporter-nucleocapsid fusion protein, and assaying the activity of the reporter; wherein presence of reporter activity or increase in reporter activity relative to a reference value is indicative of the expression of the antibody, antibody, antibody fragment, non-immunoglobulin antibody binding module, or SABR in the sample. In an embodiment, the nucleocapsid protein is represented by SEQ ID NO:702 or variant or fragment thereof having at least 70% homology to the amino acid sequence of SEQ ID NO:702.

Also provided herein is a method for detecting expression of an antibody, antibody fragment, non-immunoglobulin antibody binding module or SABR targeting SARS-cov2 orf3a (SEQ ID NO: 720), comprising: obtaining a sample in need determination of expression of the antibody, antibody fragment, non-immunoglobulin antibody binding module or SABR; optionally immobilizing the antibody, antibody, antibody fragment, non-immunoglobulin antibody binding module to a solid surface (e.g., protein G or anti-IgG or anti-IgM coated plate or beads), contacting the sample with a fusion protein comprising a reporter fused to the orf3a of SARSC-cov2 or a fragment or variant thereof; washing the samples to remove any un-bound reporter-nucleocapsid fusion protein, and assaying the activity of the reporter; wherein presence of reporter activity or increase in reporter activity relative to a reference value is indicative of the expression of the antibody, antibody, antibody fragment, non-immunoglobulin antibody binding module, or SABR in the sample. In an embodiment, the orf3a is represented by SEQ ID NO:720 or variant or fragment thereof having 70% homology to the amino acid sequence of SEQ ID NO:720.

In an embodiment, the sample is a blood sample. In an embodiment, the sample is a serum sample. In an embodiment, the sample is a plasma sample.

In an embodiment, the sample is a fresh sample. In another embodiment, the sample is frozen prior to measurement of the antibody, antibody fragment or non-immunoglobulin antigen binding module.

In one embodiment, the reporter is a non-secretory form of a luciferase. In exemplary embodiments, the non-secretory form of luciferase is obtained from copepods, deep sea shrimp or homologs or orthologs thereof or mutants or derivatives thereof.

In some embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata.*

In some embodiments, the luciferase is any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 *Renilla*, TurboLuc16 (TLuc) or homologs or orthologs thereof or mutants or functional derivatives thereof.

In exemplary embodiments, the spike glycoprotein-reporter fusion proteins are represented by SEQ ID NO: 716-718, 1197-1199, 1215-1217, 1225-1227, 1232-1234, 1242-1244. These fusion protein constructs also carry a C-terminal puromycin resistance module that is separated from the spike-glycoprotein-reporter fusion module by a T2A cleavable linker. The puromycin resistance module is optional and is not needed for the activity of the reporter fusion protein.

In exemplary embodiments, the nucleocapsid-reporter fusion proteins are represented by SEQ ID NO: 719, 1211, 1228, 1245 and 1262. These fusion protein constructs also carry a C-terminal puromycin resistance module that is separated from the reporter fusion module by a T2A cleavable linker. The puromycin resistance module is optional and is not needed for the activity of the reporter fusion protein.

In exemplary embodiments, the orf3a-reporter fusion proteins are represented by SEQ ID NO: 1212, 1229, 1246, and 1263. The constructs also carry a puromycin resistance module that is optional and is not needed for the activity of the reporter fusion protein.

In some embodiments, the reporter activity is assayed by addition of a luciferase specific substrate. In one embodiment, the luciferase-specific substrate is coelentrazine or a derivative thereof. In another embodiment, the luciferase-specific substrate is imidazopyrazinone substrate (furimazine) or a derivative thereof.

In an embodiment, the sample is taken from a subject who is at risk of acquiring SARS-cov2 infection. In an embodiment, the sample is taken from a subject who is suspected of having SARS-cov2 infection. In an embodiment, the sample is taken from a subject to determine if the subject has history of having infected with SARS-cov2. In an embodiment, the sample is taken from a subject to determine if the subject is immune to SARS-cov2 infection.

In an embodiment, antibody against SARS-cov2 is IgM. In an embodiment, antibody against SARS-cov2 is IgG.

In some embodiments, the SABR is expressed on an immune cell. In one embodiment, the immune cell is a T cell. In another embodiment, the immune cell is a CD4 T cell. In a further embodiment, the immune cell is a CD8 T cell. In an embodiment, the immune cell is a Treg cell. In some embodiments, the immune cell is a naive T cell. In some embodiments, the immune cell is a memory T cell. In some embodiments, the immune cell is central memory T cell. In an embodiment, the immune cell is an effector memory T cell. In an embodiment, immune cell is an NK cell or an NK cell line (e.g., NK92 cell line or NK92MI cell line).

In some embodiments, the SABR is expressed on a stem cell. In an embodiment, the SABR is expressed on a hematopoietic stem cell. In an embodiment, the CAR is expressed on an induced pluripotent stem cell.

In some embodiments, the fusion protein further comprises a tag. In exemplary embodiments, the tag is any one or more of chitin binding protein (CBP), glutathione-S-transferase (GST), polyhistidine (His) tag, FLAG tag, HA tag, Myc tag, V5 tag, AcV5 tag, Streptag or a combination thereof.

In some embodiments, the reference value is the reporter activity in any one or more of (i) sample from a subject who has never been exposed to SARS-cov2; (ii) sample from the test subject where the sample is treated with an unrelated fusion protein; (iii) samples that are not treated with the substrate for the reporter; or (iv) combinations thereof.

In some embodiments, the reference value is the reporter activity in any one or more of (i) cells that do not express the SABR; (ii) cells that express the SABR but are treated with fusion protein which is not bound by the SABR; (iii) cells that are not treated with the substrate for the reporter; or (iv) combinations thereof.

In some embodiments, the reporter is fused to SARS-cov2 protein (e.g. S1, S2, S1-RBD, nucleocapsid, orf3a) through a covalent bond.

In some embodiments, the reporter is fused to the SARS-cov2 protein (e.g. S1, S2, S1-RBD, nucleocapsid, orf3a) through a non-covalent bond.

In some embodiments, the reporter is fused to the SARS-cov2 protein (e.g. S1, S2, S1-RBD, nucleocapsid, orf3a) through an intermediate molecule.

In some embodiments, a single molecule of the reporter is fused to the SARS-cov2 protein (e.g. S1, S2, S1-RBD, nucleocapsid, orf3a)

In some embodiments, more than one molecule of the reporter is fused to the SARS-cov2 protein (e.g. S1, S2, S1-RBD, nucleocapsid, orf3a).

In one embodiment, the assay is performed in vitro. In another embodiment, the assay is performed in vivo.

In various embodiments, luciferase activity described herein is measured by any one or more of methods for measuring light production such as a luminometer, X-ray films, microscopy, or combinations thereof. The nucleic acid and amino acid sequences of the fusion proteins described in the above section are presented in the corresponding sequence sections.

The host cell line utilized for expression of the Luc fusion proteins of the present invention can be of mammalian or non-mammalian origin. Those skilled in the art are credited with ability to preferentially determine particular host cell lines which are best suited for the desired gene product to be expressed therein. In one embodiment, the host cell line utilized for generation of the Luc fusion proteins of the invention is mammalian in origin. Exemplary host cell lines include, but are not limited to, DG44 and DUXBll (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3×63-Ag3.653 (mouse myeloma), BFA-lclBPT (bovine endothelial cells), RAJI (human lymphocyte), 293FT and 293 (human kidney). Host cell lines are typically available from commercial services, the American Tissue Culture Collection or from published literature. In another embodiment, the host cell line utilized for generation of the Luc fusion proteins of the invention is of insect origin. In another embodiment, the host cells utilized for generation of the Luc fusion proteins of the invention are bacterial in origin. In another embodiment, the host cells utilized for generation of the Luc fusion proteins of the invention are of yeast origin. Those skilled in the art are credited with ability to preferentially determine particular promoters and vectors which are best suited for the expression of a desired gene product in a particular host cell line. Exemplary vector for expression of the Luc fusion protein of the invention is pLenti-EF1a (SEQ ID NO: 1) or pcDNA3 (SEQ ID NO: 17). Vectors for expression of proteins in other host cell lines are typically available from commercial sources, such as Thermofisher, Novagen and Sigma. In various embodiments, the fusion proteins described herein may be expressed in bacterial cells, yeasts or insects. The optimum vectors and promoters to be used for expression of the fusions proteins described herein and for the methods described herein will be apparent to a person of skill in the art.

In an embodiment, the fusion proteins are expressed in mammalian cells. In an embodiment, the fusion proteins are expressed in insect cells. In an embodiment, the fusion proteins are expressed in yeast cells. In an embodiment, the fusion proteins are expressed in bacterial cells. In an embodiment, the fusion proteins are expressed in vitro.

In an embodiment, the assay is conducted with the purified fusion protein. In an embodiment, the assay is conducted with unpurified fusion protein.

In an embodiment, the assay is performed as described in PCT/US2017/025602, which is incorporated herein in its entirety.

In an embodiment, the assay is conducted in tubes. In an embodiment, the assay is conducted in microwell plates. In an embodiment, the assay is conducted using Protein G, Protein A or Protein A/G coated plates or microbeads. In an embodiment, the assay is conducted using anti-IgG and anti-IgM coated plates or microbeads.

In an embodiment, the assay is carried out in 24 well plates, 48 well plates, 96 well plates or 384 well plates.

In an embodiment, the assay is used to measure the presence of antibodies to SARS-cov2 in a sample from a human subject. In an embodiment, the assay is used to measure the presence of antibodies to SARS-cov2 in a sample from an animal subject.

Malibu-Glo Reagents Against SARS-Co2

There are several methods currently in use for detection of SARS-cov2 antigens, including Flow cytometry, ELISA and western blotting. However, these methods require expensive equipment (such as flow cytometry), suffer from poor sensitivity and specificity (e.g., ELISA and Western blotting) or are time consuming. In various embodiments, the instant invention provides a fast, economical, sensitive and specific assay for detection of SARS-cov2 infected cells using a non-radioactive antigen detection assay described in PCT/US2017/025602, which is incorporated herein in its entirety.

Provided herein is a method for detecting the presence of SARS-cov2 spike glycoprotein in a sample, comprising: obtaining a sample infected with SARS-cov2; optionally immobilizing SARS-cov2 a to a solid surface, contacting the sample with a fusion protein comprising a reporter fused to moiety (e.g., scFv or vHH fragment etc.) capable of binding the spike glycoprotein of SARS-cov2; and assaying the activity of the reporter; wherein presence of reporter activity or increase in reporter activity relative to a reference value is indicative of the expression of the spike glycoprotein in the sample. The nucleic acid and amino acid SEQ ID of exemplary vL, vH and scFv fragments targeting the S1-RBD of SARS-cov2 are provided in Table 7A. The SEQ ID NO of the CDRs of the vL, vH fragments comprising the scFv are also provided in Table 7A.

Also provided herein is a method for detecting presence of SARS-cov2 in a sample, comprising: obtaining a sample in need determination of presence of SARS-cov2; optionally immobilizing SARS-cov2 to a solid surface, contacting the sample with a fusion protein comprising a reporter fused to the ACE2 extracellular domain (ECD) or a fragment or variant thereof; washing the samples to remove any unbound reporter-nucleocapsid fusion protein, and assaying the activity of the reporter; wherein presence of reporter activity or increase in reporter activity relative to a reference value is indicative of the presence of SARS-cov2 in the sample. In an embodiment, the ACE2-ECD is represented by SEQ ID NO:705 or variant or fragment thereof.

In one embodiment, the reporter is a non-secretory form of a luciferase. In exemplary embodiments, the non-secretory form of luciferase is obtained from copepods, deep sea shrimp or homologs or orthologs thereof or mutants or derivatives thereof.

In some embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri,* and *Pleuromamma scutullata.*

In some embodiments, the luciferase is any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 *Renilla*, TurboLuc16 (TLuc) or homologs or orthologs thereof or mutants or functional derivatives thereof.

In an embodiment, the scFv reporter fusion protein targeting the spike glycoprotein of SARS-cov2 are represented by SEQ ID NO:1202-1204, 1218-1221, 1236-1238, 1253-1255 or variants or fragments thereof. These fusion protein constructs also carry a C-terminal puromycin resistance module that is separated from the reporter fusion module by a T2A cleavable linker. The puromycin resistance module is optional and is not needed for the activity of the reporter fusion protein.

In an embodiment, the ACE2-ECD reporter fusion protein is represented by SEQ ID NO:1213, 1230, 1247, 1264 or variants or fragments thereof. These fusion protein constructs also carry a C-terminal puromycin resistance module that is separated from the reporter fusion module by a T2A cleavable linker. The puromycin resistance module is optional and is not needed for the activity of the reporter fusion protein.

In some embodiments, the reporter activity is assayed by exposing the sample to a luciferase specific substrate. In one embodiment, the luciferase-specific substrate is coelentrazine or a derivative thereof. In another embodiment, the luciferase-specific substrate is imidazopyrazinone substrate (furimazine) or a derivative thereof.

In some embodiments, the fusion protein further comprises a tag. In exemplary embodiments, the tag is any one or more of chitin binding protein (CBP), glutathione-S-transferase (GST), polyhistidine (His) tag, FLAG tag, HA tag, Myc tag, V5 tag, AcV5 tag, Streptag or a combination thereof.

In some embodiments, the reference value is the reporter activity in any one or more of (i) sample (e.g., cells or serum) that does not express the SARS-cov2 spike glycoprotein; (ii) sample (e.g., cells or serum) that express the SARS-cov2 spike glycoprotein but are treated with fusion protein which does not bind to SARS-cov2 spike glycoprotein; (iii) cells that are not treated with the substrate for the reporter; or (iv) combinations thereof.

In some embodiments, the reporter is fused to the module (e.g., scFv or ACE2) targeting SARS-cov2 spike glycoprotein through a covalent bond.

In some embodiments, the reporter is fused to the module (e.g., scFv or ACE2) targeting SARS-cov2 spike glycoprotein through a non-covalent bond.

In some embodiments, the reporter is fused to the module (e.g., scFv or ACE2) targeting SARS-cov2 spike glycoprotein through an intermediate molecule.

In some embodiments, a single molecule of the reporter is fused to the module (e.g., scFv or ACE2) targeting SARS-cov2 spike glycoprotein.

In some embodiments, more than one molecules of the reporter are fused to the module (e.g., scFv or ACE2) targeting SARS-cov2 spike glycoprotein.

In an embodiment, the module (e.g., scFv or ACE2) targeting SARS-cov2 spike glycoprotein binds to its receptor binding domain.

In one embodiment, the assay is performed in vitro. In another embodiment, the assay is performed in vivo.

In an embodiment, the assay is performed as described in PCT/US2017/025602, which is incorporated herein in its entirety.

Also provided herein are kits for practicing the invention.

In another aspect, the invention relates to a kit comprising a pharmaceutical composition, cell or cell population, (such as T cells, NK cells, iPSC) comprising vectors encoding nucleic acids encoding SABR, wherein the antigen specific domain of the SABR targets spike glycoprotein of SARS-cov2.

EXAMPLES

The invention is further described in the non-limiting examples.

Generation of Lentiviral Vectors Encoding SABRs

The sequence of lentiviral vectors pLenti-EF1a or pLenti-EF1α and pLenti-EF1a-DWPRE is represented by SEQ ID NO: 1 and SEQ ID NO: 2. The sequence of pCCLc-MNDU3 Vector and its variants are provided in SEQ ID NO: 4-6. The generation of Chimeric antigen receptor (e.g., $2^{nd}$ generation CARs, SIRs, Ab-TCR and TFP etc.) the generation and use of GGS-NLuc fusion proteins, and the generation and use of luciferase (e.g., GLuc) reporter cell lines for measurement of cellular cytotoxicity using the Matador assays have been described (PCT/US2017/024843, PCT/US2017/025602, PCT/US2017/052344, PCT/US2017/064379 and PCT/US2018/53247), which are incorporated in their entirety by reference herein.

Example 1: Comparison of SABR Transduction of SARS-Cov2 CTLs Derived from PBMCs and Isolated T Cells PBMC are collected from a SARS-cov2 sero-positive donor who has been exposed to SARS-cov2 and recovered from infection as determined by seropositivity for SA cov2 spike glycoprotein or has received a SARS-cov2 vaccine. Optionally, the subject is administered between 1-3 booster doses of a SARS-cov2 vaccine between 1-31 days prior to collection of PBMCs. In another embodiment, PBMC are collected from a healthy donor who has not been exposed to SARS-cov2. PBMC are thawed and recovered into RPMI medium. Cells are split into two fractions; ⅓ of cells (Stimulators) are infected with the lentiviral vector pCCLc-MNDU3 (SEQ ID NO: 4) encoding Spike Glycoprotein, membrane glycoprotein, nucleocapsid phosphoprotein and orf3a of SARS-cov2 (nucleic acid SEQ ID NO:1047 and amino acid SEQ ID NO: 1167) by spin-infection. In alternate embodiments, stimulator cells are generated by infection with pCCLc-MNDU3 (SEQ ID NO: 4) encoding different proteins, peptides, polypeptides and polyepitopes of SARS-cov2 either alone, in various combinations or in fusion with Ub-G76A mutant. The nucleic acid sequences of exemplary SARS-cov2 proteins, peptides; polypeptides and polyepitopes are represented by SEQ ID NO:224-234 and 1047-1053 The corresponding amino acid sequences are represented by SEQ ID NO: 694-704 and 1167-1173, respectively. In an alternate embodiment, the stimulator cells are generated by infection with an adenoviral vector encoding Spike Glycoprotein, membrane glycoprotein, nucleocapsid phosphoprotein and orf3 a of SARS-cov2. In another alternate embodiment, the stimulator cells are generated by infection with a lentiviral or adenoviral vector encoding one or more of the SARS-cov2 proteins, peptides, polypeptides and polyepitopes in fusion with a drug inducible protein destabilization domain (DIPDD), such as FKBP12-F36V (SEQ ID NO: 1161), IKZF1-ZF2-145-167 (SEQ ID NO: 1162), IKZF1-ZF2-ZF3-145-197 (SEQ ID NO: 1163), IKZF1-ZF2-ZF3-145-243 (SEQ ID NO: 1164). The nucleic acid sequences of exemplary SARS-cov2 proteins, peptides, polypeptides and polyepitopes in fusion with the DIPDD are represented by SEQ ID NO:1054-1075. The corresponding amino acid sequences are represented by SEQ ID NO: 1174-1195.

Stimulators are then washed twice and resuspended in RPMI/AB serum culture medium and irradiated at 2500 cGy (2500 rads). The remaining ⅔ of cells (Responders) are either transferred to RPMI/AB serum medium and held at 37° C. until they are be mixed with the Stimulators or are used to isolate CD3$^+$ T cells that are then cultured with the Stimulator PBMC.

In an alternate embodiment, stimulator cells are expanded under conditions that favor the expansion of T cells. For this purpose, after infection stimulator cells are resuspended in fresh XVIVO media containing 10 ng/ml CD3 antibody, 10 ng/ml CD28 antibody and 100 IU recombinant human-IL2. The cells are expanded in GRex flasks for 7-14 days to allow the expansion of T cells. Subsequently, the stimulator cells are irradiated at 2500 cGy (2500 rads) and mixed with responder PBMC or CD3+ T cells.

PBMC Activation

On day 0, cultures are initiated in 6 well (10 cm$^2$) GRex culture plates at ratio of 9×10$^6$ irradiated Stimulator PBMC cells to 21×1.0$^7$ Responder PBMC cells and returned to 37° C., tissue culture incubation. Though optional, on days 9 and 10, cell cultures are depleted of CD56$^+$, NK (Natural Killer) cells, prior to transduction.

Activation of Isolated CD3$^+$T Cells

On day 0, T cells are isolated (i.e., enriched) from PBMC by means known in the art (e.g., live FACS or anti-CD3-coated magnetic beads). T cells are initiated in 6 well (10 cm$^2$) GRex culture plates containing media comprising 20 U/ml IL2, at a ratio of 1 T cell/4 Stimulator PBMC cells and returned to 37° C., tissue culture incubation. On days 9 and 10, cell cultures are transduced with the lentiviral vector to express SABRs (as above, NK cell depletion is optional prior to transduction). Sensitizing the starting material (e.g., following CD3$^+$ enrichment) to viral antigens, such as SARS-cov2, results in an increase in the percentage of central memory phenotype T cells in the resultant population.

SABR Transduction

On days 9 and 10 isolated T cell and PBMC cultures are transduced with recombinant lentivirus encoding anti-CD 19 SABR (and puromycin selection marker) using spin-infection as described previously. Briefly, lentivirus encoding anti-CD 19 SABR are thawed at room temperature and added to plates in the presence of polybrene. Plates are wrapped in paraffin film and centrifuged at 2000×g for 2 hours at 32° C. Viral supernatant is aspirated and 1 ml of prepared cell suspension from each stimulation group (0.5× 10$^6$ cells/mL resuspended in YH5 media) is added. Plates are centrifuged at 1000×g for 15 minutes at 32° C. and incubated at 37° C., 5% CO2 overnight.

Cells for each stimulation condition are then removed and pooled for counting. Cells are resuspended in fresh YH5 media at 0.5-1.0×10$^6$ cells/ml.

On day 11, each stimulation condition (i.e. of isolated T cells or of Responder PBMC) are returned to culture with irradiated Stimulator PBMC. Samples are taken at each of Days 15, 23 and 27 for Fluorescence-Activated Cell Sorting (FACS) (e.g., for CD3$^+$, scFV$^+$ cells). Drug selection (puromycin) is induced on day 19.

SARS-cov2-CTLs derived from isolated T cells demonstrate improved viability and proliferative capacity. CD3$^+$ enriched starting material has a greater yield over conventional expansion and transduction conditions, demonstrating significantly improved viability and proliferative capacity. The efficiency of downstream SABR vector transduction is dependent upon proliferative capacity. Thus, higher viability and proliferative capacity in the antigen-stimulated T cells results in improved downstream SABR transduction efficiency. When compared to transduction in a crude PBMC culture, SABR SARS-cov2 CTLs derived from an initial CD3$^+$ enrichment step demonstrate a significant enhancement of downstream SABR transduction efficiency post stimulation and also show greater cell viability in response to puromycin selection.

Example 3: Generation of Anti-CD 19-SABR CTL Following Stimulation with PBMC or K562 Cells Expressing One or More of SARS-Cov2 Structural Proteins (e.g., Spike Glycoprotein, Nucleocapsid Phosphoprotein or Membrane Glycoprotein)

Standard anti-CD3/CD28 bead-based stimulation is widely used in the field as a method to expand T cells in vitro prior to transduction with SABR vectors. The following experiment is undertaken to determine the impact of various SABR-T cell stimuli amenable to a high-yield manufacturing process on the memory T cell immune-phenotype for a final therapeutic product.

K562 cells are infected with pCCLc-MNDU3 (SEQ NO: 4) encoding different proteins, peptides, polypeptides and polyepitopes of SARS-cov2 either alone, in various combinations or in fusion with Ub-G76A mutant. The nucleic acid sequences of SARS-cov2 proteins, peptides, polypeptides and polyepitopes are represented by SEQ ID NO:224-234 and 1047-1053. The corresponding amino acid sequences are represented by SEQ ID NO: 694-704 and 1167-1173, respectively. In another alternate embodiment, the stimulator cells are generated by infection with a lentiviral or adenoviral vector encoding one or more of the SARS-cov2 proteins, peptides, polypeptides and polyepitopes in fusion with a drug inducible protein destabilization domain (DIPDD), such as FKBP12-F36V (SEQ ID NO: 1161), IKZF1-ZF2-145-167 (SEQ ID NO: 1162), IKZF1-ZF2-ZF3-145-197 (SEQ ID NO: 1163), IKZF1-ZF2-ZF3-145-243 (SEQ ID NO: 1164). The nucleic acid sequences of exemplary SARS-cov2 proteins, peptides, polypeptides and polyepitopes in fusion with the DIPDD are represented by SEQ ID NO:1054-1075. The corresponding amino acid sequences are represented by SEQ ID NO: 1174-1195. K562 cells are expanded under standard conditions. K562 cells infected with vectors encoding SARS-cov2 proteins, peptides, polypeptides and polyepitopes in fusion with FKBP12-F36V are cultured in the presence of dTAG13 to induce degradation of the fusion protein. K562 cells infected with vectors encoding SARS-cov2 proteins, peptides, polypeptides and polyepitopes in fusion with IKZF1-ZF2-145-167, IKZF1-ZF2-ZF3-145-197, IKZF1-ZF2-ZF3-145-243 are cultured in the presence of Pomalidomide (2-10 µM), lenalidomide (5-10 µM), CC220 (2-5 µM), or CC885 to induce degradation of the fusion proteins.

The K562 cells optionally can be engineered to express one or more costimulatory molecules, such as 41BBL, CD80, CD83, CD86 and/or vFLIP K13.

The resulting K562 cells are irradiated at 90 Gy (9000 rads) and serve as Stimulator cells as described in the preceding example.

Isolated CD3$^+$, SARS-cov2-antigen specific T cells are stimulated and expanded with no stimulation, stimulation with soluble anti-CD3/CD28, stimulation with anti-CD3/CD28 beads, stimulation with K562 cells expressing SEQ ID NO: 1167-1173; stimulation with K562 cells expressing SEQ ID NO: 1186-1190 in the presence of dTAG13; stimulation with K562 cells expressing SEQ ID NO: 1191-1195 in the presence of pomalidomide (2 µM); stimulation with PBMC expressing SEQ ID NO: 1167-1173; stimulation with PBMC expressing SEQ ID NO: 1186-1190 in the presence of dTAG13; stimulation with PBMC expressing SEQ ID NO: 1191-1195 in the presence of pomalidomide (2 µM).

Following 3 days of stimulation, each culture is transduced with a viral vector encoding a synthetic antigen binding receptor (SABR) and returned to incubation for 7 days in standard (YE media) culture to allow for expansion of the transduced T cells. Cells are then harvested and cell phenotypes analyzed by cell staining and fluorescence activated cell sorting.

CD3$^+$, SARS-cov2-antigen specific T cells are removed from liquid nitrogen storage, thawed, and suspended in YH media at a concentration of $2\times10^6$ cells/mL with 100 IU/mL IL-2. The suspension is plated in a 24-well plate with 2 mLs of the suspension per well and incubated overnight. Following this overnight recovery, cells are counted and divided into the nine different treatment groups as described above with $6\times10^6$ cells per group, at a concentration of $1\times10^6$ cells/mL.

Stimulation with anti-CD3/CD28 Dynabeads is done at a cell:bead ratio of 1:1. A sufficient volume of beads is removed and washed in DPBS prior to direct addition to the cell suspension. Accordingly, stimulation culture is plated at 2 mL YH5 media with 100 IU/mL IL-2 per well in a 24 well plate, as above, and incubated for 3 days.

Stimulation with soluble anti-CD3/CD28 is done by direct addition of CD3/CD28 ImmunoCult™ reagent at a concentration of 25 µl per mL and incubated for 3 days.

Stimulation with SARS-cov2 expressing PBMC is done at a ratio of 1 SARS-cov2 antigen-specific T cell to four PBMC. Briefly, CD3+, SARS-cov2-antigen specific T cells are removed from liquid nitrogen storage, thawed, suspended in YH media, and allowed to recover. In preparation for stimulation culture, SARS-cov2-expressing K562 cells are irradiated with a total dose of 90 Gy (9000 rads) of radiation. SARS-cov2-K562 and antigen-specific cells are combined in YH5 media with 100 IU/mL IL-2 in the same 24-well plate as above and incubated for 3 days.

Lentiviral vector encoding the SABR (comprising either a 4-1BB or CD28 signal transduction domain) are used to infect the T cells by spin-infection as described.

Cells from each stimulation group are pooled, counted, and resuspended at a concentration of $0.5-1.0\times10^6$ cells/mL of fresh YH5 media before returning to incubation at 37° C., 5% CO2 for 2 days. Pooling and resuspension is repeated every two days until the seventh day (harvest). Once harvested cells are labeled and a flow cytometry gating strategy is applied to identify CD3, CD4, CD8, CD62L and CD45RO on the SABR-expressing T cells. Briefly, cell signals of interest are first identified by size and granularity (i.e. forward scatter (FSC) vs. side scatter (SSC)). Living cells are then identified based on staining with a viability dye (e.g., Live/Dead™ BV510). Viable single cells are then gated based on pulse-area vs. pulse-height (FSC-A vs. FSC-H). Individual CD3$^+$ T cells and subsequent subpopulations (e.g. CD4$^+$, CD8$^+$, central memory T cells) can then be identified using fluorescently-labeled antibodies.

Flow cytometric evaluation indicates that transduced CD 19-SABR-T cells stimulated with SARS-cov2-K562 or PBMC showed higher percentages of central memory T cell subsets as evaluated by CD62L$^+$/CD45RO$^+$ cells compared to soluble CD3/CD28 or bead stimulation.

These data demonstrate that stimulation of SABR-T cell cultures with BLCLs expressing SABR-targeted antigens leads to a shift to predominant central memory phenotype when compared to results from CD3/CD28 stimulation through bead-bound or soluble antibodies. This study supports the potential for improved quality of SABR-T cell cultures that utilize antigen-positive APC stimulation (as represented by antigen-presenting K562 or PBMC) versus the quality expected when using standard anti-CD3/CD28 bead or other acellular modes of stimulation.

Example 4: Anti-CD19-SABR-SARS-Cov2-CTLs Exert Potent and Specific Cytotoxicity

Similarly as above, lentiviral vector encoding the SABR (comprising either a 4-1BB or CD28 signal transduction domain) is used for transduction of SARS-cov2-BLCL-stimulated, CD3$^+$, antigen-specific T cells.

Briefly, SABR-expressing, virus-specific T cells are prepared in the following manner.
  Day 0, PBMC samples are thawed, and CD3$^+$ cells are enriched (e.g., by live FACS or anti-CD3-coated magnetic beads). These CD3$^+$ T cells are then stimulated by culturing with SARS-cov2-antigen-presenting BLCLs, K5462 or T cells as described herein.
  11 days post-stimulation (on Day 11), the culture are depleted of NK cells (e.g., using anti-CD56 beads) and re-stimulated with fresh SARS-cov2-antigen-presenting BLCLs, K5462 or T cells at a responder/stimulator ratio of 1:4 for 7 days.
  On Day 18, the culture are stimulated, at a responder/stimulator ratio of 4:1 for 2 days.
  On Day 20 transduction is initiated on with a viral vector encoding a synthetic antigen binding receptor (SABR) and returned to incubation in standard (YET media) culture to allow for expansion of the transduced, virus-specific T cells. Optionally, an NK cell depletion step may be employed immediately prior to transduction.
  By Day 25, SABR-expression is assessed (e.g., by FACS analysis) and SABR-expressing, virus-specific T cells (effectors) are be added to target cultures for cytotoxicity assays.

Cytotoxicity, measured by Matador assay, is observed after 4 hours in co culture with SARS-cov2-SABR19-SABR T cells or control SARS-cov2 CTLs at the ratios of 5:1. SARS-cov2-CD19-SABR T cells demonstrate HLA-independent, CD19-specific cytotoxicity with low allo-cytotoxicity as observed by the specific killing of CD19$^+$ (NALM6 and Raji) cells and SARS-cov2$^+$/CD19$^+$ HLA-matched and mismatched. BLCLs. In contrast, K562 cells, and HLA-matched and mismatched PHA blasts, all of which lack SARS-cov2 and CD19 antigen, are not killed. Moreover, SARS-cov2-sensitized, anti-CD 19 SABR T cells are cytotoxic to all CD19$^+$ cell lines with less off-target cytotoxicity, i.e., less or non-existent cytotoxicity to cells lacking both CD19 and SARS-cov2 expression. When observed for three days following effector addition (i.e., SARS-cov2-CTL or SARS-cov2-CD19 SABR T cell addition) specific and potent HLA-independent cytolysis is observed in targeted cells. Cytolysis is induced in both HLA-matched (BLCL targets) and HLA-mismatched (BLCL and Raji targets) cells. However, SARS-cov2-CTL are shown to only induce significant cytolysis in matched BLCL target cells.

When compared to conventionally produced SABR T cells (i.e., without enrichment or antigen stimulation of starting T cultures), antigen-specific SABR T cells (e.g., anti-CD19-CD28-SABR-SARS-cov2-CTLs) exhibit comparable, if not better, cytotoxicity. However, anti-CD 19-CD28-SABR-SARS-cov2-CTLs appear to be less alloreactive. The proliferative capacity of SARS-cov2-specific CD 19-SABR T cells is observed by CellTrace™ Violet dilution assays upon co-culture with the indicated cell lines. Anti-CD19-CD28-SABR-SARS-cov2-CTLs retain the ability to kill B-lymphoblastoid cell lines (BLCL) but spared autologous and allogeneic PHA-blast targets lacking CD 19 and SARS-cov2 antigen expression with notably less alloreactivity relative to conventional SABR T cells.

Example 5: Use of Allogeneic SABR-Expressing SARS-Cov2 Specific T Cells for Adoptive Cells Therapy Patients with relapsed Acute Lymphocytic Leukemia or high-risk intermediate grade B-cell lymphomas may receive immunotherapy with adoptively transferred HLA-matched allogeneic SABR-T cells. A leukapheresis product is collected from a SARS-cov2 seropositive allogeneic donor and used to isolate PBMC by Ficoll-Hypaque separation. A high-resolution HLA typing is done on the donor PBMC. Optionally, CD3 positive T lymphocytes are selected using the CliniMACS Prodigy® System from Miltenyi Biotec and following the manufacturer's recommendations. One third of the T cells are used to generate Stimulator cells, while the remainder are used as responder cells. Optionally, the expression of β2M and CD52 is eliminated in T cells by CRISPS mediated knock-out using techniques known in the art and T cells lacking cell surface expression of HLA and/or CD52 are selected. PBMC and/or T cells are transduced with a lentiviral vectors encoding SARS-cov2 encoded peptides, polypeptides, proteins and polyepitopes (SEQ ID NO: 1047-1053) to serve as Stimulator cells. Alternatively, JEKO-1 cells expressing the SARS-cov2 encoded peptides, polypeptides, proteins and polyepitopes (SEQ ID NO: 1047-1053) and co-expressing 41BBL, CD80, CD83, CD86 and vFLIP K13 serve as Stimulator cells. Responder T cells are expanded by co-cultured with Stimulator cells at ratio of 1:4 in XVIVO medium with 20 IU/ml of IL2 in a GRex culture flask for 2-7 days to generate SARS-cov2 specific CTLs. The SARS-cov2 specific CTLs are transduced with a clinical grade CD19-SABR virus (e.g., CD8SP-hu-mROO5-1-vL-[hTCRb-S57C]-F-P2A-SP-hu-mROO5-1-vH-[hTCRa-T48C](SEQ ID NO: 261). After viral transduction, SARS-cov2 specific CTLs expressing CD19 SABR are expanded for 9-12 days in the presence of irradiated Stimulator JEKO-1 cells or BLCLs in a GRex flask at a ratio of 1:4. After the resulting cell product has undergone quality control testing (including sterility and tumor specific cytotoxicity tests), they are cryopreserved in aliquotes. A patient with refractory B-All, is enrolled in a trial to receive the allogeneic SARS-cov2 specific CTLs expressing CD19 SABR. The patient is a full HLA match (12/12) with the donor. The patient receives lymphodepletive chemotherapy (30 mg/m$^2$/day fludarabine plus 500 mg/m$^2$/day cyclophosphamide×3 days). The patient may optionally receive a single dose of a CD52 antibody (e.g., alemtuzumab at 0.1 to 0.5 mg/kg) between 5-15 days prior to infusion of T cells. One day after completion of the lymphodepleting regimen, the patient receives allogeneic SARS-cov2 specific CTLs expressing CD19 SABR intravenously. The dose of SABR-T product may vary from 1×10$^4$ SABR+ve CD3 cells/kg to 5×10$^9$ SABR+ve CD3 cells/kg as per the study protocol. The SABR product may be administered in a single infusion or split infusions. Use of immunosuppressive drugs is at the discretion of the physician. Essentially a similar approach can be used to treat other diseases using allogeneic SARS-cov2 specific CTLs (e.g., T cells) expressing the SABR of the disclosure where the SABR targets an antigen or antigens expressed on the disease causing or disease-associated cells.

Example

SARS-CoV-2-specific T cells were generated from PBMCs isolated from a healthy donor fully vaccinated with SARS-CoV2 Pfizer vaccine. PBMCs were pulsed with PepTivator SARS-CoV2-Prot_S (Cat #130-126-700; Miltenyi Biotec), a pool of lyophilized peptides, consisting of 15-mer sequences with 11 amino acids (aa) overlap, covering the immunodominant sequence domains of the surface glycoprotein (S) of SARS-CoV2. The PepTivator SARS-CoV-2 Prot_S contains the sequence domains aa 304-338, 421-475, 492-519, 683-707, 741-770, 785-802, and 885-1273. This mix of overlapping peptide pool was used at a concentration of 1 µg/µL per $15 \times 10^6$ PBMCs for 30 minutes at 37° C. After incubation, cells were resuspended with 400 IU/mL interleukin-4 (R&D Systems) and 10 ng/mL IL-7 (Peprotech) in CTL media consisting of 45% RPMI, 45% Click medium (Irvine Scientific), and 10% fetal bovine serum (FBS) and plated in a 6-well GRex plate for expansion. Cytokines and peptide pulsed PBMC were replenished on day 7. On day 10, cells were harvested and evaluated for antigen specificity and functionality using a SARS-CoV-2 Prot_S T cell analysis kit (Cat #130-127-586; Miltenyi Biotec).

Expansion is continued as above for 2-3 weeks. After expansion, the SARS-CoV-2 specific T cells are isolated and used to generate SABR-T cells by infection with a lentiviral vector encoding a SABR against CD19. The SABR-T cells generated from SARS-CoV2 specific T cells are found to be less alloreactive in a mixed lymphocytic reaction and cause less Graft vs host disease when tested in immunodeficient mice as compared to the SABR-T cells generated from parental T cells that have not been enriched for SARS-CoV2 specificity.

Example 6: Development of Topanga, a Novel Luciferase-Based Assay for Detection of SARS-Cov2 SABR A challenge in the field of cellular immunotherapy is the lack of a robust assay for detection of SABR on the surface of immune cells. We recently described a fast, economical, sensitive and specific assay for detection of SABRs on the surface of immune cells (6). The method consists of fusing the antigen binding domain to a marine luciferase. The expression cassette also carries sequences encoding single or multiple copies of epitope tags, such as FLAG, HA and MYC, Streptag and polyhistidine tag. To demonstrate the feasibility of the assay, we expressed a second generation CAR (SEQ ID NO: 309) directed against the S-RBD of SARS-cov2 in JNG cells, which is a clone of Jurkat T cells that has been engineered to express GFP under an NFAT promoter. S-RBD-NLuc (SEQ ID NO: 717) and PSMA-NLuc (negative control) fusion proteins were generated by transient transfection of 293FT cells with the corresponding expression vectors. The expression cassette for S-RBD-NLuc (SEQ ID NO: 247) also contained a Puromycin resistance gene, which was separated from the S-RBD-NLuc cassette by a T2A cleavable linker. Supernatants containing the secreted fusion proteins were collected 24-72 h after transfection. JNG-parental (JNG-P) and JNG-S-RBD-BBz CAR cells were incubated with S-RBD-NLuc and PSMA-NLuc (negative control) fusion proteins, followed by extensive washes and measurement of the bound fusion protein by luciferase reporter assay. A nearly 20-fold increase in luciferase activity was observed upon binding of S-RBD-NLuc to JNG-S-RBD-BBz CAR cells as compared to the JNG-P cells, demonstrating the remarkable sensitivity and specificity of the assay. Essentially similar results were obtained when the NLuc was replaced by GLuc, TLuc or MLuc7 in the S1-RBD fusion-reporter protein. The nucleic acid sequences of S1-RBD in fusion with the GLuc, TLuc and MLuc7 are represented by SEQ ID NO: 1106, 1123 and 1141, respectively. The corresponding amino acid sequences are represented by SEQ ID NO:1226, 1243 and 1260, respectively.

To demonstrate the feasibility of Topanga assay, we performed a pilot experiment using SARS-CoV2-monoclonal antibody CR3022 that binds to SARS-CoV2 RBD. Serial dilutions of CR3022 (BEI resources) were added to individual wells of a Protein G coated 96 well plate in duplicate. After incubation, wells were washed and 100 µl of S1-RBD-NLuc supernatant was added to each well for 1 h. After washes, luminescence was read by addition of coelenterazine. An increase in luminescence above the PBS control was visible even at the lowest concentration of CR3022 tested (i.e., 0.1 pg/ml), thereby demonstrating the extreme sensitivity of the assay. There was a linear decrease in luminescence with increased dilution of CR3022 ($R2=1$).

Serum samples from COVID-19 (+) patients and a normal control were obtained. Serial dilutions of samples were tested using S1-RBD-NLuc supernatant and using Protein G coated 384 well plate. A difference between positive and negative samples was noted even at the lowest dilution (1:1000) tested. To demonstrate the specificity of the assay, 14 serum samples from COVID(−) subjects were examined and were found to be negative.

Topanga-reagent based on SARS-CoV2 RBD was purified using Streptacin Resin and demonstrated functional activity against sero-positive and sero-negative samples. Crude supernatant of Topanga Reagents offered equal sensitivity and specificity as the purified protein. Crude and purified Topanga reagents also demonstrated increase in immune response to SARS-CoV2 vaccine. A nearly 2 fold increase in titers were observed after the first dose of Pfizer vaccine and a nearly 10 fold increase in titer was observed after the $2^{nd}$ dose of Pfizer vaccine. Essentially similar results are obtained when experiment is repeated using vaccines from other manufacturer (e.g., Moderna, Johnson and Johnson, Astrazaneca, Sinovac etc.)

Next Topanga reagents were generated using S1-RBD derived from different variants of SARS-CoV2 containing mutations L452R, L477N, E484K, K417N, K417N-E484K-N501Y etc. The Topanga reagents based on variants were used to monitor immune response the subject vaccinated using the SARS-Cov2 vaccines from Pfizer. It was observed that the variant Topanga reagents can inform the residual immunity present against the variant in the post-vaccination sample and inform the decision to receive a booster dose depending on whether the level of antibodies have fallen below the pre-vaccination level or the level of antibodies in the control serum.

Example 7: Development of Malibu-Glo Antigen Detection Assay

The antigen binding portion of CARs is generally composed of scFv derived from antibodies. To rapidly screen the different scFv fragments and other antigen binding motifs (e.g., vHH, centyrins etc.) for optimal antigen binding affinity, we recently described another novel assay called the Malibu-Glo assay. In contrast to the Topanga reagent, the Malibu-Glo reagent involves fusion of an antigen binding motif (e.g., a scFv fragments) to a cassette encoding a marine luciferase (e.g., NLuc) and different epitope tags. To demonstrate the feasibility of the Malibu-Glo assay, we stably expressed the receptor binding domain of Spike glycoprotein (S-RBD) of SARS-cov2 in K562 cells in a membrane anchored manner by fusion to the hinge and transmembrane domains of murine CD8 and generated two mass populations, K562-S-RBD #1 and K562-S-RBD #2, respectively. The nucleic acid and amino acid sequences of the construct are represented by SEQ ID NO: 229 and 699, respectively. We also generated a lentiviral expression vector encoding the Malibu-Glo reagent CD8SP-SARScov2-CR3022-(vL-vH)-GGSG-NLuc-4×FLAG-×2STREP-8× His-T2A-PAC (SEQ ID NO:1082). In this vector the scFv targeting the S1-RBD is fused to a cassette encoding NLuc-4×FLAG-×2STREP-8×His via a GGSG linker. The cassette is linked via a T2A cleavable linker to a puromycin resistance gene (PAC). We expressed the fusion protein by transient transfection in 293FT cells and collected the secreted fusion protein (SEQ ID NO: 1219) in the supernatant approximately 72 h post-transfection. K562-parental (K562-P), K562-S-RBD #1 and K562-S-RBD #2 cells were incubated with the secreted fusion protein (SARScov2-CR3022-(vL-vH)-GGSG-NLuc). A PSMA-GGS-NLuc fusion protein was used as negative control. Following extensive washes, the cell bound scFv was measured by addition of coelentrazine and measurement of light production. A marked increase in luciferase activity was observed upon binding of SARScov2-CR3022-(vL-vH)-GGSG-NLuc (S-RBD-scFv-NLuc) fusion protein to K562-S-RBD #1and K562-S-RBD #2 cells as compared to the K562-P cells. In contrast, negligible binding of PSMA-GGS-NLuc fusion protein was observed to K562-P or K562-S-RBD #1 or #2 cells. These results demonstrate the remarkable sensitivity and specificity of the Malibu-Glo assay for selection of an optimal scFv for incorporation into a CAR. The results further demonstrate that the candidate scFv chosen by us can specifically recognize and bind with good affinity to the receptor binding domain of the spike glycoprotein (S-RBD) of SARS-cov2. Essentially similar results were obtained when the NLuc module was replaced by GLuc, TLuc and MLuc7. The nucleic acid sequences of SARScov2-CR3022-(vL-vH) in fusion with the GLuc, TLuc and MLuc7 are represented by SEQ ID NO: 1099, 1116 and 1133, respectively. The corresponding amino acid sequences are represented by SEQ ID NO:1219, 1236 and 1253, respectively. Finally, essentially similar results are obtained when the SARScov2-CR3022-(vL-vH) is replaced by SARS-cov2-S-RBD-H4-(vL-vH) and SARScov2-S-RBD-B38-(vL-vH).

Example 8: Generation and Activity of SABR Against SARS-Cov2 Spike Glycoprotein

Based on the results showing the specific binding and high affinity of the scFv SARScov2-CR3022-(vL-vH) against S-RBD, we next incorporated this scFv into a lentiviral vector to generate a second-generation S-RBD-specific CAR containing a 41BB costimulatory domain (S-RBD-BBZ-CAR) (SEQ ID NO: 309). We also generated a SABR on the SIR background incorporating the vL and vH fragment from this scFv. The nucleic acid and amino acid sequence of this SIR are represented by SEQ ID NO: 318 and 788, respectively. We expressed these SABR (CAR and SIR) constructs into JNG cells (Jurkat-NFAT-GFP) cells that express GFP under an NFAT promoter as described above. To test the ability of the SABR to induce T cell signaling in an antigen-specific manner, we co-cultured the JNG-P and JNG-S-RBD-BBz CAR and JNG-S-RBD-002-SIR cells with K562-parental (K562-P) and K562-S-RBD and RAJI-parental (RAJI-P) and RAJI-S-RBD cells. Induction of NFAT-signaling driven GFP expression was measured after overnight co-culture using flow-cytometry. Co-culture of JNG-S-RBD-BBz CAR and JNG-S-RBD-002-SIR cells with K562-S-RBD and RAJI-S-RBD cells led to increase in GFP induction as compared to incubation with K562-P and RAJI-P cells. These results demonstrate that S-RBD-specific CAR and SIR can specifically recognize and induce T cell signaling upon encountering target cells expressing cell surface expressed RBD of spike glycoprotein of SARS-cov2. In alternate embodiment, the experiment is repeated with other SABRs targeting SARS-cov2 spike glycoprotein RBD as listed in Table 9-11.

The SABR targeting SARS-cov2 S1-RBD are expressed in primary T cells using lentiviral mediated gene transfer. The T cells are expanded and co-cultured with K562-S-RBD and RAJI-S-RBD cells stably expressing GLuc for 24-48 hours. Effective lysis of the target cells is observed using the Matador assay. Further, increased secretion of IFNγ and TNFα is observed in the supernatant of SABR-T cells when cultured with K562-S-RBD and RAJI-S-RBD cells as compared to K562-P and RAJI-P cells. The experiment is also repeated with other SABRs targeting SARS-cov2 spike glycoprotein RBD as listed in Table 9-11.

The SABR targeting SARS-cov2 S1-RBD are also expressed in primary T cells obtained from an allogeneic donor using lentiviral mediated gene transfer. The TRAC and beta2 microglobulin (B2M) genes are deleted in the donor cells using CRISP/Cas9. The allogeneic T cells are expanded and co-cultured with K562-S-RBD and RAJI-S-RBD cells stably expressing GLuc for 24-48 hours. Effective lysis of the target cells is observed using the Matador assay. Further, increased secretion of IFNγ and TNFα is observed in the supernatant of SABR-T cells when cultured with K562-S-RBD and RAJI-S-RBD cells as compared to K562-P and RAJI-P cells. The allogeneic SABR-T cells targeting S-RBD of spike glyoprotein of SARS-cov2 are also administered to a patient with COVID-19. The experiment is also repeated with other SABRs targeting SARS-cov2 spike glycoprotein RBD as listed in Table 9-11.

The SABR targeting SARS-cov2 S1-RBD are also expressed in NK92MI cell line. The cells are expanded under cGMP conditions, tested for potency using the Matador assay and administered to a patient with COVID-19 in escalating doses.

The SABR targeting SARS-cov2 S1-RBD are expressed in human iPSC cells. The endogenous TRAC and B2M genes are deleted in the iPSC cells. The cells are expanded under cGMP conditions and differentiated into NK and T cells in vitro. The cells are tested for potency using the Matador assay and administered to a patient with COVID-19 in escalating doses.

Example 9: Use of Matador Assay to Test for Presence of SARS-Cov2 and Related Coronaviruses VeroE6 cells are engineered to stably express TMPRSS2 (SEQ ID NO: 236). VERO-E6 and VERO-E6-TMPRSS2 cells are further engineered to stably express Glue, NLuc, TLuc, MLuc7 or LucPPe-146-1H2 (SEQ ID NO: 21) in intracelluarly. The SEQ ID of the luciferases are provided in Table 2. To test the presence of SARS-cov2 in a sample, serial dilution of samples are added to VERO-E6 or VERO-E6-TMPRSS2 cells that have been plated the day before in a 96 well plate to result in 50% confluency. After varying period of time, supernatant is collected and used for the measurement of luciferase activity by addition of appropriate substrate (e.g., coelentrazine or D-luciferin). In an alternate embodiment, the luciferase activity is directly measured by adding the substrate to the 96 well plate as described previously. Cells treated with serial dilution of a known sample of SARS-cov2 serve as positive control, whereas cell treated with phosphate buffer saline serve as negative control. The increase in luciferase activity in sample treated with the virus as compared to control is reflective of the presence of the virus in the preparation. The titer of the virus is measured by comparison to the increase in luciferase activity with serially diluted samples of positive control.

The above assay is also modified to detect and measure the presence of an inhibitor of SARS-cov2 infectivity. For example, cells are treated with a known dose of SARS-cov2 in the presence of increasing concentration of a neutralizing antibody to SARS-cov2. The presence of neutralizing antibody and/or its activity is measured by measuring the luciferase activity in the cell supernatant or in cell population upon the addition of the appropriate substrate.

In an alternate embodiment, a dual reporter cell line is engineered that stably expresses intracellularly a marine luciferase (e.g., Gluc, TLuc, NLuc, MLuc7 etc.) and LucPPe-146-1H2 or its variants. After treatment with a preparation containing SARS-cov2, the LucPPe-146-1H2 and GLuc activities are sequentially measured from the sample using the Dual-Luciferase® Reporter (DLR™) Assay System (Promega) and following the manufacturer's recommendations.

Example 10: Development of Matador Assay to Measure the Cytotoxicity of Cellular and Immunotherapeutics Targeting SARS-Cov2 and Related Coronaviruses K562 and RAJI cells are engineered to stably express Glue, NLuc, MLuc7 or LucPPe-146-1H2 (SEQ ID NO: 21) intracelluarly. The cells are subsequently engineered to express one or more of SARS-cov2 encoded proteins, peptides, polypeptides and polyepitopes as described previously. In an exemplary embodiment, K562-S-RBD and RAJI-S1-RBD cells are engineered to express Glue intracellularly. To measure the cytotoxicity of a SABR-T cell targeting S-RBD of SARS-cov2, the K562-S-RBD-Glue cells are co-cultured with T cells encoding the SABR (S-RBD-BBZ-CAR) (SEQ ID NO: 309) at an effector to target (E:T) ratio of 1:1, 5:1 and 10:1 for 24 hours in a 384 well plate. The cytotoxicity of SABR-T cells is measured by addition of coelentrazine to the plates using an autoinjector as described previously.

In alternate embodiment, any suitable cell line expressing a heat stable luciferase and one or more of the SARS-cov2 encoded proteins, peptides, polypeptides and polyepitopes can be used in the Matador assay for measuring the cytotoxicity of an agent targeting SARS-cov2.

Example 11: Development of Topanga Assay for Detection of SARS-Cov2 Antibodies

Expression cassettes encoding Topanga reagents comprising different protein encoded by SARS-cov2 in fusion with marine luciferases are represented by SEQ ID NO:1197-1200, 1208-1212, 1215-1217, 1225-1229, 1232-1234, 1242-1246, 1249-1251 and 1259-1263. The fusion constructs are transfected in 293FT cells and fusion proteins purified from the cell supernatant (in case of secreted proteins) and cytosol (in case of non-secreted proteins) using StrepTactin column. 96-well Costar flat-bottomed luminometry plates are coated with protein G (5 µg/mL, 100 µL/well) in carbonate buffer (pH 9.6) overnight at 4° C. After three washes with phosphate buffered saline (PBS) containing 0.05% Tween 20 (PBS-T), the plates are incubated with blocking solution (PBS containing 5% non-fat milk) for 1 h at 37° C. Then the wells are washed, and aliquots of serially diluted sera (100 µL) are added to the wells and incubated for 1 h at 37° C. The plates are washed and incubated with 50 µl of diluted Nluc fusion proteins (10-100 ng) for 30 min at 37° C. Then the plates are washed again, and luciferase activity is measured after addition of coelentrazine. Each sample is tested in duplicate. The cut-off values are determined as two-fold the average of the normal controls. Negative controls are an equal volume mixture of sera from healthy blood donors. Results are expressed as the mean RLI (Relative Luminescence Intensity) from duplicate wells, and values are corrected by subtracting the RLI value of the background wells incubated with HEK 293 T cell extracts in the absence of sera. The sensitivity and specificity of the above assay is found to be superior to a commercially available ELISA assays (Euroimmun) for measuring SARS-cov2 antibodies. The presence of SARS-cov2 antibodies detected by the receptor binding domain of S1 protein is found to correlate with neutralizing antibodies to SARS-cov2.

In an alternate embodiment, the serum antibodies are captured using antibodies directed to human IgM or human: IgG subclasses instead of use of Protein G. Thus, for the detection of IgG antibodies against SARS-cov2, the plate is coated overnight with goal anti-Human IgG antibody. Similarly, for the detection of IgM antibodies against SARS-cov2, the plate is coated overnight with goal anti-Human IgM antibody. After three washes with phosphate buffered saline (PBS) containing 0.05% Tween 20 (PBS-T), the plates are incubated with blocking solution (PBS containing 5% non-fat milk) for 1 h at 37° C. Then the wells are washed, and aliquots of serially diluted sera (100 µL) are added to the wells and incubated for 1 h at 37° C. The plates are washed and incubated with 50 µl of diluted marine luciferase fusion proteins (10-100 ng) for 30 min at 37° C. Then the plates are washed again, and luciferase activity is measured after addition of coelentrazine. The sensitivity and specificity of the above assay is found to be superior to a commercially available ELISA assays for measuring SARS-cov2 antibodies. The presence of SARS-cov2 antibodies detected by the receptor binding domain of S1 protein is found to correlate with neutralizing antibodies to SARS-cov2.

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

Those skilled in the art will recognize, or be able to ascertain using no more than routine experimentation, many equivalents to the specific embodiments of the invention described herein. Such equivalents are intended to be encompassed by the following claims,

SEQUENCE LISTING

The patent contains a lengthy sequence listing. A copy of the sequence listing is available in electronic form from the USPTO web site (https://seqdata.uspto.gov/?pageRequest=docDetail&DocID=US12305186B2). An electronic copy of the sequence listing will also be available from the USPTO upon request and payment of the fee set forth in 37 CFR 1.19(b)(3).

What is claimed is:

1. A method of generating an adoptive cell therapy composition comprising:
    transducing T cells that express a T-cell receptor that specifically binds to a SARS-cov2 encoded first antigen with a nucleic acid encoding at least one synthetic antigen binding receptor (SABR) specific for binding to a second antigen selected from the group consisting of a cell surface marker, a cancer cell-associated antigen, a tumor antigen, an autoimmune-associated antigen, a differentiation antigen, an over-expressed embryonic antigen, a mutated tumor suppressor gene and a tumor antigen resulting from chromosomal translocation.

2. A method of generating an adoptive cell therapy composition comprising: transducing allogeneic or autologous T cells that express a T cell receptor that specifically binds to a SARS-cov2-encoded first antigen presented on a major histocompatibility complex (MHC) with a vector comprising a nucleic acid encoding a synthetic antigen binding receptor (SABR) that specifically binds to a second antigen, wherein the second antigen is a target-cell antigen or a cell surface marker.

3. The method of claim 1 or 2, wherein said second antigen is selected from the group consisting of CD5; CD19; CD123; CD22; CD30; CD171; CS 1; CD33; epidermal growth factor receptor variant III (EGFRviii); ganglioside G2 (GD2); ganglioside GD3 (aNeu5Ac (2-8) aNeu5Ac (2-3) bDGalp (1-4) bDG1cp (1-1) Cer); TNF receptor family member B cell maturation (BCMA); Tn antigen; prostate-specific membrane antigen (PSMA); Receptor tyrosine kinase-like orphan receptor 1 (ROR1); Fms Like Tyrosine Kinase 3 (FL T3); Tumor-associated glycoprotein 72 (TAG72); CD38; CD44v6; a glycosylated CD43 epitope expressed on acute leukemia or lymphoma but not on hematopoietic progenitors; a glycosylated CD43 epitope expressed on nonhematopoietic cancers; Carcinoembryonic antigen (CEA); Epithelial cell adhesion molecule (EP-CAM); B7H3 (CD276); KIT (CD117); Interleukin-13 receptor subunit alpha-2; Mesothelin; Interleukin 11 receptor alpha (IL-11Ra); prostate stem cell antigen (PSCA); Protease Serine 21; vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Folate receptor beta (FRb); Receptor tyrosine-protein kinase ERBB2; Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin 82; fibroblast activation protein alpha; insulin-like growth factor 1 receptor (IGF-1 receptor); carbonic anhydrase IX (CAIX); Proteasome Subunit, Beta Type, 9; glycoprotein 100 (gp100); oncogene fusion protein consisting of breakpoint cluster region (BCR) and Abelson murine leukemia viral oncogene homolog 1 (Abl) (bcrabl); tyrosinase; ephrin type-A receptor 2 (EphA2); sialyl Lewis adhesion molecule (sle); ganglioside GM3 (aNeuSAc (2-3) bDClalpd-4) bDGlcp (-1) Cer); transglutaminase 5 (TGS5); high molecular weight-melanoma associated antigen (HMWMAA); o-acetyl-GD2 ganglioside (OAcGD2); tumor endothelial marker 1 (TEM 1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen NY-BR-1 (NY-BR-1); uroplakin 2 (UPK2); adrenoceptor beta 3 (ADRB3); pannexin 3 (PANX3); G protein-coupled receptor 20 (GPR20); lymphocyte antigen 6 complex, locus K 9 (L Y6K); Olfactory receptor 51 E2 (OR51 E2); TCR Gamma Alternate Reading Frame Protein (TARP); Wilms tumor protein (WT1); Cancer/testis antigen 1; Cancer/testis antigen 2; Melanoma-associated antigen 1 (MAGE-A 1); ETS translocation-variant gene 6, located on chromosome 12p (ETV6-AML); sperm protein 17 (SPA17); X Antigen Family, Member IA; angiopoietin-binding cell surface receptor 2 (Tie 2); melanoma cancer testis antigen-1; melanoma cancer testis antigen-2; Fos-related antigen 1; tumor protein p53 (p53); p53 mutant; prostein; survivin; telomerase; prostate carcinoma tumor antigen-1; melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); transmembrane protease, serine 2 (TMPRSS2) ETS fusion gene; N-Acetyl glucosaminyl-transferase V; paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYPIB 1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32; lymphocyte-specific protein tyrosine kinase (LCK); A kinase anchor protein 4 (AKAP-4); synovial sarcoma, X breakpoint 2 (SSX2); Receptor for Advanced Glycation Endproducts; renal ubiquitous 1 (RU1); renal ubiquitous 2 (RU2); legumain; intestinal carboxyl esterase; heat shock protein 70-2 mutated; CD79a; CD79b; CD72; Leukocyte-associated immunoglobulin-like receptor 1 (LAI R 1; Fc fragment of IgA receptor; Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL 1), MPL; Biotin; c-MYC epitope Tag; CD34; LAMP1; TROP2; GFRalpha4; CDH17; CDH6; NYBR1; CDH19; CD200R; Slea; Fucosyl-GM1; PTK7; gpNMB; CDH1-CD324; DLL3; CD276/B7H3; IL 11 Ra; IL 13Ra2; CD179b-IGLII; TCR-gamma-delta; NKG2D; CD32; Tim1-/HVCR1; CSF2RA; TGFbetaR2; Lews Ag, TCR-beta1 chain; TCR-beta2 chain; TCR-gamma chain; TCR-delta chain; FITC; Luteinizing hormone receptor (LHR); Follicle stimulating hormone receptor (FSHR); Gonadotropin Hormone receptor; CCR4; GD3; SLAMF6; SLAMF4; HIV1 envelope glycoprotein; HTLV1-Tax; CMV pp65; EBVEBNA3c; KSHV K8.1; KSHV-gH; GAD; PDL 1; Guanylyl cyclase C (GCC); auto antibody to desmoglein 3 (Dsg3); auto antibody to desmoglein 1 (Dsg1); HLA, HLA-A; HLA-A2; HLA-B; HLA-C; HLA-DP; HLA-DM; HLA-DOA; HLA-008HLA-DOB; HLA-DQ; HLA-DR; HLA-G; IgE; CD99; Ras G12V; Tissue Factor 1 (TF1); AFP; GPRC5D; Claudin18.2; P-glycoprotein; STEAP1; Liv1; Nectin-4; Cripto; gpA33; BST1/CD157; low conductance chloride channel; the antigen recognized by TNT antibody; CD229; Toso; and BAFF-R.

4. The method of claim 1, wherein the nucleic acid encoding the SABR is introduced into T cells using a vector, wherein optionally the vector is a retroviral vector, a lentiviral vector, or an in vitro transcribed RNA vector.

5. The method of claim 1, wherein SARS-cov2 is the etiological agent of coronavirus disease 2019 (COVID-19) or a variant thereof.

6. The method of claim 1, wherein the SARS-cov2 peptide antigen is comprised of at least 5 but no more than 25 contiguous amino acids sequence of any SARS-cov2 viral protein or a variant thereof.

7. The method of claim 6, wherein the SARS-cov2 peptide antigen is selected from one or more of the following:
 a) a sequence of at least 5 but no more than 25 contiguous amino acids derived from one or more of SEQ ID NO: 694, 700-703, 707, or 712, or a variant with at least 80% sequence homology thereof; and/or
 b) a sequence with at least 80% homology to a peptide sequence selected from SEQ ID NO: 980-1028; and/or
 c) a sequence with up to 3 conservative substitutions in a peptide sequence selected from SEQ ID NO: 980-1028.

8. The method of claim 1, wherein the T cells are obtained from a SARS-cov2-immune or a SARS-cov2-positive subject.

9. The method of claim 8, wherein the SARS-cov2-immune or a SARS-cov2-positive subject has one or more of the following characteristics:
 (a) evidence of cellular and/or humoral immunity to SARS-cov2;
 (b) a history of infection with SARS-cov2;
 (c) history of having received a SARS-cov2 vaccine;
 (d) history of receiving one or more SARS-cov2 vaccine booster dose;
 (e) T cells that recognize one or more antigens encoded by SARS-cov2 wherein the level of the SARS-cov2 specific T cells is at least 20% higher than a subject who is not SARS-cov2 immune and/or is in the top 20, 30, 40, 50, 60, 70, 80 or 90 percentile of the SARS-cov2 immune subjects; and/or
 (f) antibodies against one or more antigens encoded by SARS-cov2; wherein the level of the SARS-cov2 antibodies is at least 20% higher than a subject who is not SARS-cov2 immune and/or is in the top 20, 30, 40, 50, 60, 70, 80 or 90 percentile of the SARS-cov2 immune subjects.

10. The method of claim 1, wherein the T cells are selected from the group consisting of CD8+ T cells, CD4+ T cells, TREGs, cytotoxic T cells, NKT cells, naïve T cells, central memory T cells, effector memory T cells, stem memory T cells (Tscm), iPSC-derived T cells and synthetic T cells.

11. The method of claim 1, wherein the T cells have one or more of the features selected from the group consisting of:
 (a) lacks the expression of one or more of endogenous T cell receptor chains;
 (b) lacks the expression of constant chains of endogenous T cell receptor $\alpha$, $\beta1$, $\beta2$, pre-TCR$\alpha$, $\gamma$ or $\delta$ or combination thereof;
 (c) lacks the expression of HLA;
 (d) lacks the expression of $\beta2$ microglobulin;
 (e) lacks the expression of CD52;
 (f) expresses an agent which enhances the activity of a SABR-expressing cell;
 (g) expresses an agent that provides co-stimulation to a SABR-expressing cell;
 (h) expresses a cytokine or a chemokine;
 (i) expresses an agent that that promotes the proliferation, persistence, expansion and/or activation of a SABR-expressing cell;
 (j) expresses an agent which increases the expression and/or activity of SABR chains;
 (k) expresses a soluble receptor;
 (l) expresses a second SABR;
 (m) expresses an inhibitory SABR that comprises an antigen binding domain, a transmembrane domain and an intracellular domain of an inhibitory molecule;
 (n) expresses a second SABR comprising an antigen binding domain, a transmembrane domain and a primary signaling domain;
 (o) expresses a second SABR comprising an antigen binding domain, a transmembrane domain, a costimulatory signaling domain but no primary signaling domain;
 (p) expresses a second SABR comprising an antigen binding domain, a transmembrane domain, a primary signaling domain and a costimulatory domain;
 (q) expresses an accessory module which increases, decreases, regulates or modifies the expression or activity of a SABR or a SABR-expressing cell, wherein the accessory module is selected from the group consisting of POL 1, PDL2, CD80, CD86, NEMO-K277A, K13-opt, MyD88, 41BBL, vFLIPK13, IL-7, IL-15, IL-21, and any combination thereof; and/or
 (r) expresses a therapeutic control selected from the group consisting of CNB30, a truncated epidermal growth factor receptor (tEGFR), truncated epidermal growth factor receptor viii (tEGFRviii), truncated CD 19 (tCD 19), truncated BCMA (tBCMA), icaspase-9 and an antibiotic resistance cassette.

12. The method of claim 1, wherein the SABR comprises:
 (a) at least one antigen binding domain and at least one transmembrane or a membrane anchoring domain; and/or
 (b) a targeting/binding moiety that is associated with one or more signaling domains.

13. The method of claim 12, wherein the antigen binding domain and/or the targeting moiety of the SABR comprises a member selected from the group consisting of a scFv, a vL, a vH, an antibody, an antibody fragment, an antibody like moiety, a Vα domain, a Vβ domain, a cytokine, a receptor and combination thereof.

14. The method of claim 1, wherein the SABR is selected from the group consisting of a Chimeric Antigen Receptor (CAR), an Antibody-TCR chimeric molecule (Ab-TCR), a TCR receptor fusion protein (TFP), a Synthetic Immune Receptor (SIR), a Tri-functional T cell antigen coupler (Tri-TAC or TAC), a z-SIR, a TRUCK, a Universal SABR, a Self-driving SABR, an Armored SABR, a Self-destruct SABR, a Conditional SABR, a Marked SABR, a Tandem SABR (tanSABR), a Dual SABR, a bispecific-SABR, and a safety SABR (sSABR).

15. The method of claim 1, further comprising a step wherein the T cells are stimulated with antigen presenting cells (APC) presenting SARS-cov2 encoded peptide antigens in vitro and/or in vivo: (a) before transduction with the nucleic acid encoding the SABR; (b) after transduction with the nucleic acid encoding the SABR; or (c) both before and after transduction with the nucleic acid encoding the SABR.

16. A method for generating a composition for the treatment of cancer and/or autoimmune disorders comprising:

transducing T cells that express a T-cell receptor that specifically binds to a SARS-cov2 encoded first antigen with a vector comprising a nucleic acid encoding at least one synthetic antigen binding receptor (SABR) specific for binding to a second antigen selected from the group consisting of CD5; CD19; CD123; CD22; CD30; CD171; CS1; C-type lectin-like molecule-1; CD33; epidermal growth factor receptor variant III (EGFRviii); ganglioside G2 (GD2); ganglioside GD3 (aNeu5Ac (2-8) aNeu5Ac (2-3) bDGalp (1-4) bDG1cp (1-1) Cer); TNF receptor family member B cell maturation (BCMA); Tn antigen; prostate-specific membrane antigen (PSMA); Receptor tyrosine kinase-like orphan receptor 1 (ROR1); Fms Like Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors; a glycosylated CD43 epitope expressed on nonhematopoietic cancers; Carcinoembryonic antigen (CEA); Epithelial cell adhesion molecule (EPCAM); B7H3 (CD276); KIT (CD117); Interleukin-13 receptor subunit alpha-2; Mesothelin; Interleukin 11 receptor alpha (IL-11Ra); prostate stem cell antigen (PSCA); Protease Serine 21; vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Folate receptor beta (FRb); Receptor tyrosine-protein kinase ERBB2; Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin 82; fibroblast activation protein alpha; insulin-like growth factor 1 receptor (IGF-1 receptor); carbonic anhydrase IX (CAIX); Proteasome Subunit, Beta Type, 9; glycoprotein 100 (gp100); oncogene fusion protein consisting of breakpoint cluster region (BCR) and Abelson murine leukemia viral oncogene homolog 1 (Abl) (bcrabl); tyrosinase; ephrin type-A receptor 2 (EphA2); sialyl Lewis adhesion molecule (sLe); ganglioside GM3 (aNeuSAc (2-3) bDClapd-4) bDGlcp(-1) Cer); transglutaminase 5 (TGS5); high molecular weight-melanoma associated antigen (HMWMAA); o-acetyl-GD2 ganglioside (OAcGD2); tumor endothelial marker 1 (TEM 1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen NY-BR-1; uroplakin 2 (UPK2); adrenoceptor beta 3 (ADRB3); pannexin 3 (PANX3); G protein-coupled receptor 20 (GPR20); lymphocyte antigen 6 complex, locus K 9 (L Y6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2; Melanoma-associated antigen 1 (MAGE-A1); ETS translocation-variant gene 6, located on chromosome 12p (ETV6-AML); sperm protein 17 (SPA17); X Antigen Family, Member IA (XAGEI); angiopoietin-binding cell surface receptor 2 (Tie 2); melanoma cancer testis antigen-1; melanoma cancer testis antigen-2; Fos-related antigen 1; tumor protein p53 (p53); p53 mutant; prostein; survivin; telomerase; prostate carcinoma tumor antigen-1; melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); transmembrane protease, serine 2 ETS fusion gene; N-Acetyl glucosaminyl-transferase V; paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYPIB 1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32; lymphocyte-specific protein tyrosine kinase (LCK); A kinase anchor protein 4 (AKAP-4); synovial sarcoma, X breakpoint 2 (SSX2); Receptor for Advanced Glycation Endproducts; renal ubiquitous 1 (RU1); renal ubiquitous 2 (RU2); legumain; intestinal carboxyl esterase; heat shock protein 70-2 mutated (mut hsp70-2); CD79a; CD79b; CD72; Leukocyte-associated immunoglobulin-like receptor 1 (LAI R 1; Fc fragment of IgA receptor; Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL 1), MPL; Biotin; c-MYC epitope Tag; CD34; LAMP1; TROP2; GFRalpha4; CDH17; CDH6; NYBR1; CDH19; CD200R; Slea; Fucosyl-GM1; PTK7; gpNMB; CDH1-CD324; DLL3; CD276/B7H3; IL 11 Ra; IL 13Ra2; CD179b-IGLII; TCR-gamma-delta; NKG2D; CD32; Tim1-/HVCR1; CSF2RA; TGF-betaR2; TCR-beta1 chain; TCR-beta2 chain; TCR-gamma chain; TCR-delta chain; FITC; Luteinizing hormone receptor (LHR); Follicle stimulating hormone receptor (FSHR); Gonadotropin Hormone receptor; CCR4; GD3; SLAMF6; SLAMF4; HIV1 envelope glycoprotein; HTLV1-Tax; CMV pp65; EBVEBNA3c; KSHV K8.1; KSHV-gH; GAD; PDL1; Guanylyl cyclase C (GCC); auto antibody to desmoglein 3 (Dsg3); auto antibody to desmoglein 1 (Dsg1); HLA-A; HLA-A2; HLA-B; HLA-C; HLA-DP; HLA-DM; HLA-DOA; HLA-DOB; HLA-DQ; HLA-DR; HLA-G; IgE; CD99; Ras G12V; Tissue Factor 1 (TF1); AFP; GPRC5D; Claudin18.2; P-glycoprotein; STEAP1; Liv1; Nectin-4; Cripto; gpA33; BST1/CD157; low conductance chloride channel; the antigen recognized by TNT antibody; CD229; Toso; and BAFF-R;

wherein the method does not comprise the expansion of the starting population of T cells in the presence of SARS-cov2 specific peptides or peptide libraries.

17. A composition for the treatment of cancer and/or autoimmune disorders generated by the method of claim 1 or 16.

18. A method of treatment of cancer and/or autoimmune disorders comprising administering to a subject in need thereof an effective amount of a composition of claim 17.

* * * * *